US007378495B2

(12) United States Patent
Correale et al.

(10) Patent No.: US 7,378,495 B2
(45) Date of Patent: May 27, 2008

(54) PTH-RP RELATED PEPTIDE CANCER THERAPEUTICS

(75) Inventors: Pierpaolo Correale, Siena (IT); Maria Grazia Cusi, Siena (IT); Guido Francini, Siena (IT)

(73) Assignee: Pevion Biotech, Ltd., Bern (CH)

( * ) Notice: Subject to any disclaimer, the term of this patent is extended or adjusted under 35 U.S.C. 154(b) by 128 days.

(21) Appl. No.: 10/691,125

(22) Filed: Oct. 21, 2003

(65) Prior Publication Data

US 2005/0033023 A1 Feb. 10, 2005

Related U.S. Application Data

(60) Provisional application No. 60/420,165, filed on Oct. 21, 2002.

(51) Int. Cl.
*C71K 1/00* (2006.01)
(52) U.S. Cl. .................................................. 530/350
(58) Field of Classification Search ................ 530/350
See application file for complete search history.

(56) References Cited

U.S. PATENT DOCUMENTS

| | | | |
|---|---|---|---|
| 5,114,843 A * | 5/1992 | Rosenblatt et al. | 435/7.21 |
| 5,626,845 A | 5/1997 | Yoneda et al. | |
| 5,880,093 A * | 3/1999 | Bagnoli | 514/12 |
| 5,993,817 A * | 11/1999 | Yoneda et al. | 424/158.1 |

FOREIGN PATENT DOCUMENTS

| | | | |
|---|---|---|---|
| EP | 0822200 A1 * | 6/1998 | |
| WO | WO 00/23594 | * 4/2000 | |
| WO | WO 00/61612 | 4/2000 | |
| WO | WO 00/69900 | * 11/2000 | |
| WO | WO 01/81415 A1 | 4/2001 | |

OTHER PUBLICATIONS

P. Correale, L. Michell, MT Del Vecchio, M. Sabatino, R. Petriolli, D. Pozzessere, S. Masili, G. Giorgi, L. Lozzi, P. Neri and G. Francini. A parathyroid-hormone-related-protein (PTH-rP)-specific cytotoxic T cell response induced by in vitro stimulation of tumour-infiltrating lymphocytes derived from prostate cancer metastases, with epitope peptide-loaded autologous dendritic cells and low-dose IL-2. British Journal of Cancer 1722-1730 (2001).
G. Francini, A. Scardino, K. Kosmatopoulos, F. A. Lemonnier, G. Campoccia, M. Sabatino, D. Pozzessere, R. Petrioli, L. Lozzi, P. Neri, G. Fanetti, M.G. Cusi, and P. Correale. High-Affinity HLA-A(*)02.01 peptides from parathyroid hormone-related protein generate in vitro and in vivo antitumor CTL response without autoimmune side effects. The Journal of Immunology (2002).
P. Correale, M.G. Cusi, M. Sabatino, L. Micheli, D. Pozzessere, C. Nencini, P.E. Valensin, R. Petrioli, G. Giorgi, R. Zurbriggen, R. Gluck, G. Francini. Tumour-associated antigen (TAA)-specific cytotoxic T cell (CTL) reponse in vitro and in a mouse model, induced by TAA-plasmids delivered by influenza virosomes. European Journal of Cancer 37, 2097-2103 (2001).

L.J. Suva, G.A. Winslow, R.E. H. Wettenhall, R.G. Hammonds, J.M. Moseley, H. Diefenbach-Jagger, C.P. Rodda, B.E. Kemp, H. Rodriguez, E.Y. Chen, P.J. Hudson, T.J. Martin, W.I. Wood. A parathyroid hormone-related protein implicated in malignant hypercalcemia: cloning and expression. Science Reports, (Aug. 1987).
R.G. Fenton, D.D. Taub, L.W. Kwak, M.R. Smith, D. L. Longo. Cytotoxic T-cell response and in vivo protection against tumor cells harboring activated ras proto-oncogenes. Journal of the Nat. Cancer Institute, vol. 85, No. 16, 1294-1302, (Aug. 1993).
S. Pascolo, N. Bervas, J.M. Ure, A.G. Smith, F.A. Lemonnier, and B. Peramau. HLA-A2.1-restricted education and cytolytic activity of CD8+ T lymphocytes from $\beta 2$ microglobulin ($\beta 2m$) HLA-A2.1 monochain transgenic H-$2D^b\beta 2m$ double knockout mice. Journal Exp. Med., vol. 185, No. 12, 2043-2051, (Jun. 1997).
R.A. Henderson, H. Michel, K. Sakaguchi, J. Shabanowitz, E. Appella, D.F. Hunt, V.H. Engelhard. HLA-A2.1-associated peptides from a mutant cell line: A second pathway of antigen presentation. Science, vol. 225, (Mar. 1992).
D.F. Hunt, R.A. Henderson, J. Shabanowitz, K. Sakaguchi, H. Michel, N. Sevilir, A.L. Cox, E. Appella, V.H. Engelhard. Characterication of peptides bound to the Class I MHC Molecule HLA-A2.1 by mass spectrometry. Science, vol. 255, Issue 5049, 1261-1263, (Mar. 1992).
P. Correale, K. Walmsley, C. Neiroda, S. Zaremba, M. Zhu, J. Scholm and K.Y. Tsang. In vitro generation of human cytotoxic T lymphocytes specific for peptides derived from prostate-specific antigen. Journal of the National Cancer Institute, vol. 89, 293-300 (1997).
P. Correale, K. Walmsely, S. Zaremba, M. Zhu, J. Schlom, K.Y. Tsang. Generation of human cytolytic T lymphocyte lines directed against prostate-specific antigen (PSA) employing a PSA oligoepitope peptide. Journal of National Cancer Institute, 293-300, (Feb. 1997).
P. Correale, M. Sabatino, M.G. Cusi, L. Micheli, C. Nencini, D. Pozzessere, R. Petrioli, A. Aquino, L. DeVecchis, M. Turriziani, S.P. Prete, R. Sanguedolce, L. Rausa, G. Giorgi, G. Francini. In vitro generation of cytotoxic T lymphocytes against HLA-A2.1-restricted peptides derived from human thymidylate synthase. Journal of Chemotherapy. 519-26; (Oct. 2001).
T. Wolfel, E. Klehmann, C. Muller, K.H. Schutt, K.H. Meyer zum Buschenfelde and A. Knuth. Lysis of human melanoma cells by autologous cytolytic T cell clones. Identification of human histocompatibility leukocyte antigen A2 as a restriction element for three different antigens. Journal of Experimental Medicine, vol. 170, 797-810, (1989).

(Continued)

*Primary Examiner*—Karen Cochrane Carlson
*Assistant Examiner*—Agnes B. Rooke
(74) *Attorney, Agent, or Firm*—Proskauer Rose LLP

(57) ABSTRACT

Compositions comprising PTH-rP peptides, combinations thereof, and multiepitope PTH-rP peptides, vectors for their delivery to antigen presenting cells, as well as methods are provided which are useful in the immunotherapy of parathyroid hormone related peptide expressing malignancies.

8 Claims, 7 Drawing Sheets

OTHER PUBLICATIONS

J.P. Eder, P.W. Kantoff, K. Roper, G. Xu, G.J. Bubley, J. Boyden, L. Gritz, G. Mazzara, W.K. Oh, P. Arlen, K.Y. Tsang, D. Panicali, J. Schlom, and D.W. Kufe. A Phase I trial of a recombinant vaccinia virus expressing prostate-specific antigen in advanced prostate cancer. Clinical Cancer Research, vol. 6, 1632-1638, (May 2000).

C. Brander, O.O. Yang, N.G. Jones, Y. Lee, P. Goulder, R.P. Johnson, A. Trocha, D. Colbert, C. Hay, S. Buchbinder, C.C. Bergmann, H.J. Zweerink, S. Wolinsky, W.A. Blattner, S.A. Kalams and B.D. Walker. Efficient processing of the immundominant, HLA-A *0201-restricted human immunodeficiency virus type 1 cytotoxic T-lymphocyte epitope despite multiple variations in the epitope flanking sequences. Journal of Virology, 10191-10198, (Dec. 1999).

M.R. Betts, J.P. Casazza, B.A. Patterson, S. Waldrop, W. Trigona, Tong-Ming Fu, F. Kern, LJ. Picker, and R.A. Koup. Putative Immunodominant human immunodeficiency virus-specific CD8$^+$ T-cell responses cannot be predicted by major histocompatibility complex class I haplotype. Journal of Virology, 9144-9151, (Oct. 2000).

S. Pascolo, N. Bervas, J.M. Ure, A.G. Smith, F.A. Lemmonnier, and B. Peramau. HLA-A2.1-restricted education and cytolytic activity of CD8$^+$T lymphocytes from $^\beta$2 microglobulin ($^\beta$2m) HLA-A2.1 monochain transgenic H-2D$^D$ $^\beta$2m double knockout mice. Journal of Experimental Medicine, vol. 185, No. 12, 2043-2051, (Jun. 1997).

K. Dunussi-Joannopoulos. Gene therapy vaccines: guiding the immune system to fight leukemia. The Journal of the Hellenic Society of Haematology, 124-134, (1999).

A. Zippelius, M.J. Pittet, P. Romero. Dissecting tumor antigen-specific CD8 T cell responses in cancer patients. Ludwig Institute for Cancer Research.

T.E. Sparer, S.G. Wynn, D.J. Clark, J.M. Kaplan, L.M. Cardoza, S.C. Wadsworth, A.E. Smith and L.R. Gooding. Generation of cytotoxic T lymphocytes against immunorecessive epitopes after multiple immunications with adenovirus vectors is dependent on haplotype. Journal of Virology, 2277-2284, (Mar. 1997).

G.R. Mundy and T.A. Guise. Role of parathyroid hormone-related peptide in hypercalcemia of malignancy and osteolytic bone disease. Endocrine-Related Cancer, 15-26, (1998).

T. Takeshita, H. Takahashi, S. Kozlowski, J.D. Ahlers, C.D. Pendleton, R.L. Moore, Y. Nakagawa, K. Yokomuro, B.S. Fox, D.H. Margulies, and J.A. Berzofsky. Molecular analysis of the same HIV peptide functionally binding to both a Class I and a Class II MHC molecule. The American Association of Immunologists, (1995).

V. Tsai, S. Southwood, J. Sidney, K. Sakaguchi, Y. Kawakami, E. Appella, A. Sette, and E. Celis. Identification of subdominant CTL epitopes of the GP100 melanoma-associated tumor antigen by primary in vitro immunication with peptide-pulsed dendritic cells. The Journal of Immunology, vol. 158: 1796-1802, (1997).

D.M. Pardoll. (Commentary) Inducing autoimmune disease to treat cancer. Proc. Natl. Acad. Sci. USA, vol. 96, 5340-5342, (May 1999).

D. O'Sullivan, T. Arrhenius, J. Sidney, Marie-France Del Guercio, M. Albertson, M. Wall, C. Oseroff, S. Southwood, S.M. Colon, Federico C.A. Gaeta, and A. Sette. On the interaction of promiscuous antigen peptides with different dr alleles. The Journal of Immunology, vol. 147, 2663-2669, No. 8, (Oct. 1991).

A. Heiser, P. Dahm, D.R. Yancy, M.A. Maurice, D. Boczkowski, S.K. Nair, E. Gilboa, and J. Vieweg. Human dendritic cells trasfected with RNA encoding prostate-specific antigen stimulate prostate-specific CTL responses in vitro. The Journal of Immunology, 164: 5508-5514 (2000).

S.A. Thomson, R. Khanna, J. Gardner, S.R. Burrows, B. Coupar, D.J. Moss and A. Suhrbier. Minimal epitopes expressed in a recombinant polyepitope protein are processed and presented to CD8$^+$ cytotoxic T cells: Implications for vaccine design. Proc. Natl. Acad. Sci., vol. 92, 5845-5849, (Jun. 1995).

J.S. Blanchet, D. Valmori, I. Dufau, M. Ayyoub, C. Nguyen, P. Guillaume, B. Monsarrat, J.C. Cerottini, P. Romero, and J.E. Gairin. A new generation of melan-A/MART-1 peptides that fulfill both increased immunogenicity and high resistance to biodegradation: implication for molecular anti-melanoma immunotherapy. The Journal of Immunology, vol. 167, 5852-5861, (2001).

J. Lu and E. Celis. Use of two predictive algorithms of the world wide web for the identification of tumor-reactive T-cell epitopes. Cancer Research, vol. 60, 5223-5227, (Sep. 2000).

F. Micheletti, A. Canella, S. Vertuani, M. Marastoni, L. Tosi, S. Volinia, S. Traniello, and R. Gavioli. Supra-agonist peptides enhance the reactivation of memory CTL responses. The Journal of Immunology, vol. 165, 4264-4271 (2000).

K. Kuzushima, N. Hayashi, H. Kimura, and T. Tsurumi. Efficient identification of HLA-A*2402-restricted cytomegalovirus-specific CD8$^+$ T-cell epitopes by a computer algorithm and an enzyme-linked immunospot assay. Blood, vol. 98, No. 6, (Sep. 2001).

K. Kyriakos, P. Papadopoulos, N. Suciu-Foca, C.S. Hesdorffer, S. Tugulea, A. Maffei, and P.E. Harris. Natually processed tissue-and differentiation state-specific autologous peptides bound by HLA Class I and II molecules of chronic myeloid leukemia blasts. Blood, vol. 90, No. 12, 4938-4946, (Dec. 1997).

I. Kawashima, V. Tsai, S. Southwood, K. Takesako, A. Sette, and E. Celis. Identification of HLA-A3-restricted cytotoxic T lymphocyte epitopes from carcinoembryonic antigen and HER-2/*nue* by primary in vitro immunization with peptide-pulsed dendritic cells. Cancer Research 59, 431-435, (Jan. 1999).

J.H. Kessler, N.J. Beekman, S.A. Bres-Vloemans, P. Verdijk, P.A. vanVeelen, A.M. Kloosterman-Joosten, D.C.J. Vissers, G. J.A. ten Bosch, M. G.D. Kester, A. Sijts, J.W. Drifhout, F. Ossendorp, R. Offringa, and C. J.M. Melief. Efficient Identficiation of novel HLA-A*0201-presented cytotoxic T lymphocyte epitopes in the widely expressed tumor antigen PRAME by proteasome-mediated digestion analysis. Journal of Exp. Med., vol. 193, No. 1, 73-88, (Jan. 2001).

A.K. Sharma, J.J. Kuhns, S. Yan, R.H. Friedline, B. Long, R. Tisch, and E.J. Collins. Class I major histocompatibility complex anchor substitutions alter the conformation of T cell receptor contracts. The Journal of Biological Chemistry, vol. 276, No. 24, 21443-21449, (Jun. 2001).

H. Margalit, J.L. Spouge, J.L. Cornette, K.B. Cease, C. Delisi, and J.A. Berzofsky. Predicion of immunodominant helper T.cell antigenic sites from the primary sequence. The Journal of Immunology, vol. 138, No. 7, 2213-2229, (Apr. 1987).

K.C. Parker, M.A. Bednarek, and J.E. Coligan. Scheme for ranking potential HLA-A2 binding peptides based on independent binding of individual peptide side-chains. Journal of Immunology, (1994), 152:163.

E. Keogh, J. Fikes, S. Southwood, E. Celis, R. Chesnut, and A. Sette. Identification of new epitopes from four different tumor-associated antigens: recognition of naturally processed eptiopes correlates with HLA-A*0201-binding affinity. The Journal of Immunology, (2001), 167: 787-796.

Y. Zhao, B. Gran, C. Pinilla, S. Markovic-Plese, B. Hemmer, A. Tzou, L.W. Whitney, W.E. Biddison, R. Martin, and R. Simon. Combinatorial peptide libraries and biometric score matrices permit the quantitative analysis of specific and degenerate interactions between clonotypic TCR and MHC peptide ligands. The Journal of Immunology, (2001), 167: 2130-2141.

B.M. Carreno, R.V. Turner, W.E. Biddison, and J.E. Coligan. Overlapping epitopes that are recognized by CD8$^+$ Class II-restricted and CD4$^+$ Class I-restricted cytotoxic T lymphocytes are contained within an influenza nucleoprotein peptide. The Journal of Immunology, vol. 148, No. 3, 894-899, (Feb. 1992).

S.A. Luykx-de Bakker, T.D. de Grunijl, R.J. Scheper, J. Wagstaff and H.M. Pinedo. Dendritic cells: a novel therapeutic modality. Annals of Oncology, vol. 10, 21-77, (1999).

S. Grabbe, S. Beissert, T. Schwarz, and R.D. Granstein. Dendritic cells as initiators of tumor immune response: a possible strategy for tumor immunotherapy? Immunology Today, vol. 16, No. 3, (1995).

R.M. Steinman, The dendritic cell system and its role in immunogenicity. Annual Review of Immunology, (1991), 9:271-96.

N. Romani, D. Reider, M. Heuer, S. Ebner, E. Kampgen, B. Eibl, D. Niederwieser, G. Schuler. Generation of mature dendritic cells from human blood. An improved method with special regard to clinical applicability. Journal of Immunological Methods, 196 (1996), 137-151.

I. Melero, N. Bach, and L. Chen. Minreview: Costimulation, tolerance and ignorance of cytolytic T lymphocytes in immune responses to tumor antigens. Life Sciences, vol. 60, No. 23, 2035-2041, (1997).

B.M. Vose and M. Moore. Human tumor-infiltrating lymphocytes: a marker of host response. Seminars in Hematology, vol. 22, No. 1, 27-40, (Jan. 1985).

A. van Pel, P. van der Bruggen, P.G. Coulie, V.G. Brichard, B. Lethe, B. van den Eynde, C. Uyttenhove, J.C. Renauld, and T. Boon. Genes coding for tumor antigens recognized by cytolytic T. lymphocytes. Immunological Reviews, (1995), No. 145.

G. Francini, K.Y. Tsang, G. Campoccia, D. Pozzessere, L. Lozzi, G. Fanetti, and P. Correale. Ex vivo generation and characterization of human cytotoxic T lymphocytes specific for HLA-A2.1 binding peptides derived from parathyroid related hormone peptide (PTH-rP). American Association of Cancer Research, 91$^{st}$ Annual Meeting, (Apr. 2000).

S.A. Rosenberg, J.R. Yannelli, J.C. Yang, S.L. Topalian, D.J. Schwarzentruber, J.S. Weber, D.R. Parkinsone, C.A. Seipp, J.H. Einhorn, D.E. White. Treatment of patients with metastatic melanoma with autologous tumor-infiltrating lymphocytes and interleukin 2. Journal of the National Cancer Institute, vol. 86, No. 15, (Aug. 1994).

S. Markowicz and E.G. Engleman. Granulocyte-macrophage colony-stimulating factor promotes differentiation and survival of human peripheral blood dendritic cells in vitro. The American Society for Clinical Investigation, Inc., vol. 85, 955-961, (Mar. 1990).

G. Francini, R. Petrioli, A. Manganelli, M. Cintorino, S. Marsili, A. Aquino and S. Mondillo. Weekly chemotherapy in advanced prostatic cancer. Br. Journal of Cancer, vol. 67, 1430-1436, (1993).

D. S. Coffey. Prostate Cancer; An overview of an increasing dilemma. Cancer Supplement, vol. 71, No. 3, (Feb. 1993).

T. Wolfel, E. Klehmann, C. Muller, Klaus-Hermann Schutt, Karl-Hermann Meyer Zum Buschenfelde, and A. Knuth. Lysis of human melanoma cells by autologous cytolytic T cell clones. Identification of human histocompatibility leukocyte antigen A2 as a restriction element for three different antigens. Journal Exp. Med., vol. 170, 797-810, (Sep. 1989).

S.L. Topalian, D. Solomon, and S.A. Rosenberg. Tumor-specific cytolysis by lymphocytes infiltrating human melanomas. The Journal of Immunology, vol. 142, No. 10, 3174-37-25, (May 1989).

T.A. Guise, M.D. Parathyroid hormone-related protein and bone metastases. Cancer Supplement, vol. 80, No. 8, (Oct. 1997).

R.D. Rubens. Bone metastases—the clinical problem. European Journal of Cancer, vol. 34, No. 2, 210-213, (1998).

V. Grill, W. Rankin, and T.J. Martin. Original Paper: Parathyroid hormone-related protein (PTHrP) and hypercalcaemia. European Journal of Cancer, vol. 34, No. 2, 222-229, (1998).

G.R. Mundy, M.D. Mechanisms of bone metastasis. Cancer Supplement, vol. 80, No. 8, (Oct. 1997).

J.J. Yin, K. Selander, J.M. Chirgwin, M. Dallas, B.G. Grubbs, R. Wieser, J. Massague, G.R. Mundy, and T.A. Guise. TGF-β signaling blockade inhibits PTHrP secretion by breast cancer cells and bone metastases development. The Journal of Clinical Investigation, vol. 103, No. 2, (Jan. 1999).

T. Yoneda. Original Paper: Cellular and molecular mechanisms of breast and prostate cancer metastasis to bone. European Journal of Cancer, vol. 34, No. 2, 240-245, (1998).

B. Lanske, M. Amling, L. Neff, J. Guiducci, R. Baron, and H.M. Kronenberg. Ablation of the PTHrP gene or the PTH/PTHrP receptor gene leads to distinct abnormalities in bone development. The Journal of Clinical Investigation, vol. 104, No. 4, (Aug. 1999).

S.J. Vargas, M.T. Gillespie, G.J. Powell, J. Southby, J.A. Danks, J.M. Moseley, and T.J. Martin. Localization of parathyroid hormone-related protein mRNA expression in breast cancer and metastatic lesions by in situ hybridization. Journal of Bone and Mineral Research, vol. 7, No. 8, (1992).

J.M. Moseley, M. Kubota, H. Diefenbach-Jagger, R.E.H. Wettenhall, B.E. Kemp, L.J. Suva, C.P. Rodda, P.R. Ebeling, P.J. Hudson, J.D. Zajac, and T.J. Martin. Parathyroid hormone-related protein purified from a human lung cancer cell line. Proc. Natl. Acad. Sci., USA, vol. 84, 5048-5052, (Jul. 1987).

R. Cibotti, J.M. Kanellopoulos, Jean-Pierre Cabanilos, O. Halle-Panenko, K. Kosmatopoulos, E. Sercarz, and P. Kourilsky. Tolerance to a self-protein involves its immunodominant but does not involve its subdominant determinants. Proc. Natl. Acad. Sci. USA, vol. 89, 416-420, (Jan. 1992).

G. Murphy, B. Tjoa, H. Ragde, G. Kenny, and A. Boynton. Phase I Clinical Trial: T-cell therapy for prostate cancer using autologous dendritic cells pulsed with HLA-A0201-specific peptides from prostate-specific membrane antigen. The Prostate 29:371-380 (1996).

P.F. Robbins, and Y. Kawakami. Human tumor antigens recognized by T cells. Current Opinion in Immunology 8:628-636, (1996).

S. Jung, and H.J. Schluesener. Human T lymphocytes recognize a peptide of single point-mutated, oncogenic ras proteins. Journal Exp. Med., vol. 173, 273-276, (Jan. 1991).

H. Firat, F. Garcia-Pons, S. Tourdot, A. Pascolo, A. Scardino, Z. Garcia, Marie-Louise Michel, R.W. Jack, G. Jung, K. Kosmatopoulos, L. Mateo, A Suhrbier, F.A. Lemonnier, and P. Langlade-Demoyen. European Journal of Immunology, 29:3112-3121, (1999).

D.F. Hunt, R.A. Henderson, J.Shabanowitz, K. Sakaguchi, H. Michel, N. Sevilir, A.L. Cox, E. Appella, V.H. Engelhard. Characterization of peptides bound to the Class I MHC Molecule HLA-A2.1 by mass spectrometry. Science, vol. 255, 1261-1263, (Mar. 1992).

K. Falk, O. Rotzschke, S. Stevanovic, G. Jung, and Hans-Georg Rammensee. Allele-specific motifs revealed by sequencing of self-peptides eluted from MHC molecules. Nature, vol. 351, 290-296, (May 1991).

Jos G. A. Houbiers, H.W. Nijman, S.H. van der burg, Jan Wouter Drifhout, P. Kenemans, C.J.H. van de Velde, A. Brand, F. Momburg, W.M. Kast, and C.J.M. Melief. In vitro of human cytotoxic T lymphocyte responses against peptides of mutant and wild-type p53*, European Journal of Immunology, 23:2072-2077, (1993).

S.I. Abrams, M.J. Dobrzanski, D.T. Wells, S.F. Stanziale, S. Zaremba, L. Masuelle, J.A. Kantor and J. Schlom. Peptide-specific activation of cytolytic CD4$^+$ T lymphocytes against tumor cells bearing mutated epitopes of K-$ras$ p21. European Journal of Immunology, 25:2588-2597, (1995).

R.G. Fenton, D.D. Taub, L.W. Kwak, M.R. Smith, D.L. Longo, Cytotoxic T-cell response and in vivo protection against tumor cells harboring activated ras proto-oncogenes. Journal of the National Cancer Institute, vol. 85, No. 16, (Aug. 1993).

E. Keogh, J. Fikes, S. Southwood, E. Celis, R. Chestnut, and A. Sette. Identification of new epitopes from four different tumor-associated antigens: Recognition of naturally processed eptiopes correlates with HLA-A*0201-binding affinity. The Journal of Immunology, 167:787-796, (2001).

V. Cerundolo, J. Alexander, K. Anderson, C. Lamb, P. Cresswell, A. McMichael, F. Gotch, and A. Townsend. Presentation of viral antigen controlled by a gene in the major histocompatibility complex. Nature, vol. 345, (May 1990).

P. van der Bruggen, C. Traverari, P. Chomez, C. Lurquin, E. De Plaen, B. Van den Eynde, A. Knuth, T. Boon. A gene encoding an antigen recognized by cytolytic T. lymphocytes on a human melanoma. Science, vol. 254, 1643-1647, (Dec. 1991).

N.J. Crowley, T.L. Darrow, M. Ann Quinn-Allen, and H.F. Seigler. MHC-restricted recognition of autologous melanoma by tumor-specific cytotoxic T cells. The Journal of Immunology, vol. 146, No. 5, 1692-1699, (Mar. 1991).

S.A. Rosenberg, J.C. Yang, D.J. Schwartzentruber, P. Hwu, F.M. Marincola, S.L. Topallian, N.P. Restifo, M.E. Dudley, S.L. Schwarz, P.J. Spiess, J.R. Wunderlich, M.R. Parkhurst, Y. Kawakami, C.A. Seipp, J.H. Einhom and D.E. White, Nature Medicine, vol. 4, No. 3, 321-327, (Mar. 1998).

K.Y. Tsang, S. Zaremba, C.A. Nieroda, M.Z. Zhu, J.M. Hamilton, J. Scholm. Generation of human cytotoxic T cells specific for human carcinoembryonic antigen epitopes from patients immunized with recombinant vaccinia-CEA vaccine. Journal of the National Cancer Institute, vol. 87, No. 13, (Jul. 1995).

S.A. Rosenberg, J.C. Yang, D.J. Schwartzentruber, P. Hwu, F.M. Marincola, S.L. Topalian, N.P. Restifo, M. Sznol, S.L. Schwarz, P.J. Spiess, J.R. Wunderlich, C.A. Seipp, J.H. Einhom, L. Rogers-Freezer, and D.E. White. Impact of cytokine administration of the generation of antitumor reactivity in patients with metastatic melanoma receiving a peptide vaccine. The Journal of Immunology, 163:1690-1695, (1999).

* cited by examiner

SEQUENCE LISTING

<160> NUMBER OF SEQ ID NOS: 9

<210> SEQ ID NO 1
<211> LENGTH: 141
<212> TYPE: PRT
<213> ORGANISM: Homo sapiens
<220> FEATURE:
<221> NAME/KEY: MISC_FEATURE
<223> OTHER INFORMATION: Human PTH-rP amino acid sequence

<400> SEQUENCE: 1

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

-continued

```
Thr Ala Glu Ile Arg Ala Thr Ser Glu Val Ser Pro Asn Ser Lys Pro
         35                  40                  45

Ser Pro Asn Thr Lys Asn His Pro Val Arg Phe Gly Ser Asp Asp Glu
     50                  55                  60

Gly Arg Tyr Leu Thr Gln Glu Thr Asn Lys Val Glu Thr Tyr Lys Glu
 65                  70                  75                  80

Gln Pro Leu Lys Thr Pro Gly Lys Lys Lys Gly Lys Pro Gly Lys
                 85                  90                  95

Arg Lys Glu Gln Glu Lys Lys Lys Arg Arg Thr Arg Ser Ala Trp Leu
             100                 105                 110

Asp Ser Gly Val Thr Gly Ser Gly Leu Glu Gly Asp His Leu Ser Asp
             115                 120                 125

Thr Ser Thr Thr Ser Leu Glu Leu Asp Ser Arg Arg His
             130                 135                 140
```

<210> SEQ ID NO 2
<211> LENGTH: 9
<212> TYPE: PRT
<213> ORGANISM: Homo sapiens
<220> FEATURE:
<221> NAME/KEY: MISC_FEATURE
<223> OTHER INFORMATION: PTR-1

<400> SEQUENCE: 2

```
Ala Val Ser Glu His Gln Leu Leu His
 1               5
```

<210> SEQ ID NO 3
<211> LENGTH: 10
<212> TYPE: PRT
<213> ORGANISM: Homo sapiens
<220> FEATURE:
<221> NAME/KEY: MISC_FEATURE
<223> OTHER INFORMATION: PTR-2

<400> SEQUENCE: 3

```
Phe Leu His His Leu Ile Ala Glu Ile His
 1               5                  10
```

<210> SEQ ID NO 4
<211> LENGTH: 9
<212> TYPE: PRT
<213> ORGANISM: Homo sapiens
<220> FEATURE:
<221> NAME/KEY: MISC_FEATURE
<223> OTHER INFORMATION: PTR-3

<400> SEQUENCE: 4

```
Trp Leu Asp Ser Gly Val Thr Gly Ser
 1               5
```

<210> SEQ ID NO 5
<211> LENGTH: 9
<212> TYPE: PRT
<213> ORGANISM: Homo sapiens
<220> FEATURE:
<221> NAME/KEY: MISC_FEATURE
<223> OTHER INFORMATION: PTR-4

<400> SEQUENCE: 5

```
Thr Ser Thr Thr Ser Leu Glu Leu Asp
 1               5
```

<210> SEQ ID NO 6

-continued

```
<211> LENGTH: 13
<212> TYPE: PRT
<213> ORGANISM: Hepatitis B virus
<220> FEATURE:
<221> NAME/KEY: MISC_FEATURE
<223> OTHER INFORMATION: HBV core antigen derived T helper epitope

<400> SEQUENCE: 6

Thr Pro Pro Ala Tyr Arg Pro Pro Asn Ala Pro Ile Leu
1 5 10

<210> SEQ ID NO 7
<211> LENGTH: 26
<212> TYPE: DNA
<213> ORGANISM: Artificial
<220> FEATURE:
<223> OTHER INFORMATION: PTH-rP sense primer

<400> SEQUENCE: 7
ttggatccat gcagcggaga ctggtt 26

<210> SEQ ID NO 8
<211> LENGTH: 28
<212> TYPE: DNA
<213> ORGANISM: Artificial
<220> FEATURE:
<223> OTHER INFORMATION: PTH-rP antisense primer

<400> SEQUENCE: 8
ccgaattctc aatgcctccg tgaatcga 28

<210> SEQ ID NO 9
<211> LENGTH: 540
<212> TYPE: DNA
<213> ORGANISM: Homo sapiens
<220> FEATURE:
<221> NAME/KEY: misc_feature
<223> OTHER INFORMATION: PTH-rP cDNA sequence

<400> SEQUENCE: 9
cgatgcagcg gagactggtt cagcagtgga gcgtcgcggt gttcctgctg agctacgcgg 60
tgccctcctg cgggcgctcg gtggagggtc tcagccgccg cctcaaaaga gctgtgtctg 120
aacatcagct cctccatgac aaggggaagt ccatccaaga tttacggcga cgattcttcc 180
```

```
ttcaccatct gatcgcagaa atccacacag ctgaaatcag agctacctcg gaggtgtccc 240
ctaactccaa gccctctccc aacacaaaga accaccccgt ccgatttggg tctgatgatg 300
agggcagata cctaactcag gaaactaaca aggtggagac gtacaaagag cagccgctca 360
agacacctgg gaagaaaaag aaaggcaagc ccgggaaacg caaggagcag gaaaagaaaa 420
aacggcgaac tcgctctgcc tggttagact ctggagtgac tgggagtggg ctagaagggg 480
accacctgtc tgacacctcc acaacgtcgc tggagctcga ttcacggagg cattgaaatt 540
```

PTH-RP RELATED PEPTIDE CANCER THERAPEUTICS

RELATED APPLICATION

This application claims priority to U.S. Provisional Application No. 60/420,165 filed Oct. 21, 2002, incorporated by reference herein in its entirety.

FIELD OF THE INVENTION

The present invention relates to the fields of molecular biology and immunology. Specifically, this invention relates to the generation of immune responses effective against tumors and metastases expressing parathyroid hormone-related peptide.

BACKGROUND OF THE INVENTION

Prostate cancer is the second leading cause of cancer-related death in males in the United States and Europe. One cause of the grave morbidity and mortality related to this malignancy is the development of hormone resistant metastatic bone metastases. Indeed, bone is among the most common sites of metastases for many other common cancers, including lung, breast, and prostate cancer, as well as myeloma and lymphoma. The clinical sequelae of skeletal involvement by tumor metastases includes such complications as pathological fractures, spinal cord compression, hypercalcemia, as well as intractable pain believed to be caused by pressure from the expanding tumor mass, the release of cytokines and the spontaneous formation of small fractures in the metastatic bone. Bone metastasis invariably carries a grim prognosis for the cancer patient, as cure is no longer considered clinically achievable and treatment is limited to palliation in order to make the terminal patient more comfortable.

Because of the lack of therapeutic treatments for patients whose cancers have metastasized, intensive investigation has begun to focus on immunological or vaccination approaches to therapy. One of the problems encountered with vaccination approaches to human malignancy, however, is the mechanism of central and peripheral tolerance that limits the repertoire of self-reactive T cells to those of low avidity to prevent autoimmunity, making it difficult to elicit T cell responses that result in the attack of tumor cells. A primary goal of cancer immunotherapy, therefore, is the breaking of anergy and tolerance with concomitant activation and differentiation of tumor-reactive T cells. Because the balance between immunity and tolerance is in large part regulated at the immunologic interface between T cells and specialized cells that present antigens to T cells, such antigen-presenting cells, particularly dendritic cells, represent important targets for cancer immunotherapy.

Dendritic cells (DCs) are specialized antigen-presenting cells (APCs) strategically located in tissues where they efficiently capture and process antigens. DCs mature in response to exposure to pathogens or inflammatory mediators upon which they begin to express molecules which promote not only the migration of DCs to T cell zones of secondary lymphoid organs, but also upregulate the expression of major histocompatibility complex (MHC), and of several costimulatory and adhesion molecules. Upregulation of these factors permits the formation of a synapse between mature DCs and naive T cells which leads to the stimulation and maturation of T cells specific for antigens presented by DCs with which they have come into contact. Because of their role in stimulating and activating T cells, the loading of DCs with antigens in the form of proteins, peptides or RNA/DNA encoding tumor-associated antigens is an important element in the development of vaccines for overcoming tolerance to self-antigens.

The design of immunotherapeutic approaches to cancer also requires the identification of target antigens against which an effective immune response may be stimulated. While a number of tumor-specific antigens (TSAs) and tumor-associated antigens (TAAs) have been identified for certain types of tumors, the delivery and presentation of a tumor-associated or tumor-specific self-antigen in a form that is effective to induce T cell responses remains a major challenge. Cytotoxic T lymphocytes (CTLs) recognize protein antigens as small peptide products of cytoplasmic proteolysis bound to major histocompatibility complex I (MHC I) molecules, while helper T cells recognize peptides of variable sizes complexed to MHC II. Epitope peptide binding to specific class I or II human leukocyte antigen (HLA) isotypes is determined by consensus motifs present in the amino acid sequences of the antigen peptides. Because the quality and duration of T cell receptor signaling at the synapse between DC and T cell influences T cell activation, the ability of a peptide antigen to elicit responses will be related to its affinity for the MHC molecule, determined by the presence of favored amino acids at anchor positions involved in MHC binding and by the presence of amino acids involved in the recognition of the MHC-peptide complex by the T cell receptor. Thus, the identification, delivery and presentation of a tumor-associated antigen in a form effective to elicit tumor- and metastasis-specific T cell responses presents a significant advance in the clinical immunotherapy of malignancy.

DETAILED DESCRIPTION OF THE INVENTION

Figure 1A:
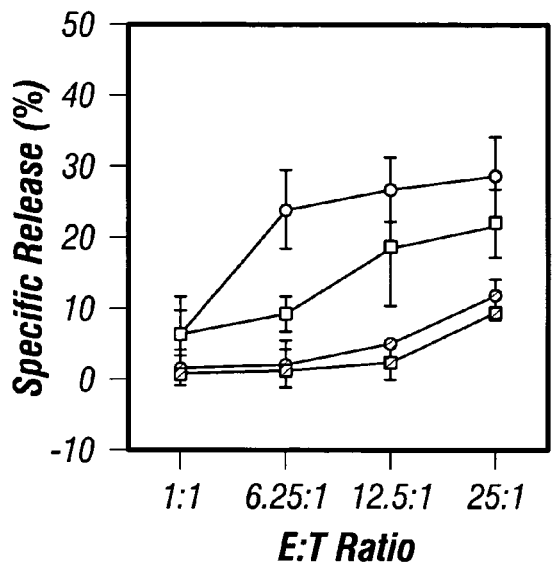
FIG. 1: this figure shows that intranasal immunization with virosome containing parathyroid hormone related peptide (PTH-rP) encoding plasmid elicits an effective immune response against PTH-rP expressing target cells. The figure also shows that concurrent administration of IL-2 enhances the immune response against PTH-rP expressing cells. PTH-rP specific cytotoxic activity of mouse spleens pooled from different mouse groups was measured against P815 target cells transfected with the PTH-rP gene (FIG. 1A), P815 target cells transfected with the PTH-rP gene in the presence of anti-H2$^{kd}$ monoclonal Ab mAb (FIG. 1B), P815 transfected with pcDNA3 (FIG. 1C), P815 target cells transfected with PTH-rP gene (FIG. 1D) in presence of anti CD8 mAb. Group A (�odot◻odot) was immunized with intranasal (i.n.) GC90 virosome, group B (-■-) with intranasal pcDNA3-virosome, group C (odot○odot) with intranasal GC90 virosome+daily subcutaneous (s.c.) IL-2, and group D (-●-) with intranasal pcDNA3 virosome+daily sc IL-2. The data are from three different experiments with similar results. The differences of groups A and C respectively, in comparison with those of groups B and D, were statistically significant (P<0.05)
Figure 1B:
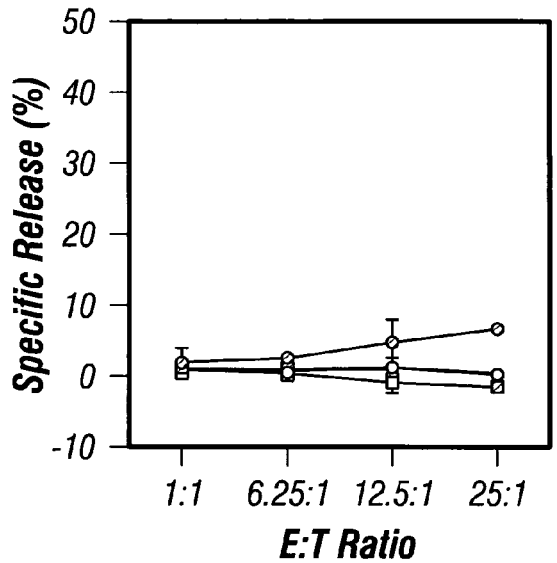
Figure 1C:
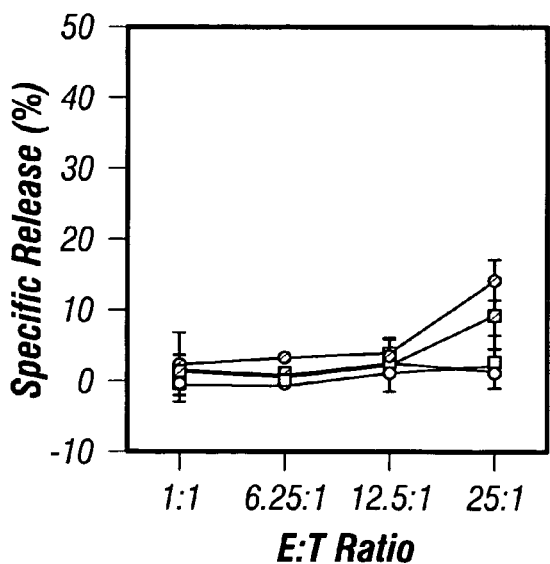
Figure 1D:
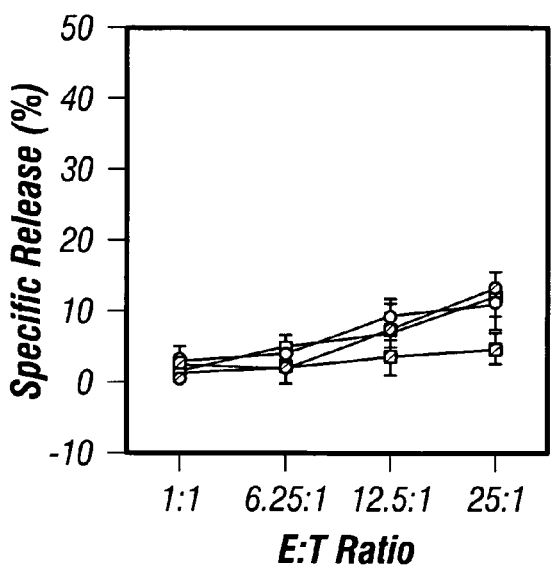

Various publications or patents are referred to in parentheses or otherwise throughout this application to describe the state of the art to which the invention pertains. Each of these publications or patents is incorporated by reference herein.

Advanced cancers frequently metastasize to bone. The majority of the approximately 1 million patients who die every year of breast, prostate, or lung cancer in the United States and Western Europe have bone metastases (Mundy and Guise, Endocrine-Related Cancer (1998) 5: 15-26). Experimental evidence has shown that the survival and growth of tumor cells in bone tissue is promoted by their interaction with the normal cells involved in bone turnover, and particularly by the abnormal activation of osteoclasts, which makes the bone microenvironment favorable for tumor cell implantation and growth. Parathyroid hormone-related peptide (PTH-rP) is a protein approximately 177 amino acids in length that is produced by many tumor phenotypes and their bone metastases. The PTH-rP protein is expressed in 90% of primary prostate and lung spinocellular carcinomas, and 50% of primary breast cancers (Vargas et al., J. Bone Min. Res. 7: 971-979, 1992). PTH-rP is involved in tumor cell metastasis to the bone tissue, as it has been shown to stimulate osteoclast production of growth factors, cytokines and TGF-β, which in turn activate a positive feedback loop by promoting PTH-rP expression and tumor cell growth, making bone a feasible microenvironment for the survival of malignant cells. PTH-rP has some functional and amino acid analogies with parathyroid hormone (PTH) and is capable of acting on the same cell membrane receptor(s). As a result of these PTH mimetic actions, when PTH-rP is produced in large amounts by tumor cells, it contributes to both osteolytic bone disease and hypercalcemia of malignancy (HHM). As PTH-rP plays a major role in the occurrence and development of bone metastases, it has become a biological target for novel immunotherapeutic approaches to PTH-rP expressing malignancies and bone metastases.

Aspects of the instant invention are based on the discovery that PTH-rP peptides (peptides derived from the tumor-associated self-antigen PTH-rP) can be effectively used to break the tolerance and anergy of T cells to PTH-rP, thus making PTH-rP expressing tumors visible to the immune system and allowing for the generation of immune responses that attack such tumors and their metastases, without toxicity to other tissues. Accordingly, the present invention provides compositions and methods for inducing an effective immune response to cancer cells expressing parathyroid hormone-related peptide (PTH-rP). In a first aspect, the invention provides methods of identifying PTH-rP peptides capable of stimulating the proliferation and activation of effector T cells that are specific for cancer cells expressing PTH-rP. These peptides are fragments (herein also referred to as subsequences) selected from the amino acid sequence of mature PTH-rP (SEQ ID. NO:1) and they encompass MHC I as well as MHC II binding peptides. A PTH-rP peptide of the invention can be as short as 8 amino acids in length or as long as 30 amino acids, as it is well known that MHC I binding peptides typically range in size from 8-11 amino acids in length, while MHC II binding peptide length varies from about 10 amino acids to approximately 30 amino acids, with a majority ranging in length from 12 to 19 amino acids. There are a number of ways that are suitable to identify T cell stimulatory PTH-rP peptides. For example, PTH-rP sequences which are candidate MHC binding peptides can be predicted based on the consensus amino acid sequences for binding any known MHC molecule. Many of these consensus motif sequences have been described for the most common MHC (also referred to as human leukocyte antigen or HLA), isotypes. Examples of MHC II consensus motifs have been described in O'Sullivan et al., J. Immunol. 147: 2663-2669, 1991, while examples of favored MHC I binding motifs can be found in Parker et al., J. Immunol. 152: 163-175, 1994. These amino acid sequence motifs provide guidance as to how to detect potential PTH-rP epitopes. For example, a consensus motif might specify that the residue at a first position may be any one of a restricted number of amino acid residues, that the residue at the second position must invariably be a certain amino acid, but that the residue at other positions can be any amino acid residue, while the residue at the last position must be a certain amino acid.

In addition, algorithms based on score matrix-based approaches for predicting T cell-stimulatory candidate peptides have been described (Zhao et al., J. Immunol. 167: 2130-2141, 2001; Pinilla et al. Cancer Res. 61: 5153, 2001). These approaches allow the identification of PTH-rP peptides that bind to a particular MHC molecule and interact with a T cell receptor to induce a T cell response. Some of the most commonly used predictive algorithms are available on the Internet, such as the NIH algorithm "BIMAS" which ranks potential MHC binders according to the predictive half-time dissociation of peptide/MHC complexes; the "SYFPEITHI" algorithm which ranks peptides according to a score that takes into account the presence of primary and secondary MHC-binding anchor residues; "EpiPred" which uses excel spreadsheets to analyze many alleles according to algorithms and virtual matrices; as well as "Epipredict", "Tepitope", "Propred", "MHC-Thread" and other programs. Using any of these algorithms, the amino acid sequence of PTH-rP (SEQ ID NO: 1) may be rapidly screened for top ranking PTH-rP peptides based on their binding score to any choice of MHC I or MHC II isotype and its interaction with T cell receptors.

Once identified by any of the methods outlined above, the PTH-rP peptides of the present invention may be produced by chemical synthesis, or they may be of natural or recombinant origin. Natural PTH-rP peptides can be obtained by elution from MHC molecules, isolated from patients with a PTH-rP expressing cancer, or isolated from cultured cells which express PTH-rP peptides. Those skilled in the art also can readily follow known methods for isolating peptides in order to obtain isolated PTH-rP peptides. These may include immunochromatography, HPLC, size-exclusion chromatography, ion-exchange chromatography and immune-affinity chromatography. The PTH-rP peptides may also be recombinantly produced using a nucleic acid molecule encoding the peptide. In addition, their sequences may be modified sequence as long as they retain the ability to stimulate T cells when presented. Thus, in a further preferred embodiment, the invention embraces functional variants of PTH-rP peptides. As used herein, a "functional variant" or "variant" of a PTH-rP immunogenic peptide is a peptide which contains one or more modifications to the primary amino acid sequence of an immunostimulatory PTH-rP peptide while retaining the immunostimulatory effect disclosed herein. If a functional variant of a PTH-rP peptide involves an amino acid substitution, conservative amino acid substitutions typically will be preferred, i.e., substitutions which retain a property of the original amino acid such as charge, hydrophobicity, conformation, etc. Examples of conservative substitutions of amino acids include substitutions made among amino acids within the following groups: (1) M, I, L, V; (2) F, Y, W; (3) K, R, H; (4) A, G; (5) S, T; (6) Q, N; and (7) E, D. Binding of a variant PTH-rP peptide to the MHC molecule and stimulation of the T cell by the variant peptide presented by the MHC molecule indicates that the variant peptide is a functional variant.

Modifications which generate functional variants of PTH-rP peptides can may be made in order to enhance peptide stability in an expression system, to enhance the stability of protein-protein binding such as HLA-peptide binding, or to increase the avidity of T cell receptors. The amino acid residues of the PTH-rP peptide can be mutated according to the principles of MHC and T cell receptor contact points outlined above. Again, any method for preparing modified or variant peptides can be employed, such as synthesis of the modified or variant peptide or its recombinant production using a mutated nucleic acid molecule. The identification of additional or optimized immunostimulatory PTH-rP peptides may also include the step of comparing the stimulation of the T cell by the PTH-rP peptide and the stimulation of the T cell by the functional variant as a determination of the effectiveness of the stimulation of the T cell by the functional variant. By comparing the functional variant PTH-rP peptide with a known PTH-rP peptide, peptides with increased T cell stimulatory properties can be prepared.

The individual PTH-rP peptides may also have one or more amino acids added to either or both ends. Nested sets of MHC binding peptides have been identified, wherein the peptides share a core sequence but have different amino acids at their amino and/or carboxyl terminal ends. For example residues of the peptide which contact MHC pockets may be kept constant while other residues may be varied. Alternatively, specified amino acid substitutions may be prepared to generate functional variants of PTH-rP peptides which retain binding to MHC and T cell receptor. The binding of the PTH-rP peptide to the MHC molecule and stimulation of the T cell are then assessed according to standard procedures. For example, as exemplified below, the PTH-rP peptide can be contacted with an antigen presenting cell that contains the MHC molecule which binds the PTH-rP peptide to form a complex of the peptide and antigen presenting cell. This complex can then be contacted with a T cell which recognizes the PTH-rP peptide presented by the MHC binding molecule. T cells can be obtained from a patient suffering from a tumor expressing PTH-rP or from healthy subjects. Recognition of PTH-RP peptides or functional variants thereof by the T cells can be determined by measuring an indicator of T cell stimulation such as TNF or IFNγ production. Similar procedures can be carried out for identification and characterization of other PTH-rP peptides. Additional methods of selecting and testing peptides for MHC binding and T cell recognition are well known in the art.

Thus, methods for identifying PTH-rP peptides, and functional variants thereof, are provided. In general, the methods include selecting a PTH-rP peptide predicted to bind to a preselected MHC and/or stimulating a TCR, testing the binding of the PTH-rP peptide to an MHC molecule and generating T cells which are activated by the PTH-rP peptide presented by the MHC molecule. In a preferred embodiment, the PTH-rP peptide comprises any amino acid subsequence of SEQ ID NO: 1. In more preferred embodiments, the PTH-rP peptide comprises the amino acid sequence of SEQ ID NO:5. In another preferred embodiments, the PTH-rP peptide comprises the amino acid sequence of SEQ ID NO:3. In yet another much preferred embodiment, the PTH-rP peptide comprises any or all of the amino acid sequences of SEQ ID NO:2, SEQ ID NO:3, SEQ ID NO:4, and SEQ ID NO:5. These peptides can be used to generate PTH-rP specific T-cell responses with anti-tumor activity. For example, autologous antigen presenting cells can be isolated from a patient and treated to obtain cells which present PTH-rP peptide epitopes in association with both MHC (HLA) class I and II molecules. Thus, these cells are capable of stimulating both $CD4^+$ and $CD8^+$ cell responses.

According to a preferred aspect of the invention, the PTH-rP peptides are used to pulse autologous antigen presenting or dendritic cells in vitro according to methods known in the art. The PTH-rP peptide-pulsed autologous antigen presenting or dendritic cells can then be reinfused into the subject afflicted with the PTH-rP expressing malignancy to evoke T cell responses against the tumor and its metastases in the form of a cellular vaccine. In another preferred embodiment, the PTH-rP peptides of the invention can be administered by injection to a subject in the form of a peptide-based vaccine. Preferably, the PTH-rP peptides are injected intradermally or subcutaneously to allow for uptake by or exposure to antigen presenting cells located in the skin, epidermis or dermis, although other routes of administration known in the art may be equally suitable and are intended to be included in the present invention.

The PTH-rP peptides may also be modified to be more resistant to hydrolysis by proteases, such as by containing D-amino acids or one or more non-hydrolyzable peptide bonds linking amino acids. Non-hydrolyzable peptide bonds are well-known in the art and may include -psi[$CH_2$NH]-reduced amide peptide bonds, -psi[$COCH_2$]-ketomethylene peptide bonds, -psi[CH(CN)NH]-(cyanomethylene) amino peptide bonds, -psi[$CH_2$CH(OH)]-hydroxyethylene peptide bonds, -psi[$CH_2$O] peptide bonds, and -psi[$CH_2$S]-thiomethylene peptide bonds. Alternatively, the PTH-rP peptides may be rendered more resistant to degradation or their structural stability may be increased-by the inclusion of nonpeptide moieties. Preferably, the nonpeptide moieties permit the peptides to retain their natural conformation, or stabilize an optimized bioactive confirmation. Examples of suitable substitutions include D-isomer amino acids, N-methyl amino acids, L-isomer amino acids, modified L-isomer amino acids and cyclized derivatives. Such peptide mimetics can be tested in molecular or cell-based binding assays to assess the effect of the substitution(s) on conformation and/or activity. Procedures of medicinal chemistry may be applied by one skilled in the art using routine experimental methods of e.g. rational drug design, molecular modeling based on structural information from nuclear magnetic resonance or X-ray diffraction data, and other computational methods. Thus, the invention includes all of the foregoing modifications to the PTH-rP peptides.

In another preferred embodiment of the invention the PTH-rP peptides are used to pulse antigen presenting or dendritic cells and the peptide-pulsed antigen-presenting or dendritic cells are co-cultured with T cells in vitro. Preferably, the T cells are tumor-infiltrating lymphocytes (TILs) isolated from a subject with a PTH-rP expressing malignancy, although they may also be circulating lymphocytes, such as those obtained from peripheral blood monocytes (PBMCs). Isolation of TILs or PBMCs is a procedure that is well known in the art and it is preferable that the subject will have received immune stimulatory therapy, such as cytokine treatment with IL-2 and GM-CSF prior to the isolation of lymphocytes. After one or more cycles of in vitro stimulation with PTH-rP peptide-pulsed dendritic or antigen presenting cells, the activated T cells can be reinfused into the patient to generate an immune response against the PTH-rP expressing tumor or metastases.

The invention encompasses those nucleic acid sequences which code for a PTH-rP peptide or variant thereof. This includes nucleic acid sequences which include alternative codons that encode the same amino acid residues of the PTH-rP peptides. For example, leucine residues can be encoded by the codons CUA, CUC, CUG, CUU, UUA and UUG. Due to the degeneracy of the genetic code each of the preceding six codons is equivalent for the purposes of encoding a leucine residue. Thus, it will be apparent to one of ordinary skill in the art that any of the leucine-encoding nucleotide triplets may be employed to direct protein synthesis, protocols for which may be found in Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York.

The present invention also embraces fusion proteins comprising all or part of a PTH-rP peptide amino acid sequence, such as oligoepitopes or multiepitope peptides. The PTH-rP peptides can be covalently linked, e.g. via polymerization or conjugation. In a preferred embodiment, the PTH-rP multi-epitope peptides are constructed from the sequential arrangement of PTH-rP peptide amino acid sequences. For example, a multiepitope peptide sequence can contain at least two or more of the following sequences: SEQ ID NO:2, SEQ ID NO:3, SEQ ID NO:4, and SEQ ID NO:5 in any orientation or order, including nested or overlapping arrangements. The PTH-rP peptides in the multiepitope peptide can be identical or different. In addition, the multi-epitope PTH-rP peptides may be fusion proteins including one or more PTH-rP peptides and one or more unrelated amino acid sequences. For example, the multiepitope peptides can include universal T helper peptide amino acid sequences, in flanking, nested, or overlapping arrangements. Universal T helper epitopes are well known in the art and may be derived from HBV core antigen (SEQ ID NO: 6) tetanus toxoid, pseudomonas aeruginosa toxin A, beta-galactosidase, brucella abortus, keyhole limpet hemocyanin, influenza virus hemagglutinin and nucleoprotein, hepatitis B core and surface antigens, malaria circumsporozoite, ovalbumin, etc. Alternatively, or additionally, T helper motifs such as those described in O'Sullivan et al., J. Immunol. 147:2663-2669, 1991, may be included. Such multiepitope peptides are expected to exhibit increased immunogenicity by a variety of mechanisms, one of which is their processing into several epitopes which are recognized by multiple branches of the immune system for the generation of enhanced immune responses. Examples of multiepitope peptides can be found in Thomson et al., Proc. Natl. Acad Sci. USA 92:5845-5849, 1995; Heiser et al., J. Immunol. 164: 5508-5514, 2000 and Gilbert et al., Nature Biotechnol. 15:1280-1284, 1997, while universal, promiscuous, or multifunctional T cell epitopes are described in Calvo-Calle et al., J. Immunol. 159: 1362, 1997; Takeshita et al., J. Immunol. 154: 1973-1986; and Carreno et al., J. Immunol. 148: 894-899, 1992, among many other references known to those skilled in the art. Thus, multiepitopic PTH-rP peptides containing various numbers and combinations of epitopes can be prepared and tested for recognition by CTLs and for efficacy in increasing an immune response. By administering PTH-rP peptides which bind MHC class I and class II molecules an improved immune response may be provided by inducing both T helper cells and T killer cells.

In a preferred embodiment, the PTH-rP peptides can be expressed from the nucleic acid sequences encoding them by suitable delivery vectors, such as attenuated viral vectors (e.g. vaccinia, fowlpox, adenovirus and many others known in the art). In a more preferred embodiment the invention provides for compositions comprising the PTH-rP peptides and immunostimulatory reconstituted influenza virosomes (IRIVs). Virosomes are modified liposomes that contain reconstituted fusion-active viral envelope proteins anchored in the phospholipid bilayer. The PTH-rP peptides can be crosslinked to the surface of virosomes, or they can be encapsulated by the virosomes. The PTH-rP peptides of the invention, including subsequences of SEQ ID NO:1, particularly SEQ ID NO: 2, SEQ ID NO: 3, SEQ ID NO:4 and SEQ ID NO: 5, or any combination thereof, including combinations of two or more PTH-rP, such as mixtures of the different PTH-rP peptides, including the multiepitopic peptides with or without universal helper epitopes can be efficiently attached to the virosome surfaces. Alternatively, the PTH-rP peptides, including combinations of different PTH-rP peptides can be encapsulated into the virosomes. These PTH-rP peptide loaded virosomes can be injected into the subject via intradermal, subcutaneous or other suitable routes analogous to the administration of the PTH-rP peptides described previously, including the multiepitopic PTH-rP peptides with universal T cell epitopes, and functional variants described above. Delivery of peptide-loaded virosomes provides immunotherapeutic advantages, such as access to the peptides by antigen presenting or dendritic cells in more particulate form, sustained release from a subcutaneous depot site, and potentiated immunogenicity due to influenza priming, and thus the virosomes facilitate incorporation of the PTH-rP peptides into antigen presenting cells in vivo.

In a further preferred embodiment the invention provides influenza virosomes encapsulating PTH-rP plasmids which elicit a multi-epitopic T cell-mediated immune response with cytotoxic activity to cancer cells that produce PTH-rP. The nucleic acid coding sequence of the PTH-rP plasmids can comprise SEQ ID NO:9 or code for the amino acid sequences of SEQ ID NO: 1, or subsequences thereof, including SEQ ID NO: 2, SEQ ID NO: 3, SEQ ID NO:4, and SEQ ID NO: 5, or any combination thereof, including multiepitopic peptides with universal helper epitopes operably linked to a promoter. As used herein, a coding sequence and regulatory sequences are said to be "operably" linked when they are covalently joined so as to place the expression or transcription of the coding sequence under the influence or control of the regulatory sequences such that the resulting transcript is translated into the desired protein or peptide. In addition to a promoter, the regulatory sequences may include 5' non-transcribed and 5' non-translated sequences involved in the initiation of transcription and translation respectively, such as a TATA box, capping sequence, or CAAT sequence, as well as enhancer sequences or upstream activator sequences. The plasmids used as part of the invention may optionally include 5' leader or signal sequences. The construction of plasmids encoding the PTH-rP peptides of the invention is routine to one of ordinary skill in the art, and suitable expression plasmids are commercially available. Encapsulation of nucleic acids such as into virosomes has been described, for example, in Waelti and Glueck, Int. J. Cancer: 77, 728-733, 1998.

In a preferred embodiment, the invention provides kits which allow the artisan to prepare a desired immunotherapeutic regimen. An example of a kit comprises any of the PTH-rP peptides of the invention, as well as multiepitopic PTH-rP fusion peptides including universal T cell epitopes and the functional variants previously discussed. The kit may also comprise virosomes loaded with the PTH-rP peptides of the invention, either by encapsulation or by surface-crosslinking. The kit may also include virosomes loaded with the nucleic acids coding for the PTH-rP peptides of the invention operably linked to regulatory sequences as previously described. The kit preferably includes instructions for use of the compositions. Other components may be added to the kits, as desired.

In another preferred embodiment, the invention provides a method of generating T cells that specifically recognize and lyse, directly or indirectly, tumor cells expressing PTH-rP. In a related aspect, a method of inducing an immune response against tumors and metastases expressing PTH-rP is provided. In a preferred aspect of the invention, a method of producing the regression of tumors and metastases is provided. A further preferred embodiment of the invention is the vaccination of a subject with the PTH-rP peptides and/or any of the compositions previously described to prevent the occurrence or recurrence of tumors and/or metastases that express PTH-rP.

The immune response generated or enhanced by any of the methods described herein can be monitored by various methods known in the art. For example, the presence of T cells specific for a given antigen can be detected by direct labeling of T cell receptors with soluble fluorogenic MHC molecule tetramers which present the antigenic peptide (Altman et al., Science 274:94-96, 1996; Dunbar et al., Curr. Biol. 8:413-416, 1998). The tetramers bind CTLs which recognize the peptide antigen/MHC class I complex. Cells bound by the tetramers can be sorted by fluorescence activated cell sorting to isolate the reactive CTLs. Thus tetramers can be used to monitor both $CD4^+$ and $CD8^+$ cell responses to vaccination protocols. Additional assay systems, including but not limited to measuring efficacy of cytotoxic T cell generation and measuring efficacy of immunoglobulin from B cells, may be used to monitor responses and are known to those skilled in the art.

The present invention also provides for the administration of the PTH-rP peptides in a suitable pharmaceutical formulation. By administration or administering is meant providing one or more peptides or peptide-containing compositions of the invention as a drug, prodrug, or a drug-metabolite, to an individual in need of treatment or prevention of a PTH-rP expressing malignancy. Such a drug which contains one or more of the PTH-rP peptides and/or peptide containing compositions of the present invention, as the principal or member active ingredient, for use in the treatment or prevention of PTH-rP expressing malignancies, can be administered in a wide variety of therapeutic dosage forms in the conventional vehicles for topical, oral, systemic, local, and parenteral administration. Thus, the invention provides compositions for parenteral administration which comprise a solution of the PTH-rP peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others. Thus, a typical pharmaceutical composition for intradermal infusion could be made up to contain 250 ml of sterile Ringer's solution, and 100 mg of peptide. Actual methods for preparing parenterally administrable compounds will be known or apparent to those skilled in the art and are described in more detail in for example, Remington: The Science and Practice of Pharmacy ("Remington's Pharmaceutical Sciences") Gennaro A R ed. $20^{th}$ edition, 2000: Williams & Wilkins PA, USA, which is incorporated herein by reference.

The route and regimen of administration will vary depending upon the stage or severity of the PTH-rP expressing cancer to be treated, and is to be determined by the skilled practitioner. For example, the peptides and peptide-containing compositions can be administered in such oral dosage forms for example as tablets, capsules (each including timed release and sustained release formulations), pills, powders, granules, elixirs, tinctures, solutions, suspensions, syrups and emulsions, or by injection. Similarly, they may also be administered in intravenous (either by bolus or infusion methods), intraperitoneal, subcutaneous, topical with or without occlusion, or intramuscular form. In preferred embodiments, the peptides and peptide-containing compositions are administered intradermally or subcutaneously. All of these forms are well known to those of ordinary skill in the pharmaceutical arts.

The daily dose of the PTH-rP peptides and compositions of the invention may be varied over a range from 0.001 to 1,000 mg per adult per day. For oral administration, the compositions are preferably provided in the form of tables containing from 0.001 to 1,000 mg, preferably 0.001, 0.01, 0.05, 0.1, 0.5, 1.0, 2.5, 10.0, 20.0, 50.0, 100.0 milligrams of active ingredient for the symptomatic adjustment of dosage according to signs and symptoms of the patient in the course of treatment. An effective amount of drug is ordinarily supplied at a dosage level of from about 0.0001 mg/kg to about 50 mg/kg of body weight per day. The range is more particular from about 0.0001 mg/kg to 7 mg/kg of body weight per day.

Advantageously, suitable formulations of the present invention may be administered in a single daily dose, or the total daily dosage may be administered in divided doses for example of two, three, or four times daily. The PTH-rP peptides and compositions of the present invention may be used to prepare a medicament or agent useful for the treatment of PTH-rP expressing tumors or metastases. Furthermore, compounds of the present invention, particularly those containing virosomes or liposomes, can be administered in intranasal form, or via transdermal routes known to those of ordinary skill in the art. To be administered in the form of a transdermal delivery system, the dosage administration will, or course, be continuous rather than intermittent throughout the dosage regimen.

For treatment and prevention of PTH-rP expressing cancers and/or metastases, the PTH-rP peptides of the present invention may be administered in a pharmaceutical composition comprising the active compound in combination with a pharmaceutically acceptable carried adopted for topical administration. Topical pharmaceutical compositions may be, for example, in the form of a solution, cream, ointment, gel, lotion, shampoo, or aerosol formulation adapted for application to the skin. These topical pharmaceutical composition containing the compounds of the present invention ordinarily include about 0.005% to 5% by weight of the active compound in admixture with a pharmaceutically acceptable vehicle.

For the treatment and prevention of PTH-rP expressing tumors and metastases the PTH-rP peptides and compositions of the present invention may be used together with other agents known to be useful in treating such malignancies. For combination treatment with more than one active agent, where the active agents can be administered concurrently, the active agents can be administered concurrently, or they can be administered separately at staggered times.

The dosage regimen utilizing the compositions of the present invention is selected in accordance with a variety of factors, including for example type, species, age, weight, sex and medical condition of the patient, the stage and severity of the PTH-rP expressing malignancy, and the particular compound thereof employed. A physician of ordinary skill can readily determine and prescribe the effective amount of the drug required to prevent, counter, or arrest the progress of the malignancy. Optimal precision in achieving concentration of drug with the range that yields efficacy either without toxicity or with acceptable toxicity requires a regimen based on the kinetics of the drug's availability to target sites. This process involves a consideration of the distribution, equilibrium, and elimination of the drug, and is within the ability of the skilled practitioner.

In the methods of the present invention, the compounds herein described in detail can form the active ingredient and are typically administered in admixture with suitable pharmaceutical diluents or excipients suitably selected with respect to the intended form of administration, that is, oral tablets, capsules, elixirs, syrups, and the like, and consistent with conventional pharmaceutical practices. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, aga, bentonite, xanthan gum and the like.

The liquid forms may be suitably flavored suspending or dispersing agents such as the synthetic and natural gums, for example, tragacanth, acacia, methyl cellulose and the like. Other dispersing agents which may be employed are glycerin and the like. For parenteral administration, sterile suspensions and solutions are desired. Isotonic preparations which generally contain suitable preservatives are employed when intravenous administration is desired. Topical preparations containing the active drug component can be admixed with a variety of carrier materials well known in the art, such as, for example, alcohols, aloe vera gel, allatoin, glycerine, vitamins A or E oil, mineral oil, PPG2 myristyl propionate, and the like, to form, for example, alcoholic solutions, topical cleansers, cleansing creams, skin gels, skin lotions, and shampoos in cream or gel formulations.

The PTH-rP peptides or formulation thereof of the present invention may be coupled to a class of biodegradable polymers useful in achieving controlled release of a drug, for example, polylactic acid, polyepsilon caprolactone, polyhydroxy butyric acid, polyorthoesters, polyacetals, polydihyrdo-pyrans, polycyanoacrylates, and cross-linked or amphipathic block copolymers of hydrogels. Generally, subjects can receive an intradermal injection of an effective amount of the PTH-rP peptides either in combination with delivery vectors, such as virosomes, or by themselves. The PTH-rP peptides of the present invention can also be administered in the form of liposome delivery systems, such as small unilamellar vesicles, large unilameller vesicles and multilamellar vesicles. Liposomes can be formed from a variety of compounds, including for example cholesterol, stearylamine, and various phosphatidylcholines.

Initial doses can be followed by booster doses, following immunization protocols standard in the art. The immunostimulatory effect of the compositions and methods of the instant invention can be further increased by combining any of the above-mentioned PTH-rP peptide compositions, including their combination with virosomes, with an immune response potentiating compound. Immune response potentiating compounds are classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include Freund's, alum, mycobacteria such as BCG and M. Vaccae, quilsaponin mixtures such as QS-21 (SmithKline Beecham) and various oil/water emulsions (e.g. IDEC-AF). Cytokines are also useful in vaccination protocols as a result of lymphocyte stimulatory properties. Many cytokines useful for such purposes will be known to one of ordinary skill in the art, including interleukin-2 (IL-2), IL-12, GM-CSF and many others.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The preparations of the invention are administered in effective amounts. An effective amount is that amount of a pharmaceutical preparation that alone, or together with further doses, stimulates the desired response. Generally, doses of immunogens ranging from one nanogram/kilogram to 100 miligrams/kilogram, depending upon the mode of administration, are considered effective. The preferred range is believed to be between 500 nanograms and 500 micrograms per kilogram. The absolute amount will depend upon a variety of factors, including the composition selected for administration, whether the administration is in single or multiple doses, and individual patient parameters including age, physical condition, size, weight, and the stage of the disease. These factors are well known to those of ordinary skill in the art and can be addressed with no more than routine experimentation.

In the case of treating cancer, the desired response is inhibiting the progression of the cancer and/or inducing the regression of the cancer and its metastases. These desired responses can be monitored by routine methods or can be monitored according to diagnostic methods of the invention discussed herein. The present invention is not to be limited in scope by the specific embodiments described herein. Indeed, various modifications of the invention in addition to those described herein will become apparent to those skilled in the art from the foregoing description, as well as from the examples. Such modifications are intended to fall within the scope of the appended claims.

EXAMPLES

The following examples are provided to better illustrate the claimed invention and are not to be interpreted as limiting the scope of the invention. To the extent that specific materials are mentioned, it is merely for purposes of illustration and is not intended to limit the invention. Unless otherwise specified, general cloning procedures, such as those set forth in Sambrook et al., Molecular Cloning, Cold Spring Harbor Laboratory (2001), Ausubel et al. (Eds.) Current Protocols in Molecular Biology, John Wiley & Sons (2000) are used. One skilled in the art may develop equivalent means or reactants without the exercise of inventive capacity and without departing from the scope of the invention.

Example 1

This example establishes that influenza virosomes encapsulating PTH-rP plasmids are capable of eliciting a multi-epitopic T cell-mediated immune response with cytotoxic activity to cancer cells that produce PTH-rP. The results show that virosomes are suitable vectors capable of directly transferring genes or proteins to antigen-presenting cells, thereby stimulating efficient immune responses against the PTH-rP expressing tumor cells. The virosomes efficiently infect human dendritic cells which present the tumor antigen peptides to T cell precursors, thereby initiating a squalor antigen-specific immune response. Virosomes can be administered in a variety of ways, including intranasally, and are a good delivery system for inducing PTH-rP specific effector T cells capable of recognizing PTH-rP expressed by tumor cells.

Cell cultures: The LNCaP and DU-145 prostate carcinoma cell lines, the SW1463 colon carcinoma cell line and VERO cell lines were purchased from the American Type Culture Collection (Rockville, Md.) and cultured as suggested by the provider in complete medium Roswell Park Memorial Institute (RPMI)-1640 with 10% fetal bovine serum (FBS), 2 mM L-glutamine (all purchased by Gibco Corp.). Dr. Jeffry Schlom (National Cancer Institute, National Institutes of Health, Bethesda, Md., USA) kindly provided the CIR-A2 cell line, and Dr. A. Castrucci (National Institute of Health, Rome, Italy) the P815 murine mastocytic leukemia cell line. Both cell lines were cultured in the same medium described above.

Generation of a PTH-rP plasmid and influenza virosomes: The PTH-rP gene was amplified from the DU 145 prostate carcinoma cell line by means of reverse transcriptase-polymerase chain reaction (RT-PCR), (Cusi et al., *Biotechniques* 1994,17, 1034-1036), starting from the specific mRNA by using the sense primer 5'TTGGATCCATGCAGCGGAGACTGGTT3' (SEQ ID NO: 7) and the antisense primer 5'CCGAATTCTCAATGCCTCCGTGAATCGA3' (SEQ ID NO: 8), and cloned in BamHI-EcoRI sites of the pcDNA3 expression vector (InVitrogen) in order to obtain the recombinant plasmid GC90. The construct was grown in DH5α cells. Plasmid DNA was purified using the Qiagen Endo Free plasmid kit (QIAGEN) as described by the manufacturer. The influenza virosomes were prepared as follows: hemagglutinin (HA) from the A/Singapore/6/86 strain of influenza virus was isolated as described by Skehel and Schild (1971). Virus was grown in the allontoic cavity of hen eggs, and was purified twice by ultracentrifugation in a sucrose gradient. Purified virus was stabilized in a buffer containing 7.9 mg NaCl/ml, 4.4 mg/ml trisodiumcitrate.2H$_2$O/ml, 2.1 mg 2-morpholinoethane sulfonic acid/ml, and 1.2 mg N-hydroxyethyl-piperazine-N'-2-ethane sulfonic acid/ml, pH 7.3. Virus suspension (53 ml) containing 345 μg HA per ml was pelleted by ultracentrifugation at 100,000 g for 10 minutes, and 7.7 ml of a buffered detergent solution containing 145 mM NaCl, 2.5 mM HEPES, and 54 mg/ml of C12E8, pH 7.4 were added to the pellet. Then the pellet was completely dissolved by ultrasonication for 1 to 2 min at room temperature, the resulting solution being subjected to ultracentrifugation at 100,000 g for 1 hour. The supernatant contained the solubilized HA trimer (1.635 mg HA/ml) and trace amounts of neuraminidase. After 6 mg of DOTAP were added to 3.7 ml of supernatant (6 mg HA) and dissolved, the solution was sterilized by passage through a 0.2-μm filter and transferred to a glass container containing 1.15 g of sterile Biobeads SM-2. The container was shaken for 1 hr by a REAX2 shaker (Heidolph, Kelheim, Germany). This procedure was repeated 3 times with 0.58 mg of biobeads, after which a slightly transparent solution of DOTAP virosomes was obtained. Non-encapsulated plasmids were separated by 0.1 gel filtration on a High Load Superdex 200 column (Pharmacia) equilibrated with sterile phosphate-buffered solution (PBS). The void volume fractions containing the virosomes and encapsulated plasmids were eluted with PBS and collected.

Cell transfection: Approximately $10^5$ target cells (Vero, P815 or CIR-A2 cells) were grown in 6-well microplates at 37° C. and infected with 0.3 μg of DNA virosomes or transfected with 1 μg of plasmid DNA using the Effectene Transfection reagent (QIAGEN) as described by the manufacturer. After two days, PTH-rP antigen expression was analyzed by Briefly, the cells were washed twice with PBS, fixed with cold methanol/acetone and treated with a rabbit anti-PTH-rP serum (Calbiochem) followed by FITC-conjugated goat anti-rabbit IgG (1/100) (DBA Italia SRL, Milan, Italy). The coverslips were mounted on slides and examined using a Diaplan microscope (Leitz).

Generation of DC and T cell lines: Peripheral blood mononuclear cells (PBMC) were isolated from heparinised blood derived from an HLA-A2$^+$ male normal volunteer using a lymphocyte separation gradient medium (Organon Tecknika, N.C.) as previously described [Boyum, *Scand J Clin Lab Invest* 1968, 97 (suppl), 51-76)].

Dendritic cells. DC enrichment was performed using PBMCs as previously described (Bell et al., *Adv Immunol* 1999, 72, 255-324). After seven days culture in a medium containing 25 ng/ml of granulocyte macrophage-colony stimulating factor (GM-C SF) (Schering-Plough Corp.) and 5 ng/ml of interleukin-4 (IL-4) (R & D Corp.), direct immunofluorescence flow cytometry revealed a DC phenotype with the expression of CD1a, HLA-I, HLA-DR, CD11c, CD80, CD83 and CD86.

T cell lines. The PBMCs for CTL primary cultures were suspended in AIM-V medium (Life Technologies, Inc.) supplemented with 5% pooled human AB serum (Valley Biomedical, Winchester, Va.), 2 mM L-glutamine and 100 U/ml penicillin/streptomycin (Gibco). Each well of a 96-well microplate (Corning, Costar Corp. Cambridge, Mass., USA) was seeded with $2\times10^5$ cells in a volume of 100 µl. The autologous DCs were first infected with 300 ng of GC90 virosomes and, after 48 hours of culture at 37° C. and 5% $CO_2$, they were irradiated (5000 R) and added to the lymphocyte cultures at a final ratio of 1:5. One in vitro stimulation cycle (IVS) was designed as a 5-day period of cell incubation with antigen-loaded DC plus a 10-day period of cell stimulation with 50 IU of IL-2 (Cetus Corp.). The medium was replaced by cytokine-containing fresh complete medium every 48 hours. On the $16^{th}$ day, the T cell cultures were re-stimulated with autologous irradiated DCs infected with the GC90 virosomes used as antigen-presenting cells.

PTR-2 and PTR-4 peptides: The PTR-2 and PTR-4 peptides (whose amino acid sequences are FLHHLIAEIH (SEQ ID NO: 3) and TSTTSLELD (SEQ ID NO: 5), respectively) were synthesised using a solid phase automatic peptide synthesizer (Model Syto, MultiSyntech, Witten, Germany) and the fluorenylmethoxycarbonyl (Fmoc)/diisopropylcarbodiimide (DIC)/1-hydroxybenzotriazole (HOBT) strategy. The peptides were cleaved from the resins and defracted by treatment with trifluoroacetic acid containing ethandiethiol, water trisbuthyl silone and anisole (93/2.5/2/1.5/1). The crude peptides were purified by means of high performance liquid chromatography (HPLC) using a Vydac C18 column (25 cm×1 cm, 10 µm). The products were dissolved in bi-distilled water, sterile filtered and frozen at −70° C. at a concentration of 2 mg/ml. HPLC showed that the purity of the peptides was more than 90%. The carcino-embryonic antigen peptide (CAP)-1 control peptide was kindly provided by Dr. J. Schlom (EOS, NCI, Bethesda, Md., USA).

Cytotoxic assays: Various target cells were labelled with 50 µCi of $^{51}$[Cr]-isoquinoline (Medi Physics Inc., Arlington, Ill.) for 60 minutes at room temperature. The target cells ($0.5\times10^4$) were added to each of the wells of 96-well microplates in 100 µl of complete RPMI-1640. The labelled targets were incubated at 37° C. in 5% $CO_2$ before adding effector cells at different E:T ratios. The T cells were then suspended in 100 µl of AIM-V medium and added to the target cells. The plates were incubated at 37° C. for six hours, and 100 µl of the supernatant of each sample was harvested for γ-counting. The determinations were carried out in triplicate and standard deviations were calculated. All of the experiments were repeated at least three times. Specific lysis was calculated as follows:

$$\text{Specific lysis \%} = \frac{\text{Observed release (cpm)} - \text{spontaneous release (cpm)}}{\text{Total release (cpm)} - \text{spontaneous release (cpm)}} \times 100$$

Spontaneous release was determined from wells to which 100 µl of complete medium were added instead of effector cells. Total releasable radioactivity was measured after treating the target with 2.5% Triton X-100.

For the HLA blocking experiments, the UPC-10 control mAb (Cappel/Organon Technique Corp., West Chester, Pa., USA) or anti-HLA-A2 mAb (A2.69, #189HA-1; One Lambda, Inc., Canoga Park, Calif., USA) were added to the $^{51}$[Cr] loaded target cells (LNCaP) and incubated for one hour before the cytotoxic assay.

Flow cytometry: The procedure for single-colour flow cytometric analysis has been previously described (Guadagni et al., *Cancer Res* 1990, 50, 6248-6255), and is the same as that used for dual-color flow cytometry. The cells were analysed using a Becton Dickinson FACScan equipped with a blue laser with excitation of 15 nW at 488 nm. The data gathered from 10,000 live cells were used to evaluate the results. The PBMCs were HLA phenotyped by the Blood Bank of the Azienda Ospedaliera Senese, Policlinico "Le Scotte", Siena, Italy, using a standard antibody-dependent micro-cytotoxicity assay and a defined panel of anti-HLA antisera for HLA class I determinations.

Statistical analysis: The differences between the means were statistically analysed using Stat View statistical software (Abacus Concepts, Berkeley, Calif., USA). The results are expressed as the mean values of four determinations from three different experiments±standard deviation. The differences between the means were determined using the two-tailed Student t-test for paired samples, and considered statistically significant at a P value of <0.05.

Mouse immunization: Four-week-old female BALB/c mice (Charles River) were anesthetised with ketamine-xylazine and immunized by means of the intranasal instillation of 5 µg of DNA associated with influenza virosomes/mouse in a volume of 20 µl, thus ensuring deposition of the inoculum throughout the respiratory tract. Six mice in each group were immunized with the GC90-virosome complex (group A), pcDNA3 virosomes (group B), GC90 virosomes plus the subcutaneous administration of IL-2 100 IU/day for five days a week (group C), or pcDNA3 virosomes plus IL-2 (group D). Boosters were given three and five weeks after primary immunization. The mice were sacrificed by cervical dislocation under anesthetic ten days after the last immunization, their spleens were harvested, and the spleen cells cultured in the presence of 100 IU of IL-2 for seven days before being examined for PTH-rP specific CTL activity. Each experiment was repeated three times to ensure the reproducibility of the results.

Generation of a PTH-rP DNA plasmid virosome: A PTH-rP DNA plasmid virosome (GC90V) was generated according to the procedures outlined above. Its ability to infect human (CIR-A2) and murine target cells (P815) by inducing the in vitro expression of PTH-rP was demonstrated by means of immunoradiometric assay, the RT-PCR detection of specific mRNA, and immunofluorescence using a rabbit anti-PTH-rP serum (data not shown). The same techniques were used to demonstrate the ability of the GC90 plasmid used for target cell transfection to induce the transient expression of PTH-rP in the CTL target cells in the cytotoxic assays.

Immunological and toxicological effects of GC90V in a mouse model: The immunological and toxicological effects of intranasally instilled virosome/PTH-rP plasmid GC90V in BALB/c mice was tested in the presence or absence of IL-2. The mice were divided into four groups of six animals. Cytotoxic assays based on 6-hour $^{51}$Cr release revealed significant cytotoxic activity against P815 target cells transfected with PTH-rP plasmids in the spleen cells from the mice of groups A and C (FIG. $1^a$). Target cell lysis was MHC-class I restricted, since CTL activity was abrogated by the addition of anti-H2$^{kd}$ (FIG. $1^b$). The finding that group C spleen cells had the most efficient cytotoxic activity suggests that IL-2 treatment enhances the immunological activity of GC90V. PTH-rP-specific cytotoxic activity in this experiments was mediated by the CD8+ cell population because the addition of an anti-mouse mAb against CD8 almost completely abrogated spleen cell cytotoxic activity against PTH-rP-transfected P815 target cells (FIG. $1^d$), but the addition of an anti-CD19 negative control antibody did not affect CTL activity (data not shown).

No cytotoxic activity was detected against untransfected parental P815 cells (data not shown) or the cells transfected with the plasmid backbone pcDNA3 (FIG. $1^c$). The spleen cells from groups B and D did not lyse any of the target cells (FIG. 1 as a whole). The differences of values of the groups A (GC90V) and C (GC90V+IL-2) respectively compared with those of the groups B (pcDNA-3) and D (pc-DNA-3+ IL-2) were statistically significant (P<0.05) at E:T ratios of 6.25, 12.5 and 25:1.

Autoptic pathology: examination of the mice who had received influenza virosomes including PTH-rP plasmids±IL-2 did not reveal the occurrence of any toxic or auto-immune reactions (data not shown). The organs and tissues in which parathyroid hormone (parathyroid glands) or low levels of PTH-rP (skin, breast, brain, the first tract of the airway-digestive mucosa) can be detected were examined for the presence of lymphocyte infiltration, necrosis or apoptosis, but no differences were found in comparison with those taken from the control mice. PTH and PTH-rP target tissues (bone and kidneys) were also investigated and showed no anomalies. Since PTH and PTH-rP act on calcium phosphate turnover, ionized calcium and phosphate levels were investigated in all of the sera samples, but were in the normal ranges during treatment. On the basis of these results, it can be concluded that the influenza virosome delivery system is safe and induces a good antigen specific cellular response in animal models especially when combined with IL-2. It also has the additional advantage of using very small amounts (5 μg) of TAA gene-specific DNA that can be administered intranasally.

Generation of a human PTH-rP-specific CTL response in PBMCs stimulated in vitro with GC90V infected autologous dendritic cells: The system was also tested in human models in vitro with the aim of eliciting a PTH-rP-specific CTL response because preliminary laboratory data had shown that GC90V can infect human DCs in vitro by inducing PTH-rP production. The DCs used in this study were generated from PBMCs isolated from an HLA-A2.1$^+$ healthy donor, and cultured in the presence of GM-CSF and IL-4. Direct immunoflorescence flow cytometry revealed that they expressed CD1a (20%), CD40 (31.95%), CD11c (87.25%), CD80 (22%), CD83 (35%), CD86 (99.59%), HLA-class IA, B, C (99.65%), and HLA-Dr (99.8%). A human PTH-rP-specific CTL line could be generated in vitro by means of the cyclical stimulation of normal HLA-A2.1$^+$ donor PBMCs with GC90 virosome-infected autologous DCs.

Figure 2:
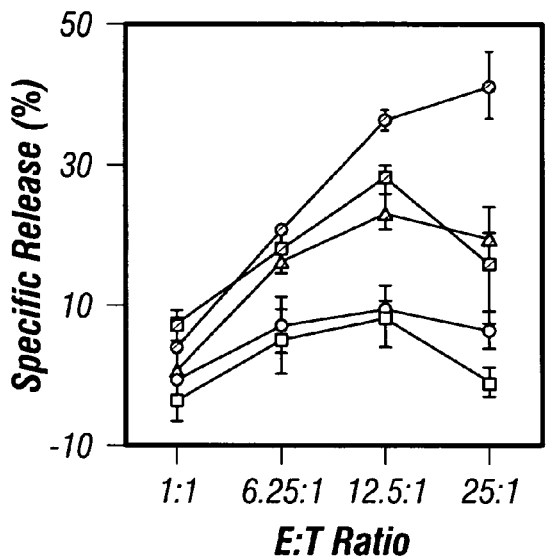
FIG. 2: this figure shows the PTH-rP specific cytolytic activity of a human cytotoxic T cell line generated in vitro with low dose IL-2 and GC90-virosome infected dendritic cells against different target cells. The figure shows CTL activity against HLA-A2.1$^+$ CIR-A2 cells (○), CIR-A2 cells pulsed with 25 µg/ml of PTH-rP (PTR-4) peptide (▲), CIR-A2 cells pulsed with 25 µg/ml of PTH-rP (PTR-2) peptide (■), CIR-A2 cells transfected with pcDNA3 (□), and CIR-A2 cells transfected with PTH-rP plasmid (GC90) (●). The data are from three different experiments with similar results. The differences between the values of the PTH-rP peptide pulsed- and PTH-rP transfected-CIR-A2 cells respectively compared with the values of the unpulsed CIR-A2 and pcDNA3-trasfected CIR-A2 cells were statistically significant (P<0.05).
Figure 3:
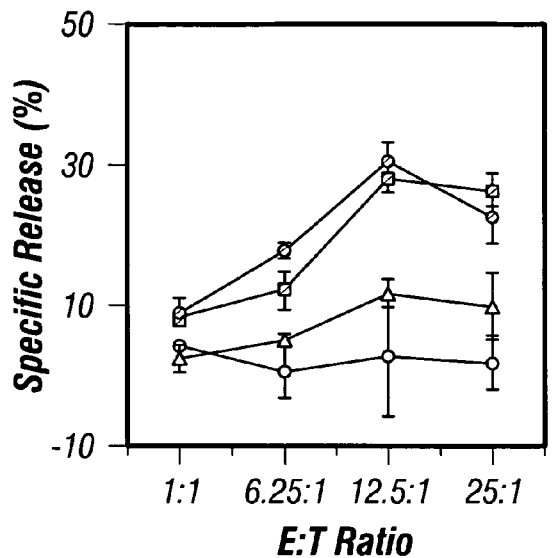
FIG. 3: this figure shows human CTL activity against HLA-A2.1+/PTH-rP+ prostate carcinoma LNCaP cells ( ), LNCaP cells in the presence of anti-HLA-A2.1 mAb (dilution 1:100) (Δ), LNCaP cells in the presence of a control isotype mAb (UPC-10) (■), and HLA-A2.1+/PTH-rP− colon carcinoma SW-1463 cells (○). The data are from three different experiments with similar results. The differences between the values of the LNCaP cells in the presence of A2.69 and SW-1463 cells rescpectively compared with the values of the LNCaP cells in the presence of MOPC-10 and LNCaP cells were statistically significant (P<0.05).

After four in vitro stimulations (two months of culture), the cell line showed a CD3$^+$ (95%), CD4$^-$/CD8$^+$ (75%), CD56$^-$ (5.8%) phenotype. Six-hour cytotoxic assays revealed that the T cell line was cytotoxic to class I matching (HLA-A2.1$^+$) target cells (CIR-A2) transfected with GC90 plasmid (FIG. 2). Cytotoxic T lymphocytes recognize protein antigens as 9-10 amino acid peptides derived from the antigen proteolysis of proteasomes in the cell cytoplasm, and bound to HLA molecules on the target cell membrane. The peptide binding to specific HLA isotypes is endorsed by the presence of specific amino acid sequences (HLA-binding amino acid consensus motifs). The human T cells stimulated with GC90V-infected DCs recognized multiple PTH-rP epitopes as they lysed the CIR-A2 target cells pulsed with PTR-2 or with PTR-4 (FIG. 2); the same cell line was also cytotoxic to HLA-A2.1$^+$ prostate carcinoma (LNCaP) cells, which produce large amounts of PTH-rP (FIG. 3). The CTL cytotoxic activity was HLA-class I (HLA-A2.1) restricted because it was abrogated by the addition of of the A2,69 mAb to the HLA-A2.1 molecules (FIG. 3). However, the cytotoxic T cells could not lyse peptide unpulsed CIR-A2 target cells, CIR-A2 cells transfected with pcDNA3 plasmid, CIR-A2 cells pulsed with PTH-rP-unrelated peptides with HLA-2.1 binding amino acid consensus motifs (data not shown) or SW1463 HLA-A2.1$^+$ colon carcinoma cells unable to produce PTH-rP (FIGS. 2 and 3). Before each cytotoxic experiment, PTH-rP production in the target cells was demonstrated by RT-PCR and radioimmunometric assays, and HLA-A2.1 expression by means of indirect immunofluorescence flow cytometry.

Example 2

This example demonstrates that PTH-rP peptide-pulsed dendritic cells can generate PTH-rP peptide specific T cells from lymphocytes infiltrating a prostate carcinoma bone metastatic lesion. Because tumors do not start de novo T cell mediated immune reaction, presumably because they lack the costimulatory signals necessary for T cell activation, antigen presenting cells and particularly dendritic cells are an important target for immunotherapeutic approaches to cancer. Antigen presenting cells efficiently take up, process and present antigens to T cell precursors and can start de novo T cell mediated immune responses against the tumor if they can be manipulated to present tumor associated antigenw, such as a PTH-rP peptide. As this example demonstrates, antigen presenting cells or dendritic cells presenting PTH-rP peptides can also generate T cells with antitumor activity from the tumor infiltrating lymphocytes isolated from subjects with advanced prostate cancer and bone metastases. The example shows that stimulation with PTH-rP peptides presented by denritic cells can restore the PTH-rP-specific anti-tumor cytotoxicity of these tumor-infiltrating lymphocytes against the autologous tumor cells expressing PTH-rP. Thus activated and expanded, the tumor infiltrated lymphocytes may be reinfused into the patient where they are expected to attack the tumor, leading to the regression of primary PTH-rP expressing tumors as well as their metastases.

Cell cultures: The prostate carcinoma LNCaP and the colon carcinoma SW1463 cell lines were purchased from American Type Culture Collection (Rockville, Md., USA). The cultures were mycoplasma free and were maintained in complete medium (Dulbecco's modified Eagle medium) [Life Technologies inc. (Gibco BRL) Grand Island, N.Y.]

supplemented with 10% heat inactivated fetal bovine serum (FBS), 2 mM glutamine, 100 U/ml penicillin, and 100 µg/ml streptomycin (Life Technologies, inc.). The CIR-A2 cell line was maintained in Iscove's modified Dulbecco's complete medium (IMDM).

Peptide Synthesis: Synthesis of PTR-4 peptides (amino acid sequence: TSTTSLELD, SEQ ID NO: 5) was performed on a solid phase automatic peptide synthesizer (model syto, MultiSyntech, Witten, D) using the Fluorenylmethoxycarbonyl (Fmoc)/Diisopropylcarbodiimide (DIC)/1-Hydroxybenzotriazole (HOBT) strategy. Peptides were cleaved from the resins and defracted by treatment with trifluoroacetic acid containing ethandiethiol, water trisbuthyl silone and anisole (93/2.5/2/1.5/1). The crude peptides were purified by HPLC using a Vydac C18 column (25 cm×1 cm, 10 µm). The products dissolved in bi-distilled water, sterile filtered and frozen at −70° C. at a concentration of 2 mg/ml. The purity of the peptides was more than 90% as analyzed by high-performance liquid chromatography (HPLC). The CAP-1 control peptide was kindly donated by Dr. J. Schlom.

TIL cell culture and expansion: Tissue obtained from biopsy samples of metastatic bone were mechanically fragmented and seeded in T25 (Corning, Costar Milano, Italia) dissolved in AIM-V medium supplemented with 5% pooled human heat inactivated AB serum (Valley Biomedical, Winchester, Va.), 2 mM glutamine, 100 U/ml penicillin, and 100 µg/ml of streptomycin (Flow, Irvine, UK), and containing 6,000 IU/ml recombinant IL-2 (Cetus Corp. Emeryville, Calif., USA). The cells were incubated at 37° C. and 5% $CO_2$. for 96 hours. The mononucleate cells were subsequently, separated using density gradients. The cell suspension obtained was cultured at the concentration of $1\times10^6$ cell/ml in 24 multiwell plates (Corning, Costar Milano, Italia) in the same IL-2 containing medium. One week later, the cells were evaluated for T cell immune phenotype and stimulated with peptide pulsed autologous DC as described above for PTH-rP peptide specific CTL lines.

Generation of DC and T Cell Lines: PBMC were isolated before, during and after treatment with GM-CSF and IL-2 from heparinized blood taken from a $HLA-A2^+$ male donor affected by advanced prostate carcinoma using a lymphocyte separation medium gradient (Celbio Biotecnologie S.R.L., Milano, Italia) as previously described [Boyum et al, 1968].

PBMC for DC enrichment ($10^7$ cell/ml) were seeded in T75 flasks in a 10 ml volume of complete medium (RPMI-1640) with 10% heat inactivated FBS. After 4 hours' incubation at 37° C. in 5% $CO_2$, the non-adherent cells were removed and adherent cells were maintained for seven days in complete medium (RPMI-1640 with 10% heat inactivated FBS, 2 mM glutamine, 100 U/ml penicillin, and 100 µg/ml streptomycin) containing 50 ng/ml of GM-CSF (Molgramostim, kindly furnished by the Shering Plough, S.P.A., Milano, Italia) and 0.5 ng/ml of IL-4 (purchased from the R and D systems, Minneapolis, Minn., USA). The medium containing GM-CSF and IL-4 was, replaced every 48 hours. After seven days of culture the DC phenotype cells was evaluated by means of direct immunofluorescence flow cytometry. In order to estimate the DC enrichment before CTL stimulation, the cultures were examined for the expression of CD1a, HLA-I, HLA-DR, CD11c, CD80, CD83, and CD86, which are markers known to be highly expressed by DC and involved in T cell costimulation and activation [Bell et al, 1999; Grabbe et al, 1995; Romani et al, 1995].

The TIL for CTL primary cultures, were washed and then resuspended in AIM-V medium (Life Technologies, S.R.L., Milano, Italia) supplemented with 5% pooled human heat inactivated AB serum (Valley Biomedical, Winchester, Va.), 2 mM glutamine, 100 U/ml penicillin, and 100 µg/ml of streptomycin (Gibco). The cells ($2\times10^5$) in a volume of 100 µl of complete medium were added to each well of a 96-well flat-bottom assay plate (Corning, Costar Milano, Italia).

Irradiated autologous DC were pulsed with PTR-4 peptides (25 µg/ml) and added to the lymphocyte cultures at the final ratio of 1:5. DC cultures were irradiated prior TIL or PBMC in vitro stimulation, in order to prevent the possibility that contaminating NK or T cells could proliferate in presence of TIL and cytokines, affecting the clonal expansion of PTH-rP peptide specific T cell clones.

Cultures were incubated for 5 days at 37° C. in a humidified atmosphere containing 5% $CO_2$, and then provided with human recombinant IL-2 (20 U/ml) for 11 days, with the IL-2-containing medium being replenished every 3 days. The incubation time of five days with peptide pulsed DC plus 10 days with IL-2 constitutes one in vitro stimulation cycle (IVS). The T cell cultures were re-stimulated with PTH-rP peptide (25 µg/ml) pulsed autologous DC on day 16. Irradiated (5,000 rads) autologous DC were added in a volume of 100 µl of complete medium (AIM-V) and used as antigen presenting cells.

The progenitor TIL cultures were maintained in AIM-V medium supplemented with 5% pooled human heat inactivated AB serum, 2 mM glutamine, 100 U/ml penicillin, and 100 µg/ml of streptomycin, and containing 20 IU/ml of IL-2. The TIL cultures were re-stimulated every 15 days with autologous irradiated DC cells plus autologous irradiated prostate cancer cells in a 5:1 ratio.

T cell lines: PBMC, for CTL primary cultures, were suspended in AIM-V medium (Life Technologies, inc.) supplemented with 5% pooled human heat inactivated AB serum (Valley Biomedical, Winchester, Va.), 2 mM L-glutamine, 100 U/ml penicillin/streptomycin (Gibco). $2\times10^5$ cells, in a volume of 100 µl, were seeded into each well of a 96-well microplate (Corning, Costar Corp. Cambridge, Mass.). Autologous DC were first irradiated (5000 R) and pulsed with 25 µg/ml of PTR-4 and then added to the lymphocyte cultures to the final ratio of 1:5. One in vitro stimulation cycle (IVS) was represented by a 5 day period of cell incubation with antigen loaded DC plus a 10 day period of cell stimulation with 50 IU of IL-2 (Cetus corp). Fresh complete medium containing cytokines was replaced every 48 hours. On the $16^{th}$ day, T cell cultures were re-stimulated with autologous irradiated DC pulsed with PTR-4 used as antigen presenting cells.

Culture and expansion of prostate cancer cells derived from bone metastases: The tissue obtained from metastatic bone samples, taken by bone biopsy, were mechanically fragmented and seeded in T25 flasks (Corning, Costar Milano, Italia) in RPMI medium supplemented with 5% pooled human heat inactivated AB serum, 2 mM glutamine, 100 U/ml penicillin, and 100 µg/ml of streptomycin, and containing 100 IU of human recombinant Insulin (Sigma-Aldrich, S.R.L., Milano, Italia) and $10^{-8}$M androstenedione (Sigma-Aldrich, S.R.L., Milano, Italia). The cells were incubated at 37° C. and 5% $CO_2$ for six weeks with the medium being replenished every week. Adherent cells with epithelial cell features appeared evident after 2 weeks of culture. After six weeks cells were studied by a pathologist and immunohistochemically analyzed for the expression of cytokeratines and PSA.

Immunohistochemistry: The slides containing the cultured cells, were fixed in cold acetone for 10 minutes, and were incubated with anti-human PSA mouse monoclonal antibody (Immunotech, Marseille, France) diluted 1:500 in TBS; then the reaction was revealed using streptoavidin-biotin complex. Slides were weakly counterstained with Harris' hematoxilin, mounted with aqueous mounting medium and examined under a light microscope. Negative controls were obtained for each case by replacing the specific antibody with non immune serum immunoglobulin at the same concentration as the primary antibody. Immunereactivity was assessed using routine light microscopy.

Target cell transfection with PTH-rP plasmid: The PTH-rP gene was amplified from the prostate carcinoma DU-145 cell line by RT-PCR and cloned in the BamHI-EcoRI sites of the pcDNA3 expression vector (InVitrogen) in order to obtain the recombinant plasmid GC90. The construct was grown in DH5 cells. Plasmid DNA was purified using the Qiagen Endo Free plasmid kit (QIAGEN) as described by the manufacturer. Approximately $10^5$ CIR-A2 target cells were grown in 6 well microplates at 37° C. transfected with 1 µg of plasmid DNA using the Effectene Transfection reagent (QIAGEN) as described by the manufacturer. After two days, PTH-rP antigen expression was analyzed by evaluating the presence of the specific mRNA by RT-PCR and by immunofluorescence. Briefly, the cells were washed twice with PBS, fixed with cold methanol/acetone and treated with a rabbit anti-PTH-rP serum (Calbiochem) followed by FITC-conjugated goat anti-rabbit IgG (1/100) (DBA). The coverslips were mounted on slides and examined using a Diaplan microscope (Leitz).

Cytotoxic assays: Various target cells were labeled with 100 µCi of $Na_2Cr^{51}O_4$ (Amersham, Aylesbury, UK) for 60 minutes at room temperature. Target cells ($0.5 \times 10^4$) in 100 µl of complete medium (see below) were added to each of 96 wells in T-flat bottom assay plates (Corning Costar Italia, Milano). The labeled targets were incubated at 37° C. in 5% $CO_2$ before adding effector cells. The T cells were then suspended in 100 µl of AIM-V medium and added to the target cells. The plates were incubated at 37° C. for 18 hours. The supernatants were harvested for γ-counting using harvester frames (Skatron, Inc. Sterling, Va., USA). The determinations were carried out in triplicate and the standard deviations were calculated. All of the experiments were repeated at least three times.

Specific Lysis was calculated as follows:

$$\% \text{ Specific Lysis} = \frac{\text{observed release (cpm)} - \text{spontaneous release (cpm)}}{\text{total release (cpm)} - \text{spontaneous release (cpm)}} \times 100$$

Spontaneous release was determined from wells to which 100 µl of complete medium had been added instead of effector cells; total releasable radioactivity was measured after treating the targets with 2.5% Triton X-100.

Blocking experiments: For HLA blocking experiments, UPC-10 control mAbs (Cappel/Organon Technique Corp., West Chester, Pa., USA) or anti-HLA-A2 mAbs (A2.69, #189HA-1; One Lambda, inc., Canoga Park, Calif., USA) at the dilution of 1:100 dilution were added to the labeled target cells (M-CaP and LNCaP cells) and incubated for 1 hour before the cytotoxic assay.

Flow Cytometry: Single color flow cytometric analysis: the procedure for single-color flow cytometric analysis has been previously described [Guadagni et al, 1990]. Briefly $1 \times 10^6$ cells were washed three times with cold $Ca^{2+}$ and $Mg^{2+}$-free Dulbecco's phosphate-buffered saline (DPBS) and then stained for 1 h with 1 µg of mAb against CD3, CD4, CD8, CD56, CD19, CD11c, CD1a, CD83, CD86, CD80, CD54, CD58 (all purchased from Becton Dickinson, San Jose, Calif.), HLA class I (W6/32) (Scra, Sussex, England), and MOPC-21 (Cappel/Organon Tecknica Corp. West Chester, Pa.) in a volume of 100 µl of PBS containing 1% bovine serum albumin. The cells were then washed three times with cold DPBS and incubated for an additional hour in the presence of 1:100 dilution (volume of 100 µl PBS containing 1% bovine serum albumin) of fluoresceine-conjugated goat anti-mouse immunoglobulin (Ig) (Kirkengard and Perry Labs, Gaithersburg, Md., USA). The cells were again washed three times with DPBS and resuspended in DPBS at the concentration of $1 \times 10^6$ cells/ml, and immediately analyzed using a Becton Dickinson FACScan equipped with a blue laser with an excitation of 15 nW at 488 nm. The data were gathered from 10,000 live cells and used to evaluate results.

Dual color flow cytometric analysis : this procedure closely resembled that used for the single-color flow cytometry with the following exceptions. The mAbs used were anti-CD3 and anti-CD4 fluoresceine conjugate and anti-CD56 and anti-CD8 phycoerythrin conjugate, anti IgG1 fluorescein conjugate and anti-IgG3 phycoerythrin (all purchased from Becton Dickinson, San Jose, Calif.). The cells were simultaneously stained for one hour and then washed three times, resuspended as above, and immediately analyzed using a Becton Dickinson FACScan equipped, with a blue laser with an excitation of 15 nW at 488 nm, and the Lysis II program.

HLA Typing: The HLA phenotyping of the donor PBMC was performed by the Blood Bank of the Azienda Ospedaliera Senese, Policlinico "Le Scotte", Siena, Italy using a standard antibody-dependent micro-cytotoxicity assay and a defined panel of anti-HLA antisera for HLA class I determinations.

Statistical Consideration: The differences between means were statistically analyzed using the two tailed Student's t-test for paired samples and Stat View statistical software (Abacus Concepts, Berkeley, Calif.) and the results were expressed as the mean of four determinations derived from three different experiments+/−standard deviation. A P value of <0.05 was considered statistically significant.

PTH-rP specific TILs: A PTR-4 peptide specific CTL line, designated TM-PTR-4, was generated by the in vitro stimulation of human TIL with PTR-4 peptide pulsed autologous DC and IL-2. TILs had been isolated from a metastatic sample taken by a bone biopsy, performed on a patient with advanced prostate carcinoma enrolled in a clinical trial of immunotherapy GM-CSF and IL-2 before he received any immunological treatment. DCs, by contrast, were isolated from the same patient after he had received at least a cycle of treatment with GM-CSF and IL-2. Immunofluorescence FACS analysis showed that this patient was HLA-A2.1$^+$, and that the administration of GM-CSF and IL-2 had indeed increased in his PBMC, the percentage of cells showing the immunophenotype and the function of activated bone marrow derived DC (data from a Clinical trial). In order to increase and purify the DC population to use as APC, patient PBMC, isolated after he had received the cytokine immunological treatment, were cultured in medium containing GM-CSF and IL-4 as described above, and finally used to stimulate the autologous TIL.

After 4 IVS (eight weeks) this TM-PTR-4 lymphocyte culture was investigated for immunophenotype expression and cytotoxic activity. Progenitor TIL (TM-TIL) were also cultured in presence of IL-2 and cyclically stimulated with the same irradiated autologous DC co-cultured in presence of autologous irradiated tumor cells. After eight weeks of culture, also these lymphocytes were investigated for immunophenotype expression and cytotoxic activity. The immunophenotype study revealed that TM-PTR-4 culture mainly, consisted of CD3$^+$, CD56$^-$, CD5$^+$ (22%), CD45RO$^+$ (45%) cells, which were prevalently CD4$^-$/CD8$^+$ (65.8%). The TM-TIL had a similar phenotype with a higher percentage of CD56$^+$ cells (20%), no CD5$^+$ (2.2%) expression and a much lower percentage of CD45$^{Ro+}$ (21%) memory T cells (Table 1). A similar phenotype was also found in the T cell line, generated by stimulating the same TIL with peptide pulsed DC derived from PBMC isolated before patient treatment with GM-CSF and IL-2 (data not shown).

TABLE 1

Flow cytometric analysis of surface markers on PTH-rP peptide specific CTL lines

| T cell line | CD3+ | CD4+/CD8− | CD4−/CD8+ | CD4+/CD8+ | CD56+ | CD5+ | CD45RO+ |
|---|---|---|---|---|---|---|---|
| TM-TIL | 87.2 | 25.3 | 69.3 | 4.5 | 36 | 2.2 | 21 |
| TM-PTR-4 | 96.46 | 28.57 | 65.81 | 2.41 | 3.29 | 22 | 45 |
| ND-PTR-4 | 98% | 41.2% | 37.3% | 15.2% | 25% | — | 40% |

In this patient no PTH-rP peptide specific T cell line could be generated by using PTR-4 pulsed DC to stimulate PBMC isolated prior cytokine therapy. (data not shown). As previously described, a CTL line specific for the PTH-rP peptide was instead generated from PBMC isolated from a HLA-A2.1+ healthy donor, by means of cyclic stimulation with low dose IL-2 and PTR-4 peptide-pulsed autologous DC. DC used as CTL antigen presenting cells were generated as described in method section. The CTL line generated in this way, was investigated for immunophenotype expression and cytolytic activity after 4 and 6 IVS (two and three months of culture). Direct double-stain flow cytometry immunofluorescence showed that the CTL lines expressed a CD3+ (98%) phenotype with different percentages of CD56+ (25%), CD4+/CD8− (41.2%), CD4+/CD8+ (15.2%) and CD4−/CD8+ (37.3%) cells (Table 1).

Figure 4:
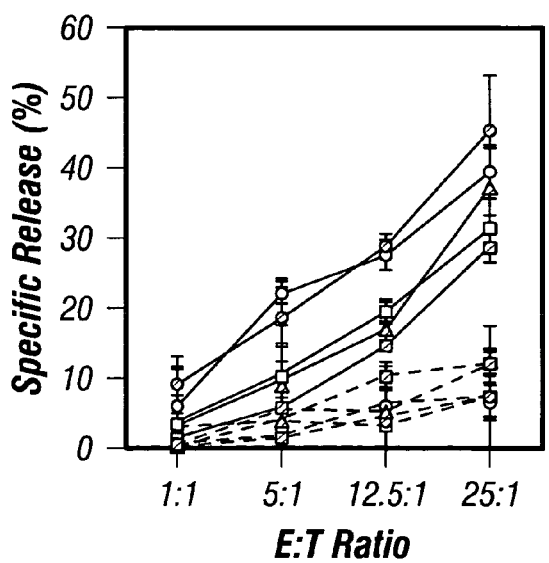
FIG. 4: this figure shows the cytotoxic activity of human tumor-infiltrating lymphocytes (TIL) stimulated in vitro with IL-2 and PTH-rP peptide pulsed autologous dendritic cells against CIR-A2 cells (-○-), CIR-A2 pulsed with 25 μg/ml of PTH-rP (PTR-4) peptide (—●—), CIR-A2 cells transfected with pc3-DNA (-●-), CIR-A2 cells transfected with PTH-rP plasmid (GC90) (—○—), HLA-A2.1+/PTH-rP− colon carcinoma SW1463 cells (-□-), HLA-A2.1+/PTH-rP+ prostate carcinoma LNCaP cells (—■—), LNCaP cells in presence of anti-HLA-A2.1 mAb (dilution 1:100) (-■-), LNCaP cells in presence of a control isotype mAb (UPC-10) (—□—), PTH-rP+ autologous metastatic prostate cancer M-CaP cells in presence of UPC-10 (—▲—), and M-CaP cells in presence of an anti-HLA-A2.1 (A2,69) mAb (-Δ-). Data shown in the figure are derived from three different experiments for each target cell line with similar results. In the cytotoxic tests the differences between the values from PTH-rP peptide pulsed- and PTH-rP transfected-CIR-A2 compared with values from unpulsed CIR-A2 and pcDNA3 trasfected CIR-A2 cells, respectively were found statistically significant (P<0.05); the values from LNCaP cells in presence of A2.69 and SW-1463 cells with the values from LNCaP cells in presence of UPC-10 and LNCaP cells, respectively were found statistically significant (P<0.05); the values from M-CaP cells in presence of UPC-10 and M-CaP cells in presence of A2.69 respectively, were found statistically significant (P<0.05).

CTL line cytotoxic activity: Six hour cytotoxic assays by means of $^{51}$Cr release technique revealed that TM-PTR-4 lymphocytes were able to kill CIR-A2 target cells pulsed with PTR-4 peptide or transfected with GC90, a plasmid engineered to express PTH-rP gene. They also killed the HLA-A2.1+/PTH-rP+ prostate carcinoma LNCaP cell line (Figure). No CTL mediated lysis was conversely observed against unpulsed CIR-A2 cells or the cells pulsed with HLA-A2.1 molecule binding peptides other than PTR-4, or CIR-A2 transfected with the plasmid vector (pcDNA3), or against colon cancer SW-1463 cells, which are HLA-A2.1+ and unable to produce PTH-rP (FIG. 4). Target cell production of PTH-rP and membrane expression of HLA-A2.1 molecules is shown in Table 2.

TABLE 2

HLA-A2.1 molecule expression and PTH-rP production in lymphocyte target cells

| Target Cells | HLA-A2.1 expression (%)* | PTH-rP production (pg ml$^{-1}$ × 10$^6$ cells)# |
|---|---|---|
| CIR-A2 | 98.5 (2.2) | Not detectable |
| CIR-A2 transfected with pcDNA3 | 97.2 (4.24) | Not detectable |
| CIR-A2 transfected with GC90 (PTH-rP gene plasmid) | 96.6 (3.23) | 13.56 (5.6) |
| LNCaP | 29.8 (3.7) | 15.2 (5.5) |
| M-CaP | 60.1 (2.2) | 25.1 (3.5) |
| SW1463 | 75 (3.2) | Not detectable |

*HLA-A2.1 expression was evaluated by indirect immunofluorescence using an anti-HLA-A2.1 mAb (A2.69) and a FICT conjugated goat-anti-mouse. Results are expressed as percentage of fluorescent cells. Marker expression was considered negative when lower than 4%. Results are expressed as percentage of each cell sample reactive with mAb. Routinely, 2-4% of cells are stained when treated either with or without priming mAb or an isotype related control mAb.
PTH-rP was evaluated by a sandwich immunoradiometric assay (IRMA); values lower than 1.5 pg were considered negative.
*#Numbers in parentheses represent standard deviations.

Six hour cytotoxic assays also revealed TM-PTR-4 T-lymphocyte ability to kill autologous (M-CaP) prostate cancer cells (FIG. 4). Autologous M-CaP prostate cancer cells derived from the same sample as that from which lymphocytes were isolated, were cultured in presence of androgens and insulin for six weeks before being used as targets in CTL assays. The cells used as CTL targets were fibroblast free and had an exponential growth rate (data not shown). M-CaP cells were considered prostate cancer cells after a morphological and immunohistochemical study had been performed by a pathologist. PSA expression in the epithelial aggregates was, in fact, demonstrated by immunohistochemistry as an intense red staining of the cytoplasm that masks nuclei and cell borders. The M-CaP target cells were also positive for the expression of HLA-A2.1 (60%), and PTH-rP (25 ng/ml×10$^6$ cells) (Table 2).

HLA-A2.1 restriction of prostate cancer CTL-mediated cytolysis: TM-PTR-4 mediated target cell cytolysis was restricted by HLA-A2.1 since tumor cell killing was abrogated by the anti-class I mAb (A2.69) (FIG. 4), however prostate cancer cell cytolysis by the TM-PTR-4 T cell line was not affected by the treatment with a A2.69 isotype control antibody not reacting with target cells (FIG. 4).

Figure 5:
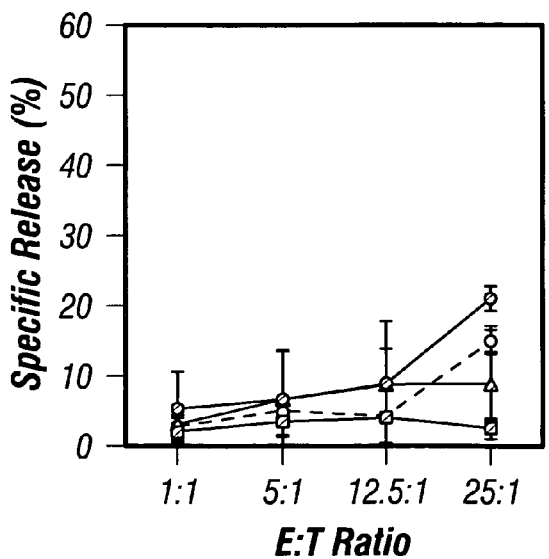
FIG. 5: this figure shows the cytotoxic activity of the human (TM-TIL), TIL line against CIR-A2 cells (-○-), CIR-A2 pulsed with 25 μg/ml of PTH-rP (PTR-4) peptide ((—●—), HLA-A2.1+/PTH-rP+ prostate carcinoma LNCaP cells (—■—), PTH-rP+ autologous metastatic prostate cancer M-CaP cells (—▲—). Data shown in the figure are derived from three different experiments for each target cell line with similar results. In the cytotoxic tests the differences between the values were never found statistically significant (P>0.05).

Bone metastases-derived TIL do not have any cytotoxic activity against target cells: Progenitor TIL not stimulated with PTH-rP epitope peptide, were also investigated for their anti-tumor activity in six and eighteen-hour cytotoxic assays. The TIL were maintained in culture for six and eight-weeks in presence of IL-2, and stimulated every 15 days with autologous irradiated prostate cancer cells and autologous DC. This T cell culture (TM-TIL), was not able to lyse LNCaP, SW-1463, unpulsed or PTR-4 peptide pulsed CIR-A2 targets, as well as autologous prostate cancer cells (FIG. 5).

Cytotoxic activity of patient TIL, in vitro stimulated with peptide pulsed DC derived from PBMC isolated prior patient cytokine therapy, was tested against the same target cells after four, six and eight in vitro stimulations. In none of these experiments a PTH-rP as well as a PTH-rP peptide specific cytotoxic activity could be demonstrated (data not shown). The same results were also obtained when peptide pulsed autologous (pre or post treatment) DC were used to stimulate in vitro patient PBMC instead of TIL (data not shown).

Figure 6:
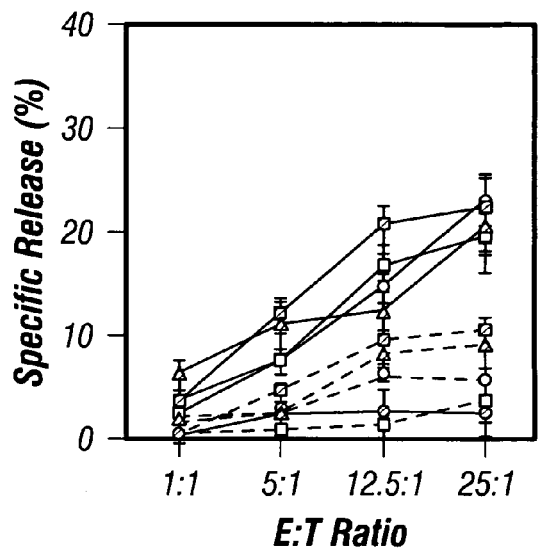
FIG. 6: this figure shows the cytotoxic activity of human PBMC stimulated in vitro with IL-2 and PTH-rP peptide pulsed autologous dendritic cells against CIR-A2 cells (-○-), CIR-A2 pulsed with 25 μg/ml of PTH-rP (PTR-4) peptide ((—●—), CIR-A2 cells transfected with pc3-DNA (-●-), CIR-A2 cells transfected with PTH-rP plasmid (GC90) (—○—)HLA-A2.1*/PTH-rP− colon carcinoma SW1463 cells (-□-), HLA-A2.1+/PTH-rP+ prostate carcinoma LNCaP cells (—■—), LNCaP cells in presence of anti-HLA-A2.1 mAb (dilution 1:100) (-■ -), LNCaP cells in presence of a control isotype mAb (UPC-10) (—□—), PTH-rP+ autologous metastatic prostate cancer M-CaP cells (—▲—). Data shown in the figure are derived from three different experiments for each target cell line with similar results. In the cytotoxic tests the differences between: the values from PTH-rP peptide pulsed- and PTH-rP transfected-CIR-A2 compared with values from unpulsed CIR-A2 and pcDNA3 transfected CIR-A2 cells, respectively were found statistically significant (P<0.05); the values from LNCaP cells in presence of A2.69 and SW-1463 cells with the values from LNCaP cells in presence of UPC-10 and LNCaP cells, respectively were found statistically significant (P<0.05); the values from M-CaP cells with the values from SW-1463 and CIR-A2 cells were found statistically not significant (P>0.05).

PTH-rP peptide specific cytotoxic activity of a CTL line generated from a normal donor: The PTH-rP and PTH-rP peptide specific cytotoxic activity of the CTL line derived from the normal donor was also investigated. In eighteen-hour cytotoxic assays it was observed that the latter CTL line, designated normal donor (ND)-PTR-4, was able to kill PTR-4 pulsed- or PTH-rP gene transfected-CIR-A2 target cells and exerted a minimal HLA-A2.1 restricted cytotoxic activity against LNCaP cells (FIG. 6). These T lymphocytes were conversely unable to kill: the peptide unpulsed CIR-A2 cells; the same target cells transfected with the plasmid vector (pcDNA3), or pulsed with the negative control peptide (CEA-derived) with HLA-A2.1 binding motifs; and the colon carcinoma, SW-1463 cells (FIG. 6). In contrast with TM-PTR-4, the PTR-4 specific CTL line (ND-PTR-4) derived from the normal donor was unable to kill the M-CAP cells, did not exert any cytotoxic activity in six hour $^{51}$Cr release assays (Data not shown in figure) and exerted a lower level of cytotoxic activity against PTR-4 pulsed and GC90 transfected CIR-A2 and LNCaP target cells (FIGS. 4 and 6).

These results show that T cells generated from prostate cancer patients' tumor infiltrating lymphocytes by stimulation with PTH-rP peptide pulsed dendritic cells can be reactivated from their anergic state and become cytotoxic against the PTH-rP expressing tumor, resulting in the rescue of PTH-rP specific anti-tumor activity. This demonstrates that the anti-tumor activity of T cells in patients with advanced and metastatic cancer is not irreversibly lost, but instead can be reactivated, leading to a tumor-specific immune response. The cytokine treatment with IL-2 and GM-CSF is believed to further increase immunocompetence in the cancer patients by increasing the percentage of dendritic cells in PBMCs and by promoting their maturation and functional activation, such as their antigen-presenting ability. Thus, this example shows that PTH-rP peptide based vaccine therapy and PTH-rP peptide specific T cell adoptive reinfusions, including tumor infiltrating lymphocytes, are promising modalities in the treatment of PTH-rP expressing malignancies and their bone metastases.

Example 3

This example shows the encapsulation of PTH-rP peptides into IRIVs, as well as the rosslinking of peptides to IRIVs.

For peptide encapsulation 32 mg egg phosphatidylcholine (PC), (Lipoid GmbH, Ludwigshafen, Germany) and 6 mg phosphatidylethanolamine (PE), (R. Berchtold, Biochemisches Labor, Bern, Switzerland) are dissolved in 2.66 ml of PBS containing 100 mM octaethyleneglycol (OEG) (Fluka Chemicals, Switzerland), (PBS-OEG). The influenza A/Singapore hemagglutinin is purified as described previously (J. J. Skehel, G. C. Schild, *The polypeptide composition of influenza A viruses.* Virology 44 (1971) 396-408). A solution containing 4 mg hemagglutinin is centrifuged for 30 min at 100,000 g and the pellet is dissolved in 1.33 ml of PBS-OEG. The lipophilic peptides and phospholipids are added to the hemagglutinin-solution, well mixed and sonicated for 1 min. This mixture is then centrifuged for 1 h at 100,000 g and the supernatant sterile filtered (0.22 mm). Virosomes are then formed by detergent removal using BioRad SM Bio-Beads.

For crosslinking of the PTH-rP peptides to the virosome surface, phosphatidylethanolamine PE is dissolved in methanol and 0.1% (v/v) triethylamine is added. The solution is then mixed with the heterobifunctional crosslinker N-γ-maleimidobutyryloxy-succimide-ester (GMBS), (Pierce Chemical Company, Rockford, Ill.) (ratio PE: GMBS=5:1), which was previously dissolved in dimethylsulfoxide (DMSO) (20° 1). After incubation during 30 minutes at room temperature, the solvents are evaporated for 1 h under vacuum in a speedvac centrifuge. The GMBS-PE is then dissolved in 1 ml of PBS containing 100 mM octaethyleneglycol (OEG) (Fluka Chemicals, Switzerland), (PBS-OEG) and the PTH-rP peptides are added (ratio of PE-GMBS to peptide=5:1). In this step, the phosphatidylethanolamine-GMBS reacts with a free cysteine of the PTH-rP peptides. After an incubation time of 30 minutes, free cysteine is added in order to inactivate free GMBS (ratio Cysteine:GMBS=10:1). 32 mg egg phosphatidylcholine (PC), (Lipoid GmbH, Ludwigshafen, Germany) and 6 mg phosphatidylethanolamine (PE), (R. Berchtold, Biochemisches Labor, Bern, Switzerland) were dissolved in 2.66 ml of PBS containing 100 mM octaethyleneglycol (OEG) (Fluka Chemicals, Switzerland), (PBS-OEG). The influenza A/Singapore hemagglutinin is purified as described above. A solution containing 4 mg hemagglutinin is centrifuged for 30 min at 100,000 g and the pellet dissolved in 1.33 ml of PBS-OEG. The PTH-rP peptide-GMBS-PE construct and phospholipids are added to the hemagglutinin-solution, well mixed and sonicated for 1 min. This mixture is then centrifuged for 1 h at 100,000 g and the supernatant sterile filtered (0.22 mm). Virosomes are then formed by detergent removal using BioRad SM Bio-Beads.

Example 4

This example show that PTH-rP peptides, when injected, can stimulate T cells to recognize and lyse tumor cells expressing PTH-rP. The PTR-4 peptide (SEQ ID NO:5) shows an atypical MHC I binding motif, lacking canonic anchor amino acids in positions 2 and 9, presumably generating an unstable MHC-peptide complex which may form the basis for the lack of tolerance to this PTH-rP peptide. To investigate this point and for comparison purposes, another PTH-rP peptide was selected with higher MHC theoretical binding motifs after screening the PTH-rP amino acid sequence (SEQ ID NO:1) with the HLA Peptide Binding Prediction analysis described by Parker. The effective binding MHC I molecules, measured by means of the T2 class-1 HLA upregulation test, and the high degree of divergence from the analogous peptide sequences belonging to human PTH were further reasons for choosing the PTR-2 (SEQ ID NO:3) peptide for comparative study with PTR-4 (SEQ ID NO:5). The data obtained suggest that the T cells specific for PTR-4 have greater functional avidity than PTR-2 specific T cells, even though PTR-2 forms a more stable complex with MHC. The results show that that injection of PTH-rP peptides can raise T cell responses against PTH-rP that are cytotoxic to tumor cells. Thus, PTH-rP peptides can be used in the preparation of peptide based vaccines, including mixtures of PTH-rP peptides, such as polyvalent vaccines, and may be used for preventive purposes after primary debulking of cancer patients by means of surgery, radio- or chemotherapy. Tumor cells expressing PTH-rP have greater metastatic potential and could be targeted before their implantation in bone tissue, thereby reducing the risk of metastatic spreading.

Peptide Synthesis: The peptides (PTR-2 and PTR-4) were synthesized using a solid phase automatic peptide synthesizer (model syto, MultiSyntech, Witten, D) and the fluorenylmethoxycarbonyl (Fmoc)/diisopropylcarbodiimide (DIC)/1-hydroxybenzotriazole (HOBT) strategy. They were cleaved from the resins and defracted by treatment with trifluoroacetic acid containing ethandiethiol, water trisbuthyl silone and anisole (93/2.5/2/1.5/1). The crude peptides were purified by HPLC using a Vydac C18 column (25 cm×1 cm, 10 μm). The products were dissolved in bidistilled water, sterile filtered and frozen at −70° C. at a concentration of 2 mg/ml. Peptide purity was more than 90% as analyzed by high-performance liquid chromatography (HPLC). The CAP-1 peptide was kindly donated by Dr. J. Schlom (EOS, NCI, Bethesda, Md., USA).

Cell cultures:The LNCaP (HLA-A(*)02.01$^+$ and PTH-rP$^+$) prostate carcinoma cell line, the MDA-MB 231 (HLA-A(*)02.01$^+$ and PTH-rP$^+$) breast carcinoma cell line, and the SW1463 (HLA-A(*)02.01$^+$ and PTH-rP$^-$) colon carcinoma cell line were purchased from the American Type Culture Collection (Rockville, Md.). The murine lymphoma cell line EL-4-HHD (HLA-A(*)02.01$^+$) has been previously described (Pascolo et al., J. Exp. Med. 185(12): 2043-2051, 1997). The mycoplasma-free cultures were maintained in complete medium (RPMI-1640 for LNCaP and EL-4-HHD, and Dulbecco's modified Eagle medium for SW1463 and MDA-MB 231) [Life Technologies Inc. (Gibco BRL) Grand Island, N.Y.] supplemented with 10% fetal bovine serum (FBS), 2 mM glutamine, 100 U/ml penicillin, and 100 µg/ml streptomycin (Life Technologies, Inc.). The 174CEM-T2 (T2; transport deletion mutant, Nijman et al., Eur. J. Immunol. 23: 1215-1219, 1993) and CIR-A2 (Storkus et al, J. Immunol. 138:1657-1659, 1987) cell lines were provided by Dr. Jeffrey Schlom (Experimental Oncology Section of the National Institute of Cancer, National Cancer Institute, Bethesda, Md., USA). The T2 and CIR-A2 cells were respectively maintained in Iscove's modified Dulbecco's complete medium (IMDM) and RPMI-1640 complete medium.

T2-A2, HLA up-regulation test: binding of the PTR-2 and PTR-4 peptides to HLA-A(*)02.01 molecules was evaluated by means of flow cytometry using T2 cells and the method described by Nijman et al. In this assay, increased stability (the accumulation of HLA-A(*)02.01 molecules on the surface of T2 cells as a consequence of peptide binding) is measured in terms of the increased binding of the antibody directed against HLA-A(*)02.01. Briefly, $10^6$ T2 cells in serum-free IMDM were incubated overnight with escalating concentrations (0, 5, 25 and 50 µg/ml) of the PTR peptides in 24-well culture plates at 37° C. in an atmosphere containing 5% $CO_2$. The cells were then washed two times with DPBS, and subsequently incubated for one hour with an anti-HLA-A(*)02.01 (A2.69) specific monoclonal antibody (A2.69, #189HA-1; One Lambda, Inc., Canoga Park, Calif.), using 10 µl of the recommended dilution per $10^6$ cells. UPC-10 (Cappel/Organon Teknika Corp) was used as an isotype control. The cells were again washed two times with DPBS, incubated with 100 µl of a 1:100 dilution of fluorescein isothiocyanate (FITC)-labeled anti-mouse IgG (Becton Dickinson Corp.), and analyzed by means of FACScan and single-color analysis. The cells were kept at 4° C. during all of the manipulations unless otherwise stated.

Generation of dendritic cells (DC) and T cell lines: PBMC were isolated from heparinized blood taken from two normal HLA-A(*)02.01 volunteers (one male and one female) using a lymphocyte separation medium gradient (Organon Tecknika, N.C.) as previously described (Boyum, Scand. J. Clin. Lab. Invest. 97 (suppl): 51-76, 1968).

The PBMC ($10^7$ cells/ml) for DC enrichment were seeded in T75 flasks in a 10 ml volume of complete medium (RPMI-1640) with 10% FBS for four hours at 37° C. in 5% $CO_2$, after which the non-adherent cells were removed. The adherent cells were then maintained for seven days in complete medium (RPMI-1640 with 10% FBS, 2 mM glutamine, 100 U/ml penicillin, and 100 µg/ml streptomycin) containing 50 ng/ml of granulocyte-macrophage colony stimulating factor (GM-CSF) and 0.5 ng/ml of interleukin-4 (IL-4) (both purchased from R and D Systems, Minneapolis, Minn.). The medium containing GM-CSF and IL-4 was replaced every 48 hours. After seven days of culture, the DC phenotype of the cells was investigated by means of flow cytometry direct immunofluorescence. To estimate DC enrichment before CTL stimulation, the cultures were examined for the expression of CD1a, HLA-I, HLA-DR, CD11c, CD80 and CD86, and CD83 markers [38-40].

CTL cultures:The PBMC for CTL primary cultures were washed two times in DPBS and then resuspended in AIM-V medium (Life Technologies, Inc.) supplemented with 5% pooled human AB serum (Valley Biomedical, Winchester, Va.), 2 mM glutamine, 100 U/ml penicillin, and 100 µg/ml of streptomycin (Gibco BRL). Cells ($2\times10^5$) in a 100 µl volume of complete medium were added to each well of a 96-well flat-bottomed assay plate (Coming, Costar Corp. Cambridge, Mass.). The irradiated autologous DC were pulsed with each one of the specific PTH-rP peptides (25 µg/ml) and added to the lymphocyte cultures at a final DC/PBMC ratio of 1:5. The co-cultures were then incubated for five days at 37° C. in a humidified atmosphere containing 5% $CO_2$. The cultures were then fed with human recombinant interleukin-2 (rIL-2) (Cetus Corp. Emmerville, UK) (20 U/ml) for ten days, with the IL-2-containing medium being replenished every three days. Incubation for five days with peptide-pulsed DC plus ten days with IL-2 constitutes one in vitro stimulation cycle (IVS). The T cell cultures were re-stimulated with PTH-rP peptide (the same as that used for the first stimulation)-pulsed autologous DC. The irradiated (5,000 rads) autologous DC were added in a 100 µl volume of complete medium (AIM-V) and used as antigen-presenting cells. After the second IVS the cells were pooled and then seeded in 24-multiwell plates at a final concentration of $10^5$ cells/ml in a volume of 2 ml/well. T cells were subsequently restimulated as described above using the same DC:T cell ratio.

Cytotoxic assays: Cytotoxic activity of CTL derived from HHD mice against mouse target cells was tested in 6 hour $^{51}$Cr release assays. Human CTL activity against human target cells could not be revealed in 6-8 hours and therefore, 18 hour $^{111}$In release assays were performed. At the present no explanation does exist for this observation. It could be due to partial human tumor cell ability to escape the cytolytic effectors or to the intrinsic resistance to the cytolytic mediator released by human CTLs or eventually to different mechanism of killing used by human and mouse CTLs.

Human target cells were labeled with 50 µCi of $^{111}$In-oxyquinoline (Medi Physics Inc., Arlington, Ill.) for 15 minutes at room temperature. Mouse EL-4-HHD target cells were instead labeled with 50 µCi of $Na_2^{51}CrO_4$ (Amersham, UK) for 60 minutes at room temperature. Target cells ($0.5\times10^4$) in 100 µl of complete medium (see below) were added to each of the wells in 96-well flat-bottomed assay plates (Corning Costar Corp.). The labeled targets were incubated at 37° C. in 5% $CO_2$ before the addition of effector cells. The T cells were then suspended in 100 µl of AIM-V medium and added to the target cells. The plates were incubated at 37° C. for 6 or 18 hours, and the supernatants harvested for y-counting with harvester frames (Skatron, Inc., Sterling, Va.). The determinations were made in triplicate and standard deviations were calculated. All of the experiments were repeated at least three times. Specific lysis was calculated as previously described. Spontaneous release was determined from the wells to which 100 µl of complete medium were added instead of effector cells. Total releasable radioactivity was obtained after treating the target with 2.5% Triton X-100.

Blocking experiments: For the HLA blocking experiments, UPC-10 (Cappel/Organon Technique Corp., West Chester, Pa.) control mAb or anti-HLA-A(*)02.01 (A2.69, #189HA-1; One Lambda, Inc., Canoga Park, Calif.) or HLA class I A, B, C (W6/32) (Scra, Sussex, England), were incubated for one hour before the cytotoxic assay.

Flow cytometry: the procedure for the flow cytometric analysis has been previously described (Guadagni, Cancer Res. 50: 6245-6255, 1990). The cells were first incubated with primary mouse anti-human mAbs against CD3, CD4, CD8, CD56, CD19, CD1a, HLA-I, HLA-DR, CD11c, CD80 and CD86, CD83 (all purchased from Becton Dickinson, San Jose, Calif.), HLA class I (W6/32) (Scra, Sussex, England), and MOPC-21 (Cappel/Organon Tecknica Corp. West Chester, Pa.). Subsequently, they were stained with a fluoresceine-conjugated goat anti-mouse immunoglobulin (Ig) (Kirkengard and Perry Labs, Gaithersburg, Md.) (1:100 dilution) and, finally, the samples containing 1×10⁶ cells in 1 ml of Ca⁺⁺/Mg⁺⁺ free DPBS were analyzed using a Becton Dickinson FACScan equipped with a blue laser with an excitation level of 15 nW at 488 nm. The data gathered from 10,000 live cells were used to evaluate the results. The procedure for dual-color flow cytometry analysis closely resembles the single-color procedure with the following exceptions. The monoclonal antibodies were anti-CD3 and anti-CD4 fluorescein conjugate, anti-CD56 and anti-CD8 phycoerythrin conjugate, anti IgG1 fluorescein conjugate and anti-IgG3 phycoerythrin conjugate (Becton Dickinson). The cells were simultaneously stained for one hour, after which they were washed three times; resuspended as above, and immediately analyzed using a Becton Dickinson FACScan equipped with a blue laser with an excitation of level of 15 nW at 488 nm and the Lysis II program.

HLA typing: The PBMC HLA of the two donors (98/003263 and 98/0003668) was phenotyped by the Blood Bank of the Azienda Ospedaliera Senese, Policlinico "Le Scotte", Siena, Italy, using a standard antibody-dependent micro-cytotoxicity assay and a defined panel of anti-HLA antisera for HLA class I determinations. The polymerase chain reaction was used to type HLA-class II.

Animals: The HHD mice have been previously described (Firat et al., Eur. J. Immunol. 29(10): 3112-2121, 1999). They are α2m -/-, Db-/- and express a HLA-A(*)02.01 monochain consisting of the α 1 and α 2 domains of HLA-A(*)02.01, and the α 3 domain of Db linked by its N-terminus to the C-terminus of human α 2-m by a 15-amino acid long peptide. Mice were housed in a temperature-controlled, light cycled room. All in vivo experiments were performed in accordance with local ethical guidelines.

Vaccination of HHD mice: The HHD mice were injected at the base of the tail with 100 µg of the epitope of interest emulsified in IFA in the presence of 140 µg of the IAb restricted HBV core antigen derived T helper epitope (SEQ ID NO: 6, aa 128-140; sequence TPPAYRPPNAPIL). The injection was repeated for an immunological boost after 11 days. Two weeks after peptide reboosting (25 days since the first injection), the HHD animals were sacrificed for histology study and in vitro spleen cell restimulation.

In vivo study of HHD mice injected with PTH-rP peptides: Two series of three mice were immunized with each one of the two PTH-rP peptides or a control peptide (hTRT). Two series of three animals for each peptide were used at different times. After 11 days, the mice were reinjected with cognate peptide for reboost. On days 11 and 25, the sera of the immunized HHD mice were collected from the retro-orbital sinus for serum Ca ion level evaluation.

Human synthetic thyreocalcitonin (Sigma-Aldrich Corp # T3535). (0.1 mg in 1 ml of 0.9% saline solution) injected sc. in the dorsal neck was used as a positive control, which is capable to induce hypocalcemia (0.64+/−0.645 mmol/L) after 6 hours, in a group of three mice. Normal value were found in a range of 1.29+/−25 mmol/L.

Two weeks after the boost, the mice were sacrificed and 4 µM-thick paraffin sections were made from sampled tissues and stained with hematoxylin-eosin-safranin (Merck, Germany). Spleen cells were collected and re stimulated in vitro with 10 µM of cognate peptide.

Generation of PTH-rP plasmid/influenza virosomes: The PTH-rP gene was amplified from the prostate carcinoma DU-145 cell line by RT-PCR and cloned in the BamHI-EcoRI sites of the pcDNA3 expression vector (InVitrogen) in order to obtain the recombinant plasmid GC90. The construct was grown in DH5 cells. Plasmid DNA was purified using the Qiagen Endo Free plasmid kit (QIAGEN) as described by the manufacturer. Influenza virosomes were prepared as described elsewhere. Non-encapsulated plasmids were separated by 0.1 gel filtration on a High Load Superdex 200 column (Pharmacia). The column was equilibrated with sterile PBS. The void volume fractions containing the virosomes with encapsulated plasmids were eluted with PBS and collected. For cell transfection, about 10⁵ target EL-4-HHD cells were grown in 6-well microplates at 37° C. and infected with 0.3 µg of DNA-virosomes or transfected with 1 µg of plasmid DNA using the Effectene Transfection reagent (QIAGEN) as described by the manufacturer. After two days, PTH-rP antigen expression was analysed by evaluating the presence of the specific mRNA by RT-PCR and immunofluorescence. Briefly, the cells were washed twice with PBS, fixed with cold methanol/acetone and treated with a rabbit anti-PTH-rP serum (Calbiochem) followed by FICT-conjugated goat anti-rabbit IgG (1/100) (DBA). The coverslips were mounted on slides and examined using a Diaplan microscope (Leitz).

Statistical considerations: The between-mean differences were statistically analysed using Stat View statistical software (Abacus Concepts, Berkeley, Calif.). The results were expressed as the mean value+/−SD of four determinations made in three different experiments, and the differences determined using the two-tailed Student t test for paired samples. A P value of <0.05 was considered statistically significant.

Peptide selection and HLA-A(*)02.01 binding: In order to test the immunogenicity of PTH-rP protein and test possible tolerance of human T cell repertoire specific for it, the PTH-rP molecules were screened with the "Parker" algorithm (BIMAS) in order to predict peptides having high theoretical HLA-A(*)02.01 binding motifs. The functional binding of the two peptides to HLA-A(*)02.01 molecules was tested in vitro by means of the T2 test. PTH-rP peptides with similar or overlapping amino acid homology to the analogue sequences of parathyroid hormone (PTH) were cut out of the screening. The peptide sequences included in the first 36 amino acids (pro-peptide) were ignored although theoretically predicted with higher affinity for the HLA-A (*)02.01 molecule. The peptide sequences included in the mature PTH-rP molecules and responsible for its biological activity (amino acid 37-177, Suva et al., Science 237: 893-896, 1987) were examined. Two representative peptides were selected for this study, PTR-2 (SEQ ID NO: 3; p59-68, FLHHLIAEIH) and PTR-4 (SEQ ID NO: 5; p165-173, TSTTSLELD). PTR-2 was found to have the the highest HLA-A(*)02.01 binding affinity, whereas PTR-4 is surprisingly immunogenic despite its non-canonic anchor motifs and intermediate-low binding affinity. Both PTR-2 and PTR-4 showed 100% amino acid divergence from the homologue sequence in the PTH (Table 3). The results showed PTR-2 and PTR-4 capable of HLA-A(*)02.01 binding in comparison with the CEA peptide (CAP-1) used as a positive control (Table 3).

TABLE 3

HLA-A2.1 binding of human parathyroid hormone-related protein (PTH-rP) derived peptides[a] (HLA-A2.1 Class I up-regulation test)

| Peptide | Position in PTH- | Amino acid Sequence | T2 binding[b] | | |
|---|---|---|---|---|---|
| No peptide | NA | NA | 244.7 +/− 42.43 | | |
| PTR-2 | 59-68 | FLHHLIAEIH | 279[d] | 532[e] | 719.2[f] |
| Parathyroid | 23-31 | WLRKKLQD | ND | ND | ND |
| PTR-4 | 165-173 | TSTTSLELD | 291[d] | 362.4[e] | 399.4[f] |

TABLE 3-continued

HLA-A2.1 binding of human parathyroid hormone-related protein (PTH-rP) derived peptides[a] (HLA-A2.1 Class I up-regulation test)

| Peptide | Position in PTH- | Amino acid Sequence | | T2 binding[b] | |
|---|---|---|---|---|---|
| Parathyroid | NA | NA | NA | NA | NA |
| CAP-1[c] | NA | YLSGANLNL | 240[d] | 352[e] | 502.9[f] |

[a]Peptide binding was evaluated by means of an indirect immunofluorescence FACScan of 174 CEM-T2 cells reacting with an anti-HLA-A(*) 02.01 monoclonal antibody (A2, 69 dilution 1:100) and a secondary fluorescein isothiocyanate (FITC)-labeled anti-mouse IgG (26).
[b]Results expressed in relative fluorescence values (the control value of 287.116 derived from the average mean intensity of 244.7 + the standard deviation of 42.43 was chosen as the positive cut-off value).
[c]CAP-1, an HLA-A2.1 binding carcinoembryonic antigen derived peptide, was used as a positive controls. Dose-response at peptide concentrations of
[d]5 μg/ml;
[e]25 μg/ml;
[f]50 μg/ml.

Figure 7A:
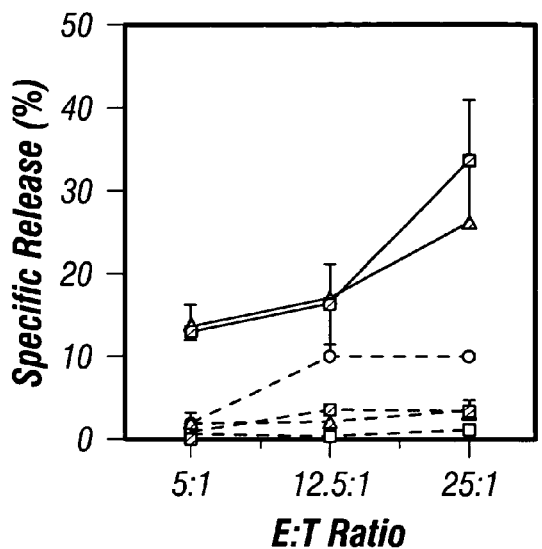
FIG. 7: this figure shows the ability of human PTH-rP peptide specific CTL lines generated from donor 1 (circles) and donor 2 (squares) to lyse CIR-A2 target cells previously pulsed with the cognate peptide. T-cell lines generated using PTR-2 (A) or PTR-4 peptides (B) were tested for their ability to lyse $^{111}$In-labeled CIR-A2 pulsed with PTR-2 or PTR-4 peptides (filled circles and squares with bold continuous lines, respectively), the control CEA peptide (CAP-1) (filled circles and squares with dashed lines, respectively), or no peptide (empty circles and squares with dashed lines, respectively). An 18-hour assay was performed with the peptides being used at a concentration of 25 μg/ml. The results are expressed as the percentage of specific lysis at different effector:target ratios. $^{111}$In release in the presence of culture medium without effectors was less than 15%. Mean values from triplicate determinations in individual experiments (performed at the 6$^{th}$, 8$^{th}$, 10$^{th}$, and 12$^{th}$ CTL line in vitro stimulation), with standard deviations. There was a significant difference (P<0.05: two-tailed t test) of values when results from cognate peptide pulsed CIR-A2 target cells and controls were compared (CIR-A2 unpulsed or pulsed with the control peptide).
Figure 7B:
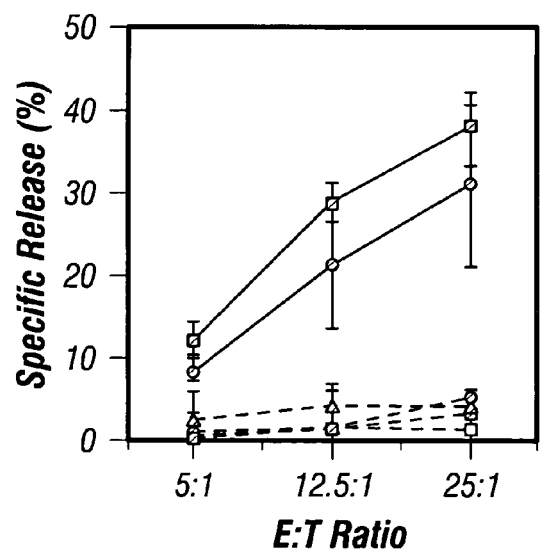

Generation of PTH-rP peptide-specific CTL lines: In order to evaluate the PTH-rP specific T cell repertoire availability in humans, CTL lines specific for each PTH-rP peptide were generated from PBMC of two different HLA-A(*)02.01[+] healthy donors by means of cyclic in vitro stimulations with peptide-pulsed autologous DC and IL-2. Two different CTL lines were generated from each donor and designated as T-Donor-1 or T-Donor-2 followed by the specific peptide used for CTL stimulation (T-Donor-1-PTR-2, T-Donor-2-PTR-2, etc.). All of the lymphocyte cultures were investigated for immunophenotype expression and cytolytic activity after at least six stimulation cycles. Direct double-stain flow cytometry immunofluorescence showed that the CTL lines expressed a CD3-positive phenotype (>90%) with different percentages of CD4[+]/CD8[−] (range 22-40%) and CD4[−]/CD8[+] (range 60-90%). The specificity of CTL lines was evaluated against PTH-rP peptide-pulsed CIR-A2 (HLA-A(*)02.01[+]) target cells. Cytotoxic assays demonstrated the peptide specificity of the CTL lines, which were able to kill target cells only when pulsed with the cognate peptide. The CTL lines were unable to kill the upulsed target cells or pulsed with the control CAP-1 peptide (FIG. 7). These results demonstrate that a PTH-rP peptide specific human CTL repertoire is available and mobilizable.

Figure 8A:
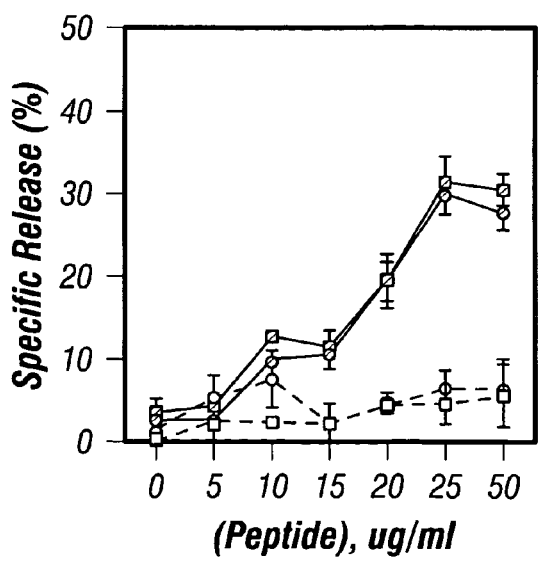
FIG. 8: this figure shows the ability of human PTH-rP peptide specific CTL lines generated from donor 1 (circles) and donor 2 (squares) to lyse CIR-A2 target cells previously pulsed with different concentrations of the cognate peptide. T-cell lines generated using PTR-2 (A) or PTR-4 peptides (B) were tested for their ability to lyse $^{111}$In-labeled CIR-A2 pulsed with PTR-2 or PTR-4 peptides (filled circles and squares with bold continuous lines, respectively), or the control CEA peptide (CAP-1) (empty circles and squares with dashed lines, respectively). An 18-hour assay was performed with the peptides being used at the concentration of 0, 5, 10, 20, 25, and 50 μg/ml, at the Effector/Target ratio of 25:1. $^{111}$In release in the presence of culture medium without effectors was less than 15%. Mean values from triplicate determinations in individual experiments (performed at the 8$^{th}$, 10$^{th}$ and 15$^{th}$) CTL line in vitro stimulation), with standard deviations. There was a significant difference (P<0.05: two-tailed t test) of values when results from cognate peptide pulsed CIR-A2 target cells and CIR-A2 pulsed with the control CAP-1 peptide were compared.
Figure 8B:
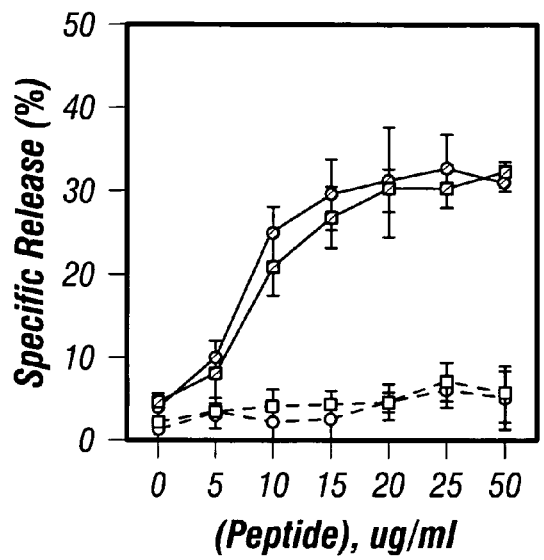
Figure 9A:
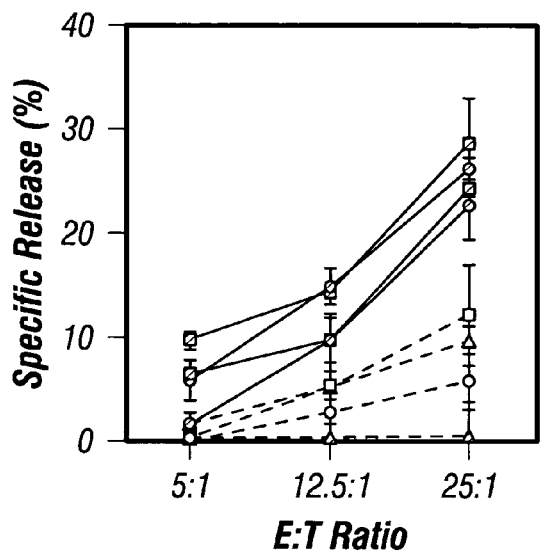
FIG. 9: this figure shows the ability of human PTH-rP specific CTL lines to lyse in vitro HLA-A(*)02.01+ tumor cells producing PTH-rP. T-cell lines generated using PTR-2 (A, C) or PTR-4 peptides (B, D) were tested for their ability to lyse $^{111}$In-labeled prostate (LNCaP) (A, B) and breast carcinoma (MDA-MB-231) (C, D) target cells. HLA-A(*) 02.01+ colon carcinoma SW-1463 (A, B, C, D) cells incapable of producing PTH-rP were used as a negative control target. The cytotoxic activity of the T cell lines against LNCaP and MDA-MB-231 cells in fresh medium is represented by filled circles and a bold line, respectively, for the donor 1; and by filled squares and a bold line for the donor 2. The cytotoxic activity of the T cell lines against LNCaP and MDA-MB-231 cells in the presence of the UPC-10 mAb is represented by filled circles and a continuous line, respectively, for the donor 1; and by filled squares and a continuous for the donor 2. The cytotoxic activity of the T cell lines against LNCaP and MDA-MB-231 cells in the presence of mouse anti-human HLA-A(*)02.01 mAb is represented by empty circles and a dashed line, respectively, for the donor 1; and by empty squares and a dashed line for the donor 2. The cytotoxic activity of the T cell lines against SW-1463 target cells is represented by filled squares and a bolded dashed line for the donor 1 and empty squares and a bolded dashed line for the donor 2. The target cells ($1\times10^6$) were labeled with $^{111}$In, incubated for one hour in the presence of medium containing no antibody, negative control antibody UPC-10 (10 μg/ml) or anti-HLA-A2,69 (1:100 dilution), and then used as targets in 18-hour cytotoxic assays. The results are from single experiments with triplicate determinations, expressed as the percentage of specific release at different effector:target ratios. This experiment was performed three times with similar results (performed at the, $8^{th}$, $10^{th}$ and $12^{th}$ CTL line in vitro stimulation). There were significant differences ($P<0.05$: two-tailed t test) between the values obtained from the same T cell line against: LNCaP+UPC-10 vs LNCaP+A2.69; MDA-MB-231+UPC-10 vs MDA-MB-231+A2.69; LNCaP+UPC-10 vs SW1463; MDA-MB-231+ UPC-10 vs SW1463. No significant differences were found when the same T cell line was tested against LNCaP in fresh medium vs LNCaP+UPC-10 or MDA-MB-231 in fresh medium vs MDA-MB-231+UPC-10. The spontaneous release in these assays in the presence or absence of mAbs without effectors was always less than 15%.
Figure 9B:
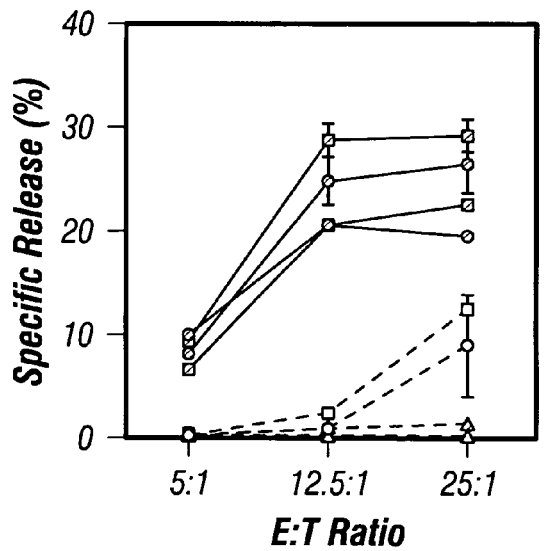
Figure 9C:
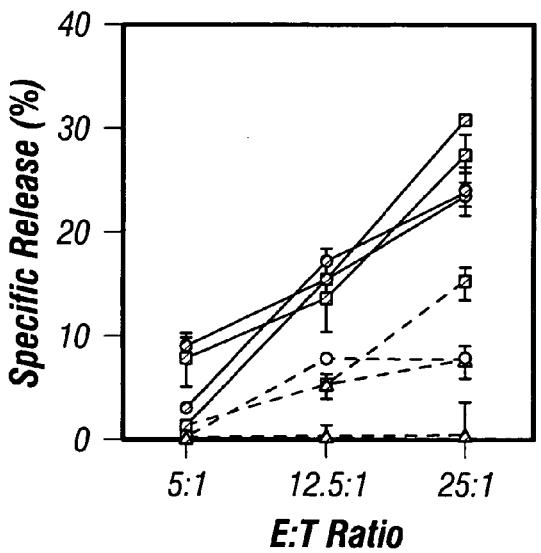
Figure 9D:
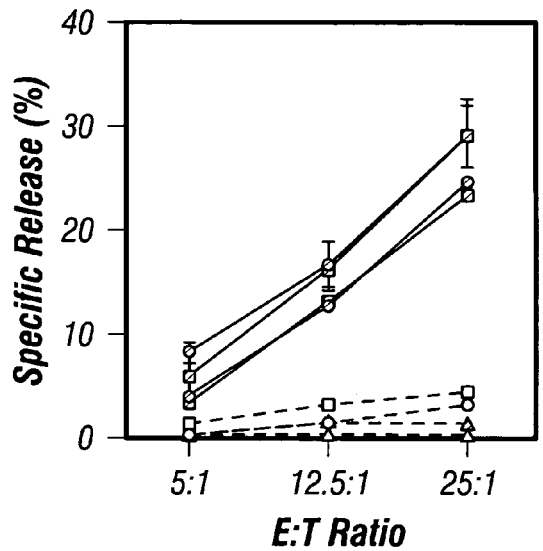
Figure 10A:
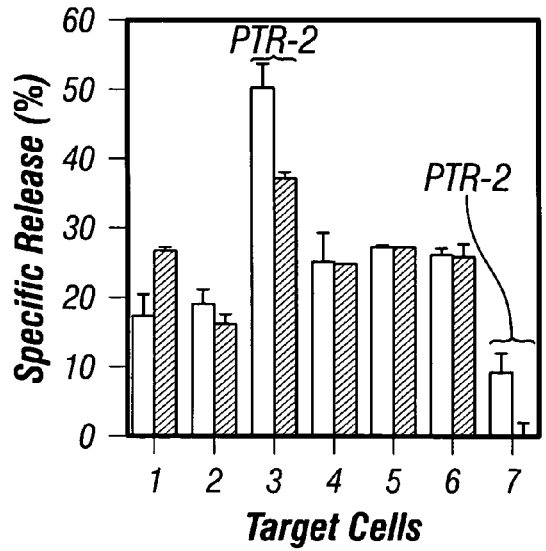
FIG. 10: this figure shows that cognate peptide pulsed T2 target cells used as cold competitors abrogate the CTL mediated lysis of prostate and breast carcinoma cells. The figure shows the results of a competition assay using an 18 $^{111}$In release assay expressed as the percentage of specific lysis at an effector:target ratio of 25:1. CTL lines form donor 1 (empty bar) and donor 2 (filled bar) were tested against labeled LNCaP (A, B) or MDA-MB-231 (C, D) in presence of unlabeled T2 used at a ratio of 1:10. The T2 cells were incubated with or without the cognate PTH-rP peptide (25 μg/ml) in serum-free medium for 24 hours at 37° C. before being added to the assay. There was a significant difference ($P<0.05$: two-tailed t test) between the value from LNCaP+ cold T2 pulsed with the specific peptide and the data derived from labeled LNCaP+unlabeled T2 not pulsed with peptide or pulsed with the CEA (CAP-1) control peptide. There was a significant difference ($P<0.05$: two-tailed t test) between the value for MDA-MB-231+cold T2 pulsed with the specific peptide and the data derived from labeled MDA-MB-231+unlabeled T2 not pulsed with peptide or pulsed with the CEA (CAP-1) control peptide. Each experiment was repeated three times with similar results (performed at the $8^{th}$, $12^{th}$, and $15^{th}$ CTL line in vitro stimulation). Numbers at the bottom of the graphs represent: (1) $^{111}$In-labeled T2-A2 cells with no cold competitors; (2), $^{111}$In-labeled T2-A2 cells pulsed with CAP-1 targets with no cold competitors; (3), $^{111}$In-labeled T2-A2 targets pulsed cognate-PTH-rP peptide with no cold competitors; (4), $^{111}$In-labeled LNCaP (FIGS. 9A and B) or MDA-MB-231 (FIGS. 9C and D) targets with no cold competitors; (5), $^{111}$In-labeled LNCaP (FIGS. 9A and B) or MDA-MB-231 (FIGS. 9C and D) with T2-A2 as cold competitors; (6), $^{111}$In-LNCaP (FIGS. 9A and B) or MDA-MB-231 (FIGS. 9C and D) with T2-A2 pulsed with CAP-1 as cold competitors; (7), $^{111}$In-labeled LNCaP (FIGS. 9A and B) or MDA-MB-231 (FIGS. 9C and D) targets with T2-A2 pulsed with the cognate PTH-rP peptide as cold competitors.
Figure 10B:
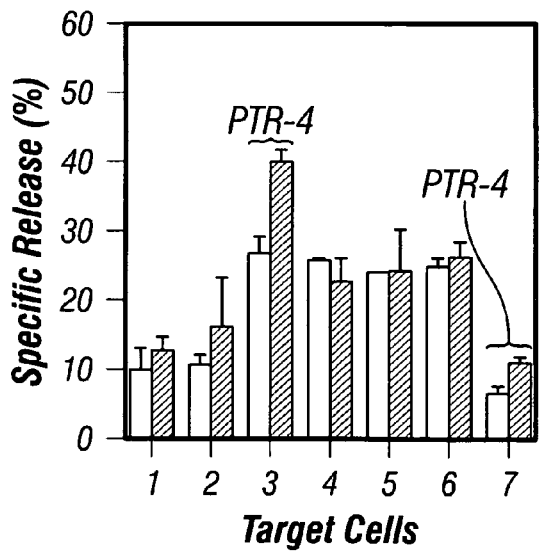
Figure 10C:
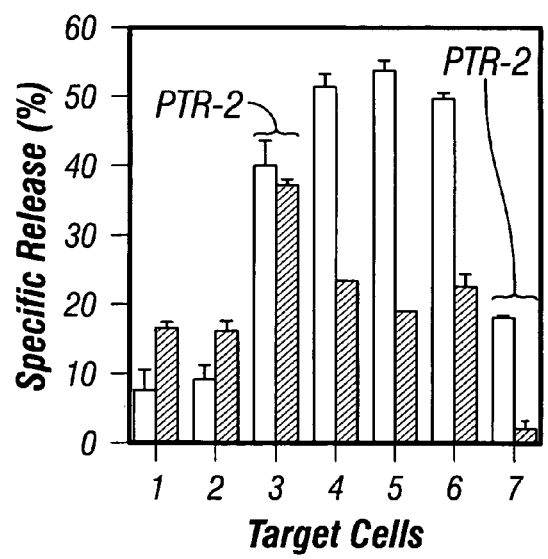
Figure 10D:
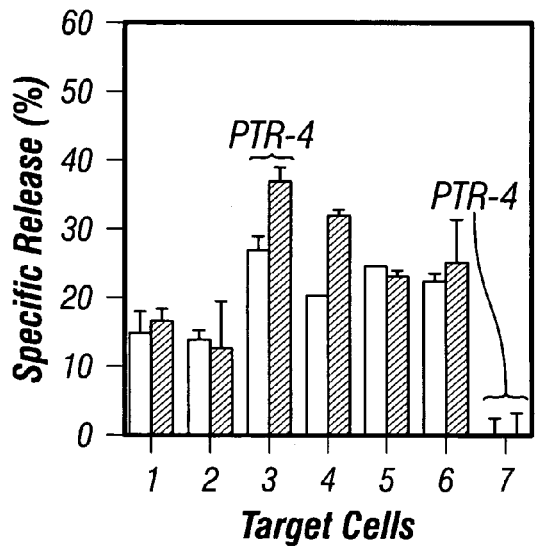

In order to investigate the functional avidity of these lymphocytes their lytic activity was tested against CIR-A2 target cells pulsed with different concentrations of the cognate peptide at the fixed E:T ratio of 25:1. With these experiments, it was found that PTR-4 compared with the PTR-2 specific CTL lines are able to induce 25% of killing in target cells pulsed with lower concentrations of cognate peptide (~10 vs 25 μg/ml) (FIGS. 8A, and B). No differences were instead observed against unpulsed or control peptide pulsed target cells.

Antitumor activity of the PTH-rP peptide specific CTL lines: In order to test the antitumor activity of CTL lines specific for PTR-2 and PTR-4, the MDA-MB 231 (breast) and LNCaP (prostate) HLA-A(*)02.01[+]/PTH-rP[+] tumor cell lines were chosen as targets. Cytotoxic assays showed that the PTH-rP peptide-specific CTL lines were able to kill both MDA-MB 231 and LNCaP cells. In contrast, no lysis was observed against the HLA-A(*)02.01[+]/PTH-rP[−] cell line SW-1463 (colon carcinoma). Furthermore, cytotoxic assays also demonstrated that the CTL-mediated killing of MDA-MB 231 and LNCaP target cells was HLA-A(*)02.01 restricted insofar as the addition of an antibody directed against HLA-A(*)02.01 molecules (A2.69) abrogated the cytotoxic effect (FIG. 9); similar results were also obtained using an anti class-I HLA (A,B,C) mAb (W6/32) (data not shown). Conversely, the addition of an isotype negative control monoclonal antibody (UPC-10) did not interfere with the process of tumor cell killing (FIG. 9).

The CTL immunophenotype and CTL activity against these target cells were investigated at the 6th, 8th, 10th and 12th in vitro stimulation, the results being very similar in terms of phenotype stability and PTH-rP/PTH-rP-peptide specific cytotoxic activity (data not shown).

Cold competition assay: Cold competition assays were performed in order to check antigen involvement and haplotype restriction of target cell killing. The CTL cytotoxic assays were performed using T2-A2 cells, unpulsed or pulsed with different peptides including PTR-2 and 4, as cold competitors and $^{111}$In-loaded MDA-MB 231 and LNCaP cells, respectively, as labeled CTL targets. The results showed an efficient competition, measured as a reduction in $^{111}$In release when cognate peptide pulsed T2 cells were used as cold competitors of MB-MDA-231 and LNCaP target cells. The CTL-mediated killing of breast and prostate carcinoma cells was, in fact, mostly abrogated by the addition of cold competitors pulsed with the specific peptide used to generate the CTL line. The addition of cold T2 cells unpulsed or pulsed with a control HLA-A(*)02.01 binding CAP-1 peptide did not interfere with the CTL-mediated killing of cancer cells (FIG. 10). The figure also shows the ability of CTL lines to recognize and kill T2 cells exposed for 24 hours to the specific peptide used for the CTL line generation. The addition of cold CEA[−]/HLA-A2.1[−] K562 cells did not interfere with the CTL-mediated target cells killing, showing no competition (data not shown in figure).

Target cell PTH-rP production and cell membrane HLA-A(*)02.01 expression were, respectively, evaluated by immunoradiometric assays (IRMA) [47] and indirect immune fluorescence flow cytometry (Table 4).

TABLE 4

HLA-A2.1 molecule expression and PTH-rP production in CTL target cells

| Target cells | HLA-A2.1 expression (%)* | PTH-rP production (pg/ml x 10[6] cells)# |
|---|---|---|
| CIR-A2 | 98.5 (2.2) | Not detectable |
| T2-A2 | 99.56 (1.22) | Not detectable |
| LNCaP | 29.8 (3.7) | 15.2 (5.5) |
| MDA-MB231 | 60.1 (2.2) | 25.1 (3.5) |
| SW1463 | 75 (3.2) | Not detectable |
| EL-4-HHD infected with influenza virosomes | 98.2 (4.24) | Not detectable |
| EL-4-HHD infected with influenza virosomes including PTH-rP gene plasmids | 96.3 (6.23) | 10.56 (3.6) |

HLA-A2.1 expression was evaluated by indirect immunofluorescence using an anti-HLA-A(*)02.01 mAb (A2.69) and an FITC conjugated goat-anti-mouse mAb. The results are expressed as percentages of fluorescent cells. Marker expression was considered negative when less than 4%. The results are expressed as the percentage of each cell sample reactive with mAb. Routinely, 2-4% cells are stained when treated with a non-priming mAb or an isotype-related control mAb.
PTH-rP production was evaluated using a sandwich immunoradiometric assay (IRMA); values of less than 1.5 pg were considered negative.
*#Numbers in parentheses represent standard deviations (SD).

Altogether these results demonstrate that killing of HLA-A(*)02.01[+]/PTH-rP[+] tumor lines was a peptide mediated and HLA-A(*)02.01 restricted phenomena.

Antigen specific CTL in HHD transgenic mice vaccination with PTH-rP peptides: In order to evaluate the immunogenic potential of PTH-rP peptides in vivo, HLA-A(*) 02.01 transgenic mice (HHD) mice were injected, respectively, with PTR-2, PTR-4 peptide and with an irrelevant peptide as a control. PTR-2, PTR-4 showed, respectively, 100 and 60% amino acid homology with the respective mouse peptide sequences. Twenty five days after the first peptide injection the spleen cells were isolated and restimulated in vitro with the cognate peptide for six days. The spleen cell cultures were then tested against autologous EL4-HHD target cells pulsed with the cognate peptide or expressing PTH-rP after infection with PTH-rP gene plasmids included in influenza virosomes (GC90V).

The construct GC90V used in this study was generated previously. The expression of PTH-rP in the GC90V infected EL4-HHD target cells was evaluated by means of IRMA, RT-PCR detection of specific mRNA, and immunofluorescence using a rabbit anti-PTH-rP serum (Table 4).

Figure 11A:
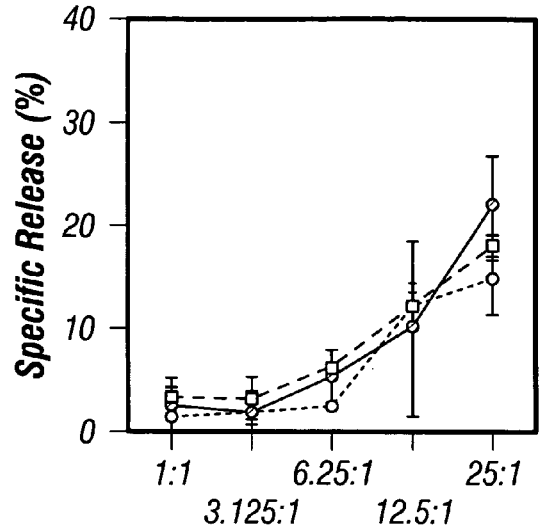
FIG. 11: this figure shows the PTH-rP specific cytotoxic activity of spleen cells derived from HHD mice immunized with the PTH-rP peptides. Cultured spleen cells derived from HHD mice immunized with PTH-rP peptides recognize and kill HLA-A(*)02.01$^+$EL-4-HHD target cells expressing PTH-rP. PTH-rP specific cytotoxic activity of mouse spleens pooled from different mouse groups was tested against EL-4-HHD and EL-4-HHD target cells infected with the virosome including the PTH-rP gene plasmids (GC90V). The figure shows the cytotoxic effects of the spleen cells derived from mice immunized with control peptide (A), PTR-2 (B) or PTR-4 peptide (C) against: 1-EL-4-HHD target cells infected with GC90V (filled circles and bold lines); 2-EL-4-HHD target cells infected with the GC90V and exposed to the CTL in the presence of anti A2.69 mAb (empty squares and dashed lines); 3-EL-4-HHD infected with influenza virosomes including the plasmid backbone (pcDNA3) (empty circles and dashed lines). The addition of a negative isotype control mAb (UPC-10) did not affect the killing of EL-4-HHD target cells infected with the GC90V mediated by spleen cells from mice receiving PTR-1 and PTR-2 peptides (data not shown in the figure). The data are from three different experiments with similar results. The differences between 1-[EL-4-HHD target cells infected with the virosome including the PTH-rP gene plasmids (GC90V)] and both 2-(EL-4-HHD target cells infected with the GC90V and exposed to the CTL in the presence of anti A2.69 mAb) and 3-(EL-4-HHD infected with influenza virosomes including the plasmid backbone (pcDNA3) were statistically significant only for the groups B and C ($P<0.05$).
Figure 11B:
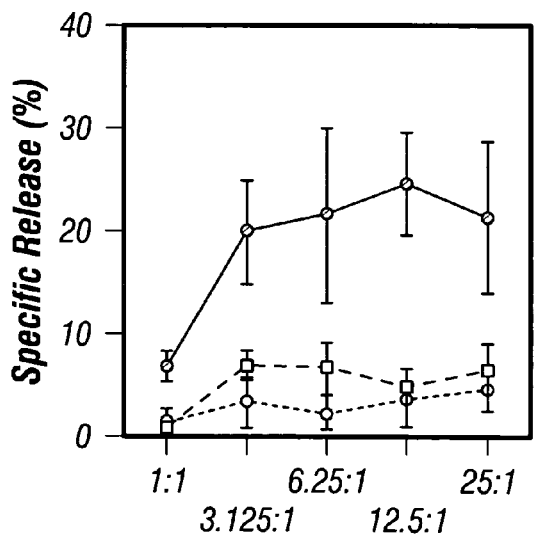
Figure 11C:
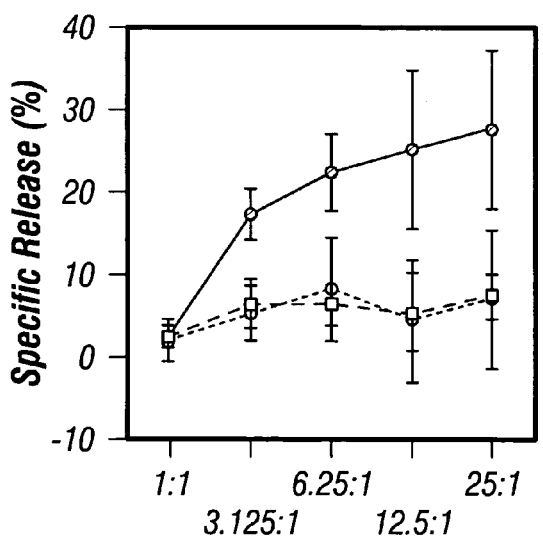

Significant PTH-rP and PTH-rP peptide specific cytotoxic activity was observed only for the spleen cells derived from mice immunized with PTR-2 or PTR-4. These T cells were able to kill EL4-HHD pulsed with the cognate peptide (PTR-2 and -4 respectively) (data not shown) and the same cells producing PTH-rP after infection with the GC90V (FIG. 11). Spleen cells derived from mice immunized with PTR-2 and -4 could not kill the same target cells pulsed with the control CAP-1 peptide or pulsed with the PTR peptide not used for mouse immunization (data not shown). Target cell lysis was class-I MHC restricted, since CTL activity was abrogated when the anti-HLA-A(*)02.01 mAb was added to the cytotoxic assays (FIG. 11) whereas the addition of a negative isotype control mAb (UPC-10) did not affect the killing (data not shown). No cytotoxic activity was detected against parental uninfected EL4-HHD cells (data not shown) or infected with the virosome including the plasmid backbone pcDNA3 (FIG. 11). Spleen cells derived from HHD mice immunized with the control peptide or not injected at all, did not give rise to a PTH-rP specific CTL activity; although; they had slight lytic activity against the target cells at a high E:T ratio, it was not specific for PTH-rP nor class-I MHC-restricted (FIG. 11), thus suggesting the presence of a residual NK activity. Taken together, these results suggest that the vaccination of HHD mice with PTR-2 and PTR-4 peptides generates a peptide specific CTL response capable of recognizing naturally processed peptides on tumor cells expressing PTH-rP.

In vivo study of HHD transgenic mice after vaccination with PTH-rP peptides: In order to evaluate the tissue specific toxicity and autoimmunity induced by PTH-rP peptide vaccination, a post-mortem histology study of tissues chosen because of their reported physiologic expression of PTH (parathyroids) or low levels of PTH-rP was performed 25 days after the first peptide injection. Four μm-thick paraffin sections taken from the parathyroid, skin, derma, and bone tissues of PTH-rP peptide injected HHD mice were collected at the end of the vaccination cycle, and stained with hematoxylin-eosin-safranin. The tissues were chosen because of their potential expression of PTH-rP proteins in amounts theoretically detectable in vivo by a secondary PTH-rP directed T cell response. This study failed to demonstrate in the control as well as in the vaccinated group of mice any PTH-rP mRNA expression in these tissues, probably due to the extremely low production of this protein in normal conditions (data not shown). Histology showed the absence of pathological microscopic lymphocyte infiltration and no abnormal inflammatory tables of stained tissues including the parathyroids (data not shown).

Furthermore, in order to exclude the possibility that the PTH-rP directed immune response may cross-react with PTH expressing cells in the parathyroids or in some way affect the osteoclast activity in the bone tissue, the effects of PTH-rP peptide vaccination of HHD mice on their $Ca^{++}$ turn over were investigated. To this end, serum levels of $Ca^{++}$ ions were evaluated during treatment in blood samples collected 11 and 25 days after the first PTH-rP peptide injection. In order to exclude a delayed effect, blood samples were also drawn 52 days after the first peptide administration in a different set of animals receiving the same above described treatments. Control blood samples were collected from HHD mice not injected or injected with an irrelevant peptide.

The results demonstrate absence of serum $Ca^{++}$ ion fluctuations in any of the transgenic animals, thus indicating that the vaccination with PTR peptides elicits a PTH-rP specific CTL response without affecting parathyroid functions as well as bone osteoclast activity (Table 5), and without inducing direct cell-mediated bone tissue damage. Taken together, these results suggest that the injection of PTH-rP peptides in HHD transgenic mice generates a PTH-rP specific response in vivo without affecting normal tissues.

TABLE 5

Serum [$Ca^{++}$] levels in HHD-transgenic mice during the immunological treatment[a]

| Reagent administered[b] | Day 11[c] | | | Mean | Day 25[d] | | | Mean | Day 52[e] | | | Mean |
|---|---|---|---|---|---|---|---|---|---|---|---|---|
| Control | 1.18 | 1.08 | 1.10 | 1.12 | 1.50 | 1.61 | 1.55 | 1.55 | 1.45 | 1.26 | 1.51 | 1.41 |
| PTR-2 | 1.11 | 1.15 | 1.04 | 1.1 | 1.56 | 1.59 | 1.49 | 1.54 | 1.56 | 1.43 | 1.41 | 1.46 |
| PTR-4 | 0.99 | 1.35 | 1.15 | 1.16 | 1.57 | 1.48 | 1.55 | 1.53 | 1.36 | 1.61 | 1.55 | 1.51 |

There were no significant changes in serum [$Ca^{++}$] levels after the first and second PTH-rP peptide injection in three different mice for each group. The differences between the groups receiving PTH-rP peptides and controls were not statistically significant.

[a]human synthetic thyreocalcitonin (0.1 mg in 1 ml of 0.9% saline solution) injected sc. in the dorsal neck was used as a positive control, which is capable to induce after 6 hours of treatment hypocalcemia (0.64 +/− 0.645 mmol/L), in a group of three mice.
[b]The sequence homology between the human and murine PTH-rP protein sequences was >90%. Amino acid sequence homology between the human PTH-rP peptides and the analogous murine sequences in PTH-rP was 100% for PTR-2, and 60% for PTR-4.
[c]Blood sample drawn 11 days after the first peptide administration in three different animals.
[d]Blood sample drawn 25 days after the first peptide administration in the same animals.
[e]Blood sample drawn 52 days after the first administration in a different set of animals receiving the same treatment administered in the same way.

Example 5

This example shows that the administration of virosomes (IRIVs) with PTH-rP plasmids in combination with PTH-rP peptide boosters induce efficient T cell mediated immune responses to tumor cells expressing PTH-rP. Vaccination with the virosomes containing PTH-rP gene plasmids is shown to lead to a multi-PTH-rP peptide specific T cell response, capable of destroying PTH-rP expressing tumor cells. The virosomes containing PTH-rP plasmids can be used to stimulate tumor specific T cell responses by mucosal infection of transgenic mice expressing human MHC molecules. Booster injections with PTH-rP peptides may also increase the avidity of the anti-tumor T cells specific for PTH-rP HHH/hβ2microglobulin (B2 m)/hCD8α(H3CD8) transgenic mice: C57BL/6 β2m-deficient and double mutant H2-Kb Db−/− mice have been already described. Simple transgenic mice have been obtained by classical transgenesis of cDNAs encoding for human μ2 m, the entire HLA-A*0201 molecule and CD8 α molecule. In order to obtain triple transgenic mice, triple KO and the above cited mouse strains were inter-crossed obtaining mice that express entire HLA-A*0201 molecules, human β2 m and human CD8α. The Db− mice were generated from the 129 (H-2K) and C57BL/6 (H-2b) mice. The HHD molecules were first transduced in mice with a genetic background of SJL/J (H-2s) and C57BL/6. After two backcrossing of the H-2Db− and β2 m murine KO mice with C57BL/6 mice, they were crossed with the HHD transgenic mice to produce the HHD transgenic/H-2Db− and β2 m murine− colonies. Thus, the HHD mice used in this study have a mixed genetical background of mainly C57BL/6, little 129 and trace of SJL/J mice. The A2A2Kd mice therefore show a C57BL/6 background. Furthermore, they are β2 m −/−, Db−/− and express a HLA-A*0201 monochain composed of a chimeric heavy chain α1 and α2 domains of HLA-A*0201 and the α3 and intracellular domains of Db linked by its N-terminus to the C-terminus of the human β2 m by a 15 amino acid peptide arm. Mice were housed in a temperature-controlled, light cycled room. All in vivo experiments were performed in accordance with local ethical guidelines. The H3CD8 mice strain transgenic for human HLA-A*02.01 α1, α2 and α3 domains and the human CD8 molecule is the result of a back-cross between the human CD8 transgenic mice (Sherman L., Scripps, La Jolla, USA) and the HHH transgenic mice expressing the monochain α1, α 2 and α 3 of human HLA-A*02.01 molecule covalently linked to hβ2 m (Lemonnier F., personal communication). The back-cross obtained is a triple transgenic HHH-hβ2 m+/+/hαCD8 (H3CD8) mouse that expresses the three human molecule (HHH, hβ2 m and hαCD8) in a homozygote way. The H3CD8 is a triple murine β2 m, H-2Db and H-2Kb knock out mouse.

Cell Cultures: The EL4/HHD cells are Tap competent murine thymoma cells co-transfected with the HHD monochain (Pascolo et al., J. Exp. Med. 185(12): 2043-2051, 1997). Transient transfectants EL4/HHD/PTHrP were obtained by transfection of EL4/HHD cells with GC90 plasmid as previously described. Prostate carcinoma cell lines, LNCaP were purchased from the American Type Culture collection (Rockville, Md.). The mycoplasma-free cultures were maintained in complete medium [Roswell Park Modified Iscowes (RPMI)-1640 for LNCaP and EL-4-HHD, [Life Technologies Inc. (Gibco BRL) Grand Island, N.Y.] supplemented with 10% fetal bovine serum (FBS), 2 mM l-glutamine, 100 U/ml penicillin, and 100 μg/ml streptomycin [Life Technologies, Inc].

Peptide synthesis: Peptides PTR-1 (AVSEHQLLH, SEQ ID NO: 2), PTR-2 (FLHHLIAEIH, SEQ ID NO: 3), PTR-3 (WLDSGVTGS, SEQ ID NO: 4) and PTR-4 (TSTTSLELD, SEQ ID NO: 5) were synthesized using a solid phase automatic peptide synthesizer (model syto, MultiSyntech, Witten, D) and the fluorenylmethoxycarbonyl (Fmoc)/diisopropylcarbodiimide (DIC)/1-hydroxybenzotriazole (HOBT) strategy. They were cleaved from the resins and defracted by treatment with trifluoroacetic acid containing ethandiethiol, water trisbuthyl silone and anisole (93/2.5/2/1.5/1). The crude peptides were purified by HPLC using a Vydac C18 column (25 cm×1 cm, 10 μm). The products were dissolved in bidistilled water, sterile filtered and frozen at −70° C. at a concentration of 2 mg/ml. Peptide purity was more than 90% as analyzed by high-performance liquid chromatography (HPLC). The CAP-1 peptide was kindly donated by Dr. J. Schlom (EOS, NCI, Bethesda, Md., USA).

ELISpot assay: Peripheral lymphocytes isolated from blood samples collected from the retro-orbitary sinus of the different treatment groups of mice were pooled and examined for PTH-rP epitope peptide specific precursor frequency by using INF-γ ELISpot assay (Miyahira et al., J. Immunol. Methods, 181(1), 45-54, 1995). Briefly, nitrocellulose-bottomed 96-well plates (Millipore) were coated for 2 h at 37° C. followed by overnight incubation at 4° C. with rat anti-mouse IFN-γ antibody (clone R4-6A2; Pharmigen). Dilutions of responder cells in complete medium were cultured in triplicate with or without 10 μM peptide epitope for 40 h. Plates were then washed and incubated with biotinylated IFN-γ antibody (clone XMG1.2; Pharmigen) followed by streptavidin conjugated to alkaline phosphatase (Boehringer Mannheim). Spots were visualized using BCIP/NBT alkaline phosphatase substrate (Promega). IFN-γ-secreting cells were counted using the automated iPTH-rP derived analysis system ELISpot Reader (AID Strassberg, Germany). The Wilcoxon two tail-rank test was performed to determine whether there was a statistically significant difference between the number of IFN-γ secreting cells in the wells stimulated with the peptides of interest and wells containing spleen cells without peptide and with a control peptide (influenza matrix peptide).

Generation of a PTH-rP plasmid and influenza virosomes: The PTH-rP gene was amplified from the DU-145 prostate carcinoma cell line as described previously and cloned in BamHI-EcoRI sites of the pcDNA3 expression vector (In-Vitrogen) in order to obtain the recombinant plasmid GC90. The construct was grown in DH5 cells (Life Technologies Inc.). Plasmid DNA was purified using the Qiagen Endo Free plasmid kit (QIAGEN) as described by the manufacturer. The influenza virosomes (IRIV) were prepared as described elsewhere. Non-encapsulated plasmids were separated by 0.1 gel filtration on a High Load Superdex 200 column (Pharmacia) equilibrated with sterile phosphate-buffered solution (PBS). The void volume fractions containing the virosomes and encapsulated plasmids were eluted with PBS and collected.

Cell transfection: Approximately $10^5$ target cells (spleen cells for CTL in vitro stimulation and Vero and EL-4/HHD cells) were grown in 6 well microplates at 37° C. and infected with 0.3 μg of DNA-virosomes or transfected with 1 μg of plasmid DNA using the Effectene Transfection reagent (QIAGEN) as described by the manufacturer. After two days, PTH-rP antigen expression was analysed by evaluating the presence of the specific mRNA by RT-PCR and by immunofluorescence. Briefly, the cells were washed twice with PBS, fixed with cold methanol/acetone and treated with a rabbit anti-PTH-rP serum (Calbiochem) followed by FITC-conjugated goat anti-rabbit IgG (1/100) (DBA). The coverslips were mounted on slides and examined using a Diaplan-n microscope (Leitz).

Immunization of H3CD8 mice: Five groups of six H3CD8 mice received 20 μl of GC90/IRIV (containing 5 μg of plasmid, 0.6 μg of influenza HA, and 40 ng of Escheriagen, Escheria coli heat-labile toxin) after intranasal inoculation (in.). In order to enhance the immunological activity of the GC90/IRIV an i.n. priming with 20 μl of empty IRIV was performed 10 days before the first immunization with GC90/IRIV. Mice in the control groups received in. inoculation of 20 μl of IRIV, or 20 μl IRIV containing the plasmid backbone (pcDNA3). All mice with the exception of those included in the control groups, were subsequently reboosted 21 and 42 days after the first immunization with: GC90/IRIV; PTR-1; -2, -3, and -4, respectively. PTH-rP peptides were administered by subcutaneous (sc.) injection at the base of the tail with 100 μg of peptide emulsified in incomplete Freund's adjuvant (IFA) in the presence of 140 μg of the IA$^b$ restricted HBV core-derived T-helper epitope (128-140; sequence TPPAYRPPNAPIL, SEQ ID NO: 6).

On days 21 and 56 after the first immunization, sera samples were collected from the retro-orbital sinus for serum Ca$^{++}$ ion level evaluation. Two weeks after the final boost, the mice were sacrificed and 4 μM-thick paraffin sections were made from sampled tissues and stained with hematoxylin-eosin-safranin (Merck, Germany).

Spleen cells ($5 \times 10^7$ cells in 10 ml) were harvested on day 56 and cultured for 6 days in serum free AIM-V [Life Technologies Inc. (Gibco BRL)], with 2 mM 1-glutamine, 100 U/ml penicillin, and 100 μg/ml streptomycin, and 100 IU of Interleukin 2, and in vitro stimulated with autologous irradiated spleen cells infected with GC90/IRIV+/−the cognate peptide (10 μM) used for mouse reboosting. After further 6 days, the bulk responder populations were tested for PTH-rP specific cytotoxicity.

Cytotoxicity Assay: Target cells were labeled with 100 μCi of Na$_2$Cr$^{51}$O$_4$ (Amersham, Aylesbury, UK) for 60 minutes at room temperature. Target cells ($0.5 \times 10^4$) in 100 μl of complete medium (see below) were added to each of the wells in 96-well flat-bottomed assay plates (Corning Costar Corp.). The labeled targets were incubated at 37° C. in 5% CO$_2$ before the addition of effector cells. The T cells were then suspended in 100 μl of AIM-V medium and added to the target cells. The plates were incubated at 37° C. for 18 hours, and the supernatants harvested for γ-counting with harvester frames (Skatron, Inc., Sterling, Va.). The determinations were made in triplicate and standard deviations were calculated. All of the experiments were repeated at least three times. Specific lysis was calculated as follows:

$$\% \text{ specific lysis} = \frac{\text{observed release (cpm)} - \text{spontaneous release (cpm)}}{\text{total release (cpm)} - \text{spontaneous release (cpm)}} \times 100$$

Spontaneous release was determined from the wells to which 100 μl of complete medium were added instead of effector cells. Total releasable radioactivity was obtained after treating the target with 2.5% Tryton x-100.

Blocking experiments: For HLA blocking experiments, UPC-10 (Cappel/Organon Technique Corp., West Chester, Pa.) control mAb or anti-HLA-A2 (A2.69, #189HA-1; One Lambda, inc., Canoga Park, Calif.) mAb were added to the $^{51}$[Cr] loaded target cells (EL4/HHD/PTHrP and LNCaP) and incubated for 1 hour prior the cytotoxic assay.

Statistical analysis: Statistical analysis of differences between means was done using Stat View statistical software (Abacus Concepts, Berkeley, Calif.). The results were expressed as mean of four determinations derived from three different experiments +/− standard deviation. Differences among means, were determined by the two tailed Student T test for paired samples. Differences were considered statistically significant when P value was <0.05.

Vaccination of H3CD8 mice with GC90/IRIV+/−PTH-rP epitope peptides: In order to evaluate its immunogenic potential we administered intranasal GC90/IRIV into five different groups of H3CD8 mice. After 21 days, IFN-γ ELISPot assays were carried out on peripheral lymphocytes isolated from blood samples, taken from the retro-orbitary sinus of all mice groups. Table 6 shows the ex vivo evaluation of IFN-γ secreting T cells specific for the four known HLA-A*02.01 binding PTH-rP peptide epitopes after GC90/IRIV vaccination. The uppermost lymphocyte precursor quote after priming was specific for PTR-2 and PTR-4 (Table 6).

TABLE 6

In vitro detection of Interferon (IFN) γ secreting T cells specific for PTH-rP derived epitope peptides with HLA-A * 02.01 binding amino acid consensus motifs[a]

| | | Antigen peptide | | | |
|---|---|---|---|---|---|
| Priming | Re-boost | PTR-1 | PTR-2 | PTR-3 | PTR-4 |
| [b]GC90/IRIV | NA | 10 | 13 | 12 | 34 | ? |
| [b]IRIV | NA | ? | ? | ? | ? | ? |
| [c]GC90/IRIV | GC90/IRIV | 65 | 70.5 | 62.5 | 52 | ? |
| [c]GC90/IRIV | PTR-1 | 16.5 | ND | ND | ND | ? |
| [c]GC90/IRIV | PTR-2 | ND | 33 | ND | ND | ? |
| [c]GC90/IRIV | PTR-3 | ND | ND | 20.5 | ND | ? |
| [c]GC90/IRIV | PTR-4 | ND | ND | ND | 24 | ? |
| [c]IRIV | IRIV | 1 | 20 | 21 | 11 | ? |
| | ESCHERIAGEN | ? | ? | ? | ? | ? |

[a]PTH-rP peptide specific T cell response was evaluated by ELISpot Assay performed on group pooled peripheral lymphocytes taken from the retro-orbital sinus. Results are expressed as number of peptide specific IFN-γ secreting T cells per million of total lymphocytes.
[b]ELISpot Assay performed after 21 days from the first inoculation.
[c]ELISpot Assay performed after 56 days from the first inoculation In order to investigate a possible synergistic interaction of GC90/IRIV with PTH-rP epitope peptides, the PTH-rP specific CTL response was then tested in the five separate groups of previously GC90/IRIV vaccinated mice after they had received a different re-boost. The first group was re-boosted twice with GC90/IRIV, while the other four groups were re-boosted twice with one of the known PTH-rP peptides (PTR-1, PTR-2, PTR -3, PTR -4). Peripheral lymphocytes derived from all groups were collected 56 days after the priming, and examined by ELISpot analysis. The assay showed a multi epitope specific CTL response in mice receiving GC90/IRIV only; while a lower number of cognate peptide specific T cell precursors frequency was detected in mice re-boosted with the single PTH-rP peptides (Table 6). The two additional groups used as a negative control showed no response at all. Taken together, these results suggest that GC90/IRIV is immunogenic in vivo and that the re-boosting with PTH-rP epitope peptides is not necessary to enhance the number of PTH-rP peptide specific precursors.

Figure 12A:
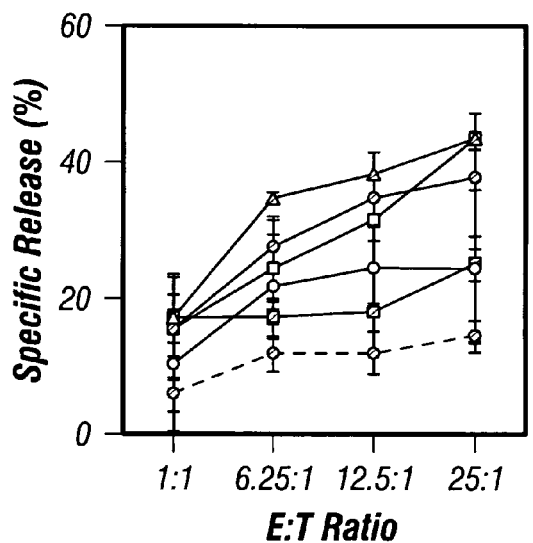
FIG. 12: this figure shows the PTH-rP specific cytotoxic activity of spleen cells derived from HHH/hCD8 mice immunized with GC90/IRIV+/−PTH-rP peptides. Cultured spleen cells derived from different groups of HHH/hCD8 mice respectively immunized with: GC90/IRIV (-●-); GC90/IRIV+PTR-1 (-■-); GC90/IRIV+PTR-2 (-▲-); GC90/IRIV+PTR-3 (-○-); GC90/IRIV+PTR-4 (-□-); and empty IRIV group (--Δ--). PTH-rP specific cytotoxic activity of mouse spleens pooled from different mouse groups was tested against EL-4-HHD target cells transfected with the PTH-rP gene (A) in fresh medium or in presence of anti A2.69 mAb (B). The figure shows that only the spleen cells derived from mice immunized with GC90/IRIV+/−PTR peptides were able to lyse the EL-4-HHD target cells transfected with the PTH-rP gene. The lysis was PTH-rP specific since EL-4-HHD transfected with the plasmid Backbone were not recognized by the effectors (data not shown in figure). The lysis was HLA-A2.1 restricted since abrogated by the anti A2.69 mAb. Conversely the addition of a negative isotype control mAb (UPC-10) did not affect the killing of EL-4-HHD (data not shown in the figure). The data are from three different experiments with similar results. Differences between 1-spleen cells derived from GV90IRIV+/−PTR peptides and control against EL-4-HHD target cells transfected with the PTH-rP gene plasmids and 2-spleen cells derived from GV90IRIV+/−PTR peptides against EL-4-HHD target cells transfected with the PTH-rP gene plasmids in presence or absence of A2.69 mAb were statistically significant ($P<0.05$).

PTH-rP specific anti-tumor activity of CTL derived from GC90/IRIV vaccinated mice: the PTH-rP specific CTL activity of spleen cells derived from the different groups of mice vaccinated with GC90/IRIV, GC90/IRIV+/−each one of the PTH-rP peptides or IRIV/pcDNA3 was also investigated. In order to enhance the number of PTH-rP specific precursors, pooled spleen cells derived from the different immunization groups were in vitro stimulated with low dose IL-2 and autologous irradiated spleen cells transfected with GC90 (PTH-rP plasmid). Spleen cell cultures derived from mice vaccinated with GC90/IRIV were able to kill EL4/HHD/PTHrP transfectants (FIG. 12a) as well as HLA- A*02.01+/PTHrP+ Prostate carcinoma LNCaP cells (FIG. 13a). Spleen cell cultures derived from H3CD8 mice primed with GC90/IRIV and boosted with each one of the four PTHrP peptides showed a marked lysis of EL4/HHD/PTHrP target transfectants as well as LNCaP target cells (FIGS. 12 and 13). The maximal lysis was observed in spleen cell cultures derived from mice that had received re-boost with PTR-2 and PTR-4. Spleen cell cultures generated from control mice that had received no treatment or IRIV/pcDNA3 gave rise to a minimal cytotoxic activity against EL4/HHD/PTHrP transfectants and were not able to kill the LNCaP target cells.

Figure 12B:
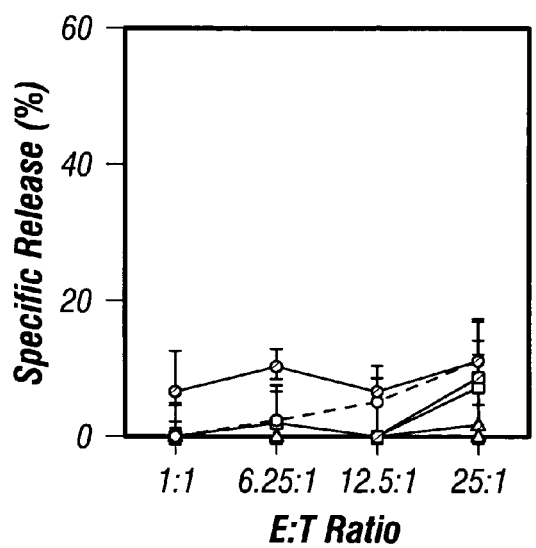
Figure 13A:
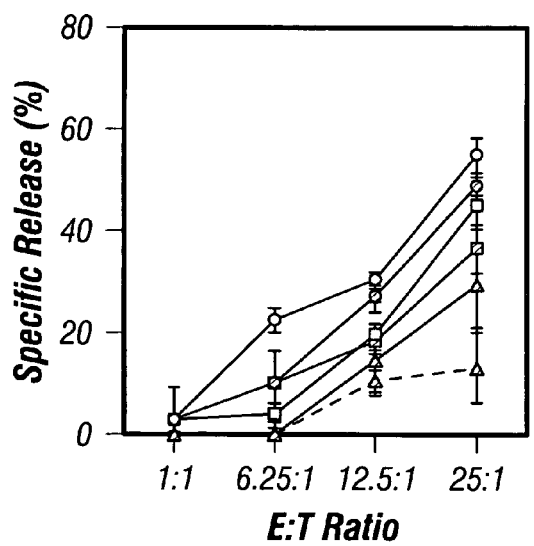
FIG. 13: this figure shows the PTH-rP specific cytotoxic activity of spleen cells derived from HHH/hCD8 mice immunized with GC90/IRIV+/−PTH-rP peptides in vitro against HLA-A(*)02.01+ prostate carcinoma (LNCaP) cells capable of producing PTH-rP. Cultured Spleen cells were derived from different groups of HHH/hCD8 mice respectively immunized with: GC90/IRIV (-●-); GC90/IRIV+ PTR-1 (-■-); GC90/IRIV+PTR-2 (-▲-); GC90/IRIV+ PTR-3 (-○-); GC90/IRIV+PTR-4 (-□-); and empty IRIV group (--Δ--). PTH-rP specific cytotoxic activity of mouse spleens pooled from different mouse groups was tested against LNCaP target cells in fresh medium (A) or in presence of anti A2.69 mAb (B). The figure shows that only the spleen cells derived from mice immunized with GC90/IRIV+/−PTR peptides were able to lyse LNCaP target cells. The lysis was HLA-A2.1 restricted since abrogated by the anti A2.69 mAb. The addition of isotype mAb (UPC-10) used as an negative control, did not affect the killing of EL-4-HHD (data not shown in the figure). The data are from two different experiments with similar results. Differences between 1-spleen cells derived from mice vaccinated with GV90/IRIV+/−PTR peptides and control against LNCaP, and 2-spleen cells derived from GV90IRIV+/−PTR peptides against LNCaP target cells in presence or absence of A2.69 mAb were statistically significant (P<0.05). The spontaneous release in these assays in the presence or absence of mAbs without effectors was always less than 10%.
Figure 13B:
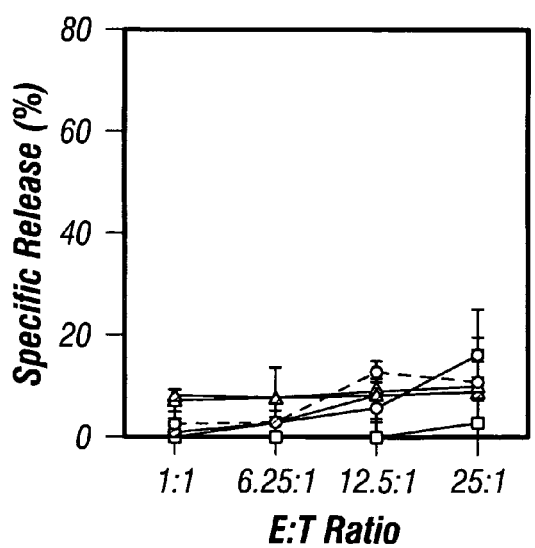

None of the spleen cell cultures was able to kill EL4/HHD target cells infected with pcDNA3/IRIV and not expressing PTH-rP (FIGS. 12 and 13). The lysis of EL4/HHD/PTHrP transfectants as well as LNCaP target cells was HLA-A*02.01 restricted since completely abrogated by an anti HLA-A*02.01 moAB (A2.69) (FIGS. 12B and 13B); conversely the use of a negative control moAb did not affect the target cell killing (data not shown)

These results demonstrate that vaccination of H3CD8 mice with GC90/IRIV generated in vivo an epitope peptide specific CTL able to kill tumor targets that naturally process PTH-rP.

In vivo study of H3CD8 mice after GC90/IRIV vaccination: Tissue specific toxicity and autoimmunity induced by GC90/IRIV+/−PTH-rP epitope peptides was also evaluated in H3CD8 mice by performing 56 days after the first immunization a post-mortem histology study of tissues selected for their physiologic PTH expression (parathyroids) or low levels of PTH-rP expression (skin, derma, breast). The histology showed absence of pathological microscopic lymphocyte infiltration and no abnormal inflammatory tables of stained tissues in any of the H3CD8 mouse (data not shown). Taken together, these results demonstrate that GC90/IRIV+/−peptides generate CTL precursors specific for PTHrP epitopes which are not able to affect the normal tissues in vivo.

Considering that the transient expression of the whole PTHrP protein in mice vaccinated with GC90/IRIV could affect their physiologic $Ca^{++}$ turn over, serum levels of $Ca^{++}$ ions during treatment in all mice groups were monitored (blood samples collected 21 and 56 days after the first inoculation of GC90/IRIV), with no finding of evidence of serum $Ca^{++}$ ion fluctuations. In conclusion GC90/IRIV its able to elicit a PTH-rP specific CTL response in transgenic animals without affecting bone osteoclast activity (Table 7).

TABLE 7

Serum [$Ca^{++}$] Levels in mice after vaccination with GC90/IRIV +/− PTH-rP peptides

| [$Ca^{++c}$concentration], mmol/L Reagent administered[a] | Day 0[b] | | | Mean | | | | day 56[c] Mean |
|---|---|---|---|---|---|---|---|---|
| Control | 1.45 | 1.21 | 1.32 | 1.32 | 1.55 | 1.55 | 1.61 | 1.57 |
| HTL/HTL | 0.97 | 1.04 | 1.21 | 1.07 | 1.45 | 1.45 | 1.46 | 1.45 |
| GC90/IRIV + GC90/IRIV | 1.26 | 1.29 | 1.03 | 1.19 | 0.59 | 0.94 | 1.06 | 0.89 |
| GC90/IRIV + PTR-1 | 0.99 | 1.12 | 1.43 | 1.18 | 1.14 | 0.92 | 1.21 | 1.09 |
| GC90/IRIV + PTR-2 | 1.23 | 0.96 | 0.99 | 1.06 | 0.82 | 1.10 | 1.09 | 1.00 |
| GC90/IRIV + PTR-3 | 1.16 | 1.41 | 0.93 | 1.16 | 1.03 | 1.26 | 1.02 | 1.10 |
| GC90/IRIV + PTR-4 | 1.36 | 1.07 | 0.89 | 1.10 | 1.02 | 0.83 | 1.03 | 0.96 |

There were no significant changes in serum [$Ca^{++}$] levels induced by any vaccination group compared with the controls.
[a]The sequence homology between the human and murine PTH-rP protein sequences was >90%. Amino acid sequence homology between the human PTR peptides and the analogous murine sequences in PTH-rP was 100% for PTR-1, 100% for PTR-2, and 60% for PTR-4.
[b]Blood sample drawn before the first administration in three different animals.
[c]Blood sample drawn 56 days after the first first administration in the same animals.

What is claimed is:

1. An isolated immunostimulatory parathyroid hormone-related (PTH-rP) peptide consisting of an amino acid sequence selected from the group consisting of SEQ ID NO:3, SEQ ID NO:4 and SEQ ID NO:5.

2. An immunostimulatory peptide comprising a T helper epitope linked to an amino acid sequence selected from the group consisting of SEQ ID NO:3. SEQ ID NO:4 and SEQ ID NO:5.

3. An isolated immunostimulatory peptide consisting of two or more amino acid sequences selected from the group consisting of SEQ ID NO:3, SEQ ID NO:4 and SEQ ID NO:5.

4. The peptide of claim 3 wherein the amino acid sequences are arranged in sequential or concatameric.

5. An immunostimulatory peptide comprising a T helper epitope linked to two or more amino acid sequence selected from the group consisting of SEQ ID NO:3, SEQ ID NO:4 and SEQ ID NO:5.

6. A composition comprising a virosome encapsulating the immunostimulatory peptide of any one of claims 1, 2, 3, or 5.

7. A composition comprising a virosome crosslinked to the immunostimulatory peptide of any one of claims 1, 2, 3, or 5.

8. A kit comprising the PTH-rP peptide of any one of claims 1, 2, 3, or 5 and instructions for use.

* * * * *

UNITED STATES PATENT AND TRADEMARK OFFICE
CERTIFICATE OF CORRECTION

| | | |
|---|---|---|
| PATENT NO. | : 7,378,495 B2 | Page 1 of 1 |
| APPLICATION NO. | : 10/691125 | |
| DATED | : May 27, 2008 | |
| INVENTOR(S) | : Correale et al. | |

It is certified that error appears in the above-identified patent and that said Letters Patent is hereby corrected as shown below:

In claim 2, column 48, line 59, please delete "." and replace it with --,--.

In claim 4, column 48, line 66, please insert the word --order-- between "concatameric" and ".".

In claim 5, column 49, line 2, please delete "sequence" and replace it with --sequences--.

Signed and Sealed this

Nineteenth Day of August, 2008

JON W. DUDAS
*Director of the United States Patent and Trademark Office*